(12) United States Patent
Shan et al.

(10) Patent No.: US 9,249,157 B2
(45) Date of Patent: Feb. 2, 2016

(54) TRICYCLIC HETEROCYCLE COMPOUNDS

(71) Applicant: BRISTOL-MYERS SQUIBB COMPANY, Princeton, NJ (US)

(72) Inventors: Weifang Shan, Princeton, NJ (US); Ashvinikumar V. Gavai, Princeton Junction, NJ (US); James Aaron Balog, Lambertville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/429,923

(22) PCT Filed: Sep. 20, 2013

(86) PCT No.: PCT/US2013/060831
§ 371 (c)(1),
(2) Date: Mar. 20, 2015

(87) PCT Pub. No.: WO2014/047390
PCT Pub. Date: Mar. 27, 2014

(65) Prior Publication Data
US 2015/0246930 A1  Sep. 3, 2015

Related U.S. Application Data

(60) Provisional application No. 61/703,933, filed on Sep. 21, 2012.

(51) Int. Cl.
*C07D 487/04* (2006.01)
*C07D 498/04* (2006.01)
(Continued)

(52) U.S. Cl.
CPC ............ *C07D 498/04* (2013.01); *A61K 31/138* (2013.01); *A61K 31/337* (2013.01);
(Continued)

(58) Field of Classification Search
CPC .......................... C07D 487/04; C07D 498/04
See application file for complete search history.

(56) References Cited

U.S. PATENT DOCUMENTS

| 4,981,847 A | 1/1991 | Sato et al. |
| 5,322,842 A | 6/1994 | Sato et al. |

(Continued)

FOREIGN PATENT DOCUMENTS

| EP | 0669334 | 8/1995 |
| WO | WO 97/36879 | 10/1997 |

(Continued)

OTHER PUBLICATIONS

U.S. Appl. No. 14/627,573, filed Feb. 20, 2015, Gavai et al.

(Continued)

*Primary Examiner* — Bruck Kifle
(74) *Attorney, Agent, or Firm* — Gary D. Greenblatt

(57) ABSTRACT

Disclosed are compounds of Formula (I), wherein: X is O or $-NR_3$; $R_1$ is $-CH_2CH_2CH_3$, $-CH_2CF_3$, $-CH_2CH_2CF_3$, $-CH_2CF_2CH_3$, $-CH_2CH_2CH_2CF_3$, $-CH_2CH_2CF_2CH_3$, $-CH_2CH(CH_3)CF_3$, $-CH_2CH_2CH_2F$, or $CH_2(cyclopropyl)$; $R_2$ is $-CH_2CH_2CH_3$, $-CH_2CF_3$, $-CH_2CH_2CF_3$, $-CH_2CF_2CH_3$, $-CH_2CH_2CH_2CF_3$, $-CH_2CH_2CH_2F$, $-CH_2CH(CH_3)CF_3$, $CH_2CH_2CF_2CH_3$, $-CH_2(cyclopropyl)$, $-CH(CH_3)(cyclopropyl)$, phenyl, fluorophenyl, chlorophenyl, trifluorophenyl, methylisoxazolyl, pyridinyl, formula (i), formula (ii), formula (iii), formula (iv) or formula (v); Ring A is phenyl or pyridinyl; and $R_3$, $R_a$, $R_b$, $R_c$, y, and z are defined herein. Also disclosed are methods of using such compounds to inhibit the Notch receptor, and pharmaceutical compositions comprising such compounds. These compounds are useful in treating, preventing, or slowing the progression of diseases or disorders in a variety of therapeutic areas, such as cancer.

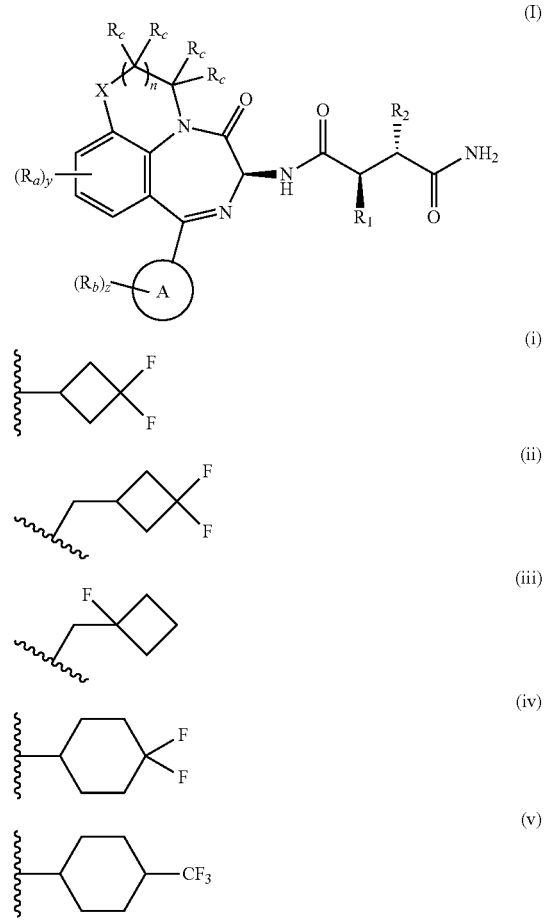

8 Claims, No Drawings

(51) Int. Cl.
*A61K 31/138* (2006.01)
*A61K 31/337* (2006.01)
*A61K 31/506* (2006.01)
*A61K 31/555* (2006.01)
*A61K 31/573* (2006.01)
*A61K 31/5513* (2006.01)
*A61K 31/553* (2006.01)
*A61K 45/06* (2006.01)

(52) U.S. Cl.
CPC .............. *A61K31/506* (2013.01); *A61K 31/553* (2013.01); *A61K 31/555* (2013.01); *A61K 31/5513* (2013.01); *A61K 31/573* (2013.01); *A61K 45/06* (2013.01); *C07D 487/04* (2013.01)

(56) References Cited

U.S. PATENT DOCUMENTS

| | | |
|---|---|---|
| 5,324,726 A | 6/1994 | Bock et al. |
| 5,852,010 A | 12/1998 | Graham et al. |
| 5,998,407 A | 12/1999 | Graham et al. |
| 6,331,408 B1 | 12/2001 | Zaczek et al. |
| 6,495,540 B2 | 12/2002 | Thompson |
| 6,503,901 B1 | 1/2003 | Thompson et al. |
| 6,503,902 B2 | 1/2003 | Olson et al. |
| 6,509,333 B2 | 1/2003 | Olson |
| 6,525,044 B2 | 2/2003 | Olson et al. |
| 6,544,978 B2 | 4/2003 | Wu et al. |
| 6,632,812 B2 | 10/2003 | Han et al. |
| 6,653,303 B1 | 11/2003 | Wu et al. |
| 6,713,476 B2 | 3/2004 | Yang et al. |
| 6,737,038 B1 | 5/2004 | Zaczek et al. |
| 6,756,511 B2 | 6/2004 | Castro Pineiro et al. |
| 6,759,404 B2 | 7/2004 | Olson et al. |
| 6,794,381 B1 | 9/2004 | Olson et al. |
| 6,878,363 B2 | 4/2005 | Zaczek et al. |
| 6,900,199 B2 | 5/2005 | Han et al. |
| 6,958,329 B2 | 10/2005 | Olson |
| 6,960,576 B2 | 11/2005 | Olson et al. |
| 6,962,913 B2 | 11/2005 | Olson et al. |
| 6,984,626 B2 | 1/2006 | Nadin et al. |
| 7,001,901 B2 | 2/2006 | Yang |
| 7,053,081 B2 | 5/2006 | Olson et al. |
| 7,053,084 B1 | 5/2006 | Olson |
| 7,101,870 B2 | 9/2006 | Olson et al. |
| 7,105,509 B2 | 9/2006 | Castro Pineiro et al. |
| 7,112,583 B2 | 9/2006 | Olson et al. |
| 7,125,866 B1 | 10/2006 | Glick et al. |
| 7,153,491 B2 | 12/2006 | Zaczek et al. |
| 7,160,875 B2 | 1/2007 | Flohr et al. |
| 7,276,495 B2 | 10/2007 | Han et al. |
| 7,276,496 B2 | 10/2007 | Olson et al. |
| 7,304,049 B2 | 12/2007 | Olson |
| 7,304,055 B2 | 12/2007 | Olson et al. |
| 7,304,056 B2 | 12/2007 | Olson et al. |
| 7,342,008 B2 | 3/2008 | Olson et al. |
| 7,354,914 B2 | 4/2008 | Olson |
| 7,375,099 B2 | 5/2008 | Galley et al. |
| 7,390,802 B2 | 6/2008 | Han et al. |
| 7,390,896 B2 | 6/2008 | Olson et al. |
| 7,423,033 B2 | 9/2008 | Olson et al. |
| 7,456,172 B2 | 11/2008 | Olson |
| 7,456,278 B2 | 11/2008 | Olson |
| 7,498,324 B2 | 3/2009 | Han et al. |
| 7,528,249 B2 | 5/2009 | Olson et al. |
| 7,544,679 B2 | 6/2009 | Flohr et al. |
| 7,582,624 B2 | 9/2009 | Carter et al. |
| 7,655,647 B2 | 2/2010 | Han et al. |
| 7,718,795 B2 | 5/2010 | Olson |
| 8,629,136 B2 | 1/2014 | Gavai et al. |
| 8,822,454 B2 | 9/2014 | Gavai et al. |
| 8,999,918 B2 | 4/2015 | Gavai et al. |
| 2007/0185094 A1 | 8/2007 | Lattmann et al. |
| 2009/0181944 A1 | 7/2009 | Boylan et al. |
| 2014/0357805 A1 | 12/2014 | Gavai et al. |

FOREIGN PATENT DOCUMENTS

| | | |
|---|---|---|
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2014/047369 | 3/2014 |
| WO | WO 2014/047370 | 3/2014 |
| WO | WO 2014/047374 | 3/2014 |
| WO | WO 2014/047391 | 3/2014 |
| WO | WO 2014/047392 | 3/2014 |
| WO | WO 2014/047393 | 3/2014 |
| WO | WO 2014/047397 | 3/2014 |

OTHER PUBLICATIONS

Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.

Seiffert, D., et al., "Presenilin-1 and -2 are Molecular Targets for gamma-Secretase Inhibitors," The Journal of Biological Chemistry, vol. 275, No. 44, pp. 34086-34091 (2000).

Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).

Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).

Meredith, Jere, "Characterization of APP Activity and Notch Toxicity with gamma-Secretase Inhibitors," 8th International AD/PD Meeting, Salzberg, Austria, Mar. 17, 2007.

Prasad, C.V.C., et al., "Discovery of (S)-2-((S)-2(3,5-difluorophenyl)-2-hydroxyacetamido)-*N*-((S,Z)-3-methyl-4-oxo-4,5-dihydro-3*H*-benzo[*d*][1,2]diazepin-5-yl)propanamide (BMS-433796): A gamma-secretase inhibitor with A beta lowering activity in a transgenic mouse model of Alzheimer's disease," Bioorganic & Medicinal Chemistry Letters 17 pp. 4006-4011 (2007).

Jun, H.T., et al., "Top NOTCH Targets: Notch Signaling in Cancer," Drug Development Research, 69, pp. 319-328 (2008).

Meredith, J.E., et al., gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

PCT/US2013/060831 International Search Report mailed Dec. 10, 2013.

PCT/US2013/060831 Preliminary Report on Patentability issued Mar. 24, 2015.

TRICYCLIC HETEROCYCLE COMPOUNDS

CROSS REFERENCE TO RELATED APPLICATIONS

This application is a national phase application under 35 U.S.C. §371 of International Patent Application No. PCT/US2013/060831, filed Sep. 20, 2013, which claims priority to U.S. Provisional Application 61/703,933, filed Sep. 21, 2012, which are expressly incorporated fully herein by reference.

The present invention generally relates to benzodiazepinone compounds useful as Notch inhibitors. The invention further pertains to pharmaceutical compositions comprising at least one compound according to the invention that is useful for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell*, 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets*, 6:313-323 (2006); Bolos, V. et al., *Endocrine Reviews*, 28:339-363 (2007); Shih, I-M. et al., *Cancer Research*, 67:1879-1882 (2007); Yamaguchi, N. et al., *Cancer Research*, 68:1881-1888 (2008); Miele, L., *Expert Review Anticancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69:319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

Applicants have found potent compounds that have activity as Notch inhibitors. These compounds are provided to be useful as pharmaceuticals with desirable stability, bioavailability, therapeutic index, and toxicity values that are important to their drugability.

SUMMARY OF THE INVENTION

The present invention fills the foregoing need by providing tricyclic heterocycle compounds that are useful as selective inhibitors of Notch signaling pathway.

The present invention also provides pharmaceutical compositions comprising a pharmaceutically acceptable carrier; and at least one compound of Formula (I).

The present invention also provides a method of treating a disease or disorder associated with the activity of the Notch receptor, the method comprising administering to a mammalian patient at least one compound of Formula (I).

The present invention also provides processes and intermediates for making the compounds of Formula (I) and/or prodrugs thereof.

The present invention also provides the compounds of Formula (I) for use in therapy.

The present invention also provides the use of the compounds of Formula (I) for the manufacture of a medicament for the treatment of cancer.

The compounds of Formula (I) and compositions comprising the compounds are Notch inhibitors that may be used in treating, preventing or curing various Notch receptor-related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

DETAILED DESCRIPTION

The first aspect of the present invention provides at least one compound of Formula (I):

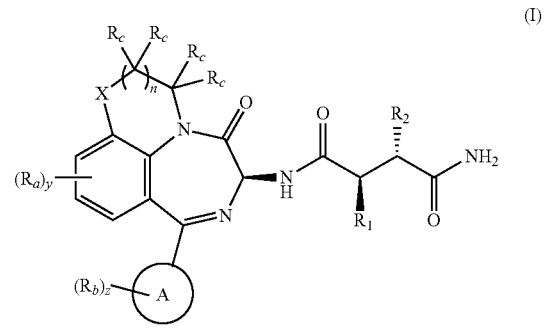

and/or at least one prodrug thereof, wherein:

X is O or —NR$_3$;

R$_1$ is —CH$_2$CH$_2$CH$_3$, —CH$_2$CF$_3$, —CH$_2$CH$_2$CF$_3$, —CH$_2$CF$_2$CH$_3$, —CH$_2$CH$_2$CH$_2$CF$_3$, —CH$_2$CH$_2$CF$_2$CH$_3$, —CH$_2$CH(CH$_3$)CF$_3$, —CH$_2$CH$_2$CH$_2$F, or —CH$_2$(cyclopropyl);

R$_2$ is —CH$_2$CH$_2$CH$_3$, —CH$_2$CF$_3$, —CH$_2$CH$_2$CF$_3$, —CH$_2$CF$_2$CH$_3$, —CH$_2$CH$_2$CH$_2$CF$_3$, —CH$_2$CH$_2$CH$_2$F, —CH$_2$CH(CH$_3$)CF$_3$, —CH$_2$CH$_2$CF$_2$CH$_3$, —CH$_2$(cyclopropyl), —CH(CH$_3$)(cyclopropyl), phenyl, fluorophenyl, chlorophenyl, trifluorophenyl, methylisoxazolyl, pyridinyl,

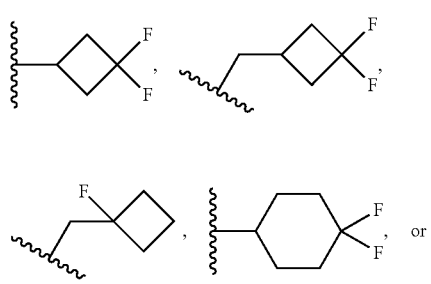

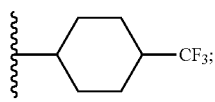

$R_3$ is H, $C_{1-3}$alkyl, —$CH_2CH_2OH$, or —$CH_2CH_2OCH_3$;

Ring A is phenyl or pyridinyl;

each $R_a$ is independently F, Cl, Br, $C_{1-3}$ alkyl, —$CH_2OH$, —$CF_3$, —CN, cyclopropyl, —$OCH_3$, —O(cyclopropyl), —$OCH_2CH_2OCH_3$, and/or

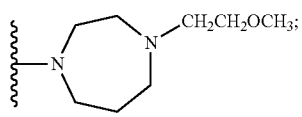

or two adjacent $R_a$ along with the carbon atoms to which they are attached form a dioxole ring;

each $R_b$ is independently F, Cl, —$CH_3$, —$CH_2OH$, —$CH_2F$, —$CF_3$, cyclopropyl, and/or —$OCH_3$;

each $R_c$ is independently H, F, Cl, and/or —$CH_3$;

n is 1 or 2;

y is zero, 1, or 2; and z is zero, 1, or 2.

One embodiment provides at least one compound of Formula (I) wherein X is O, having the structure of Formula (II):

(II)

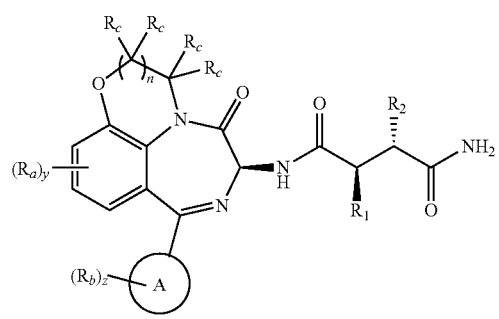

wherein $R_1$, $R_2$, Ring A, $R_a$, $R_b$, $R_c$, n, y, and z are defined in the first aspect. Included in this embodiment are compounds of Formula (IIa):

(IIa)

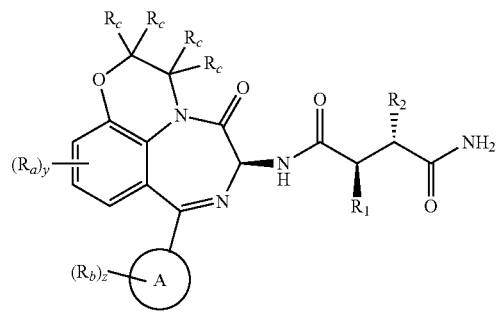

and compounds of Formula (IIb):

(IIb)

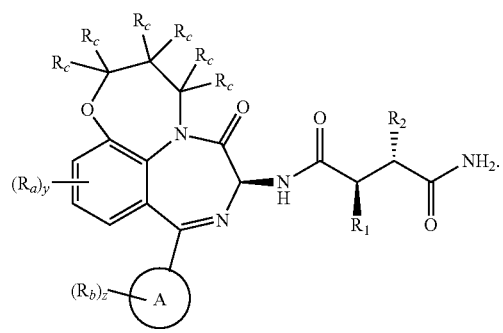

One embodiment provides at least one compound of Formula (I) wherein X is $NR_3$, having the structure of Formula (III):

(III)

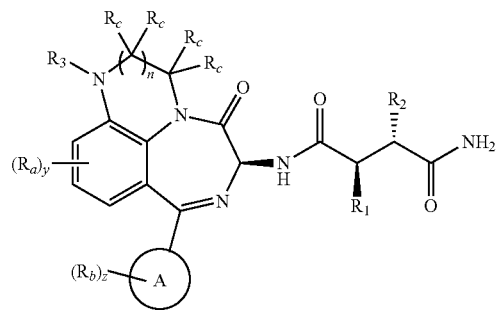

wherein $R_1$, $R_2$, $R_3$, Ring A, $R_a$, $R_b$, $R_c$, n, y, and z are defined in the first aspect. Included in this embodiment are compounds of Formula (IIIa):

(IIIa)

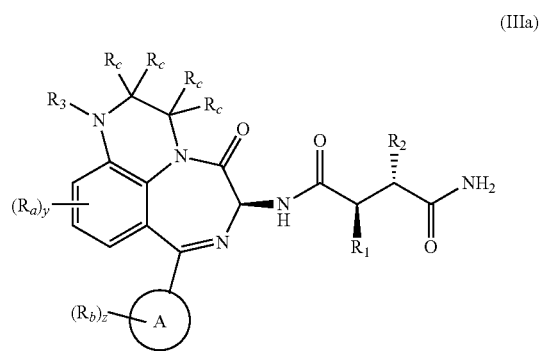

and compounds of Formula (IIIb):

(IIIb)

One embodiment provides at least one compound of Formula (I) wherein Ring A is phenyl; and X, $R_1$, $R_2$, $R_3$, $R_a$, $R_b$, $R_c$, n, y, and z are defined in the first aspect. Included in this embodiment are compounds in which $R_1$ is —$CH_2CH_2CF_3$ or —$CH_2$(cyclopropyl). Also included in this embodiment are compounds in which each $R_c$ is independently H and/or F.

One embodiment provides at least one compound of Formula (I) wherein Ring A is pyridinyl; and X, $R_1$, $R_2$, $R_3$, $R_a$, $R_b$, $R_c$, n, y, and z are defined in the first aspect. Included in this embodiment are compounds in which $R_1$ is —$CH_2CH_2CF_3$ or —$CH_2$(cyclopropyl). Also included in this embodiment are compounds in which each $R_c$ is independently H and/or F.

One embodiment provides at least one compound of Formula (I) wherein $R_1$ is —$CH_2CH_2CH_3$; and X, Ring A, $R_2$, $R_3$, $R_a$, $R_b$, $R_c$, n, y, and z are defined in the first aspect. Included in this embodiment are compounds in which $R_2$ is —$CH_2CH_2CH_3$, —$CH_2CH_2CF_3$, —$CH_2CH_2CH_2F$, —$CH_2$(cyclopropyl), phenyl, or methylisoxazolyl. Also included in this embodiment are compounds in which Ring A is phenyl and $R_2$ is —$CH_2CH_2CF_3$, —$CH_2CH_2CH_2F$, —$CH_2$(cyclopropyl), phenyl, or methylisoxazolyl.

One embodiment provides at least one compound of Formula (I) wherein $R_1$ is —$CH_2CH_2CF_3$; and X, Ring A, $R_2$, $R_3$, $R_a$, $R_b$, $R_c$, n, y, and z are defined in the first aspect. Included in this embodiment are compounds in which $R_2$ is —$CH_2CH_2CH_3$, —$CH_2CH_2CF_3$, —$CH_2CH_2CH_2F$, —$CH_2$(cyclopropyl), phenyl, or methylisoxazolyl. Also included in this embodiment are compounds in which Ring A is phenyl and $R_2$ is —$CH_2CH_2CH_3$, —$CH_2CH_2CF_3$, —$CH_2CH_2CH_2F$, —$CH_2$(cyclopropyl), phenyl, or methylisoxazolyl.

One embodiment provides at least one compound of Formula (I) wherein $R_1$ is —$CH_2$(cyclopropyl); and X, Ring A, $R_2$, $R_3$, $R_a$, $R_b$, $R_c$, n, y, and z are defined in the first aspect. Included in this embodiment are compounds in which $R_2$ is —$CH_2CH_2CH_3$, —$CH_2CH_2CF_3$, —$CH_2CH_2CH_2F$, —$CH_2$(cyclopropyl), phenyl, or methylisoxazolyl. Also included in this embodiment are compounds in which Ring A is phenyl and $R_2$ is —$CH_2CH_2CH_3$, —$CH_2CH_2CF_3$, —$CH_2CH_2CH_2F$, —$CH_2$(cyclopropyl), phenyl, or methylisoxazolyl.

One embodiment provides at least one compound of Formula (I) wherein $R_2$ is —$CH_2CH_2CH_3$; and X, Ring A, $R_1$, $R_3$, $R_a$, $R_b$, $R_c$, n, y, and z are defined in the first aspect. Included in this embodiment are compounds in which $R_1$ is —$CH_2CH_2CH_3$, —$CH_2CH_2CF_3$, or —$CH_2$(cyclopropyl). Also included in this embodiment are compounds in which Ring A is phenyl and $R_1$ is —$CH_2CH_2CF_3$ or —$CH_2$(cyclopropyl).

One embodiment provides at least one compound of Formula (I) wherein $R_2$ is —$CH_2CH_2CF_3$; and X, Ring A, $R_1$, $R_3$, $R_a$, $R_b$, $R_c$, n, y, and z are defined in the first aspect. Included in this embodiment are compounds in which $R_1$ is —$CH_2CH_2CH_3$, —$CH_2CH_2CF_3$, or —$CH_2$(cyclopropyl). Also included in this embodiment are compounds in which Ring A is phenyl and $R_1$ is —$CH_2CH_2CH_3$, —$CH_2CH_2CF_3$, or —$CH_2$(cyclopropyl).

One embodiment provides at least one compound of Formula (I) wherein $R_2$ is —$CH_2CH_2CH_2F$; and X, Ring A, $R_1$, $R_3$, $R_a$, $R_b$, $R_c$, n, y, and z are defined in the first aspect. Included in this embodiment are compounds in which $R_1$ is —$CH_2CH_2CH_3$, —$CH_2CH_2CF_3$, or —$CH_2$(cyclopropyl). Also included in this embodiment are compounds in which Ring A is phenyl and $R_1$ is —$CH_2CH_2CH_3$, —$CH_2CH_2CF_3$, or —$CH_2$(cyclopropyl).

One embodiment provides at least one compound of Formula (I) wherein $R_2$ is —$CH_2$(cyclopropyl); and X, Ring A, $R_1$, $R_3$, $R_a$, $R_b$, $R_c$, n, y, and z are defined in the first aspect. Included in this embodiment are compounds in which $R_1$ is —$CH_2CH_2CH_3$, —$CH_2CH_2CF_3$, or —$CH_2$(cyclopropyl). Also included in this embodiment are compounds in which Ring A is phenyl and $R_1$ is —$CH_2CH_2CH_3$, —$CH_2CH_2CF_3$, or —$CH_2$(cyclopropyl).

One embodiment provides at least one compound of Formula (I) wherein $R_2$ is phenyl; and X, Ring A, $R_1$, $R_3$, $R_a$, $R_b$, $R_c$, n, y, and z are defined in the first aspect. Included in this embodiment are compounds in which $R_1$ is —$CH_2CH_2CH_3$, —$CH_2CH_2CF_3$, or —$CH_2$(cyclopropyl). Also included in this embodiment are compounds in which Ring A is phenyl and $R_1$ is —$CH_2CH_2CH_3$, —$CH_2CH_2CF_3$, or —$CH_2$(cyclopropyl).

One embodiment provides at least one compound of Formula (I) wherein $R_2$ is methylisoxazolyl; and X, Ring A, $R_1$, $R_3$, $R_a$, $R_b$, $R_c$, n, y, and z are defined in the first aspect. Included in this embodiment are compounds in which $R_1$ is —$CH_2CH_2CH_3$, —$CH_2CH_2CF_3$, or —$CH_2$(cyclopropyl). Also included in this embodiment are compounds in which Ring A is phenyl and $R_1$ is —$CH_2CH_2CH_3$, —$CH_2CH_2CF_3$, or —$CH_2$(cyclopropyl).

One embodiment provides at least one compound of Formula (I) having the structure:

wherein X, $R_1$, $R_2$, Ring A, $R_a$, $R_b$, $R_c$, y, and z are defined in the first aspect. Included in this aspect are compounds in which each $R_c$ is independently H and/or F; and Ring A is phenyl. Also included in this aspect are compounds in which each $R_c$ is H; Ring A is phenyl; $R_1$ is —$CH_2CH_2CH_3$, —$CH_2CH_2CF_3$, or —$CH_2$(cyclopropyl); and $R_2$ is —$CH_2CH_2CH_3$, —$CH_2CH_2CF_3$, —$CH_2CH_2CH_2F$, —$CH_2$(cyclopropyl), phenyl, or methylisoxazolyl.-

One embodiment provides at least one compound of Formula (I) having the structure:

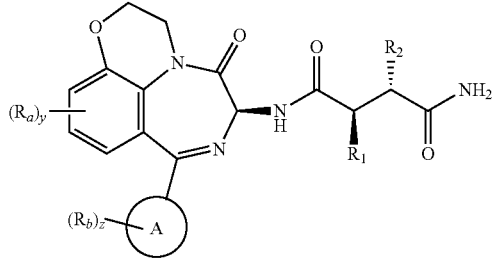

wherein $R_1$, $R_2$, Ring A, $R_a$, $R_b$, y, and z are defined in the first aspect. Included in this aspect are compounds in which Ring A is phenyl. Also included in this aspect are compounds in which Ring A is phenyl; $R_1$ is —$CH_2CH_2CH_3$, —$CH_2CH_2CF_3$, or —$CH_2$(cyclopropyl); and $R_2$ is —$CH_2CH_2CH_3$, —$CH_2CH_2CF_3$, —$CH_2CH_2F$, —$CH_2$(cyclopropyl), phenyl, or methylisoxazolyl. This embodiment further includes compounds in which Ring A is phenyl, $R_1$ is —$CH_2CH_2CH_3$, —$CH_2CH_2CF_3$, or —$CH_2$(cyclopropyl); $R_2$ is —$CH_2CH_2CH_3$, —$CH_2CH_2CF_3$, —$CH_2CH_2F$, —$CH_2$(cyclopropyl), phenyl, or methylisoxazolyl; y is zero; and z is zero or 1.

One embodiment provides at least one compound of Formula (I) having the structure:

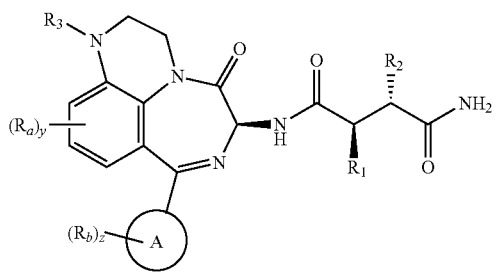

wherein $R_1$, $R_2$, $R_3$, Ring A, $R_a$, $R_b$, y, and z are defined in the first aspect. Included in this aspect are compounds in which Ring A is phenyl and $R_3$ is H, —$CH_3$, —$CH_2CH_2OH$, or —$CH_2CH_2OCH_3$. Also included in this aspect are compounds in which Ring A is phenyl; $R_1$ is —$CH_2CH_2CH_3$, —$CH_2CH_2CF_3$, or —$CH_2$(cyclopropyl); $R_2$ is —$CH_2CH_2CH_3$, —$CH_2CH_2CF_3$, —$CH_2CH_2F$, —$CH_2$(cyclopropyl), phenyl, or methylisoxazolyl; and $R_3$ is H or —$CH_2CH_2OCH_3$. This embodiment further includes compounds in which Ring A is phenyl, $R_1$ is —$CH_2CH_2CH_3$, —$CH_2CH_2CF_3$, or —$CH_2$(cyclopropyl); $R_2$ is —$CH_2CH_2CH_3$, —$CH_2CH_2CF_3$, —$CH_2CH_2F$, —$CH_2$(cyclopropyl), phenyl, or methylisoxazolyl; $R_3$ is H or —$CH_2CH_2OCH_3$; y is zero; and z is zero or 1.

One embodiment provides at least one compound of Formula (IIb) having the structure:

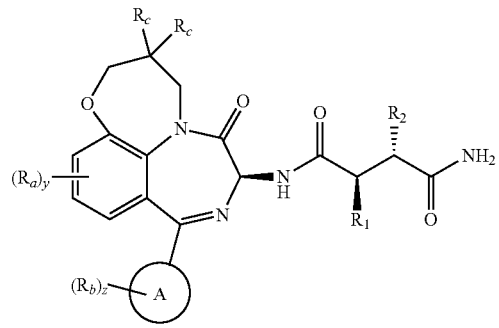

wherein $R_1$, $R_2$, Ring A, $R_a$, $R_b$, $R_c$, y, and z are defined in the first aspect. Included in this embodiment are compounds in which each $R_c$ is independently H and/or F; and Ring A is phenyl. Also included in this embodiment are compounds in which each $R_c$ is independently H and/or F; Ring A is phenyl; $R_1$ is —$CH_2CH_2CH_3$, —$CH_2CH_2CF_3$, or —$CH_2$(cyclopropyl); and $R_2$ is —$CH_2CH_2CH_3$, —$CH_2CH_2CF_3$, —$CH_2CH_2F$, —$CH_2$(cyclopropyl), phenyl, or methylisoxazolyl.

One embodiment provides at least one compound of Formula (I) wherein y is zero or 1; and $R_1$, $R_2$, $R_3$, Ring A, $R_a$, $R_b$, $R_c$, and z are defined in the first aspect. Included in this embodiment are compounds in which $R_a$ is F, Cl, —$CH_3$, —$CH_2OH$, —$OCH_3$, cyclopropyl, or —$CH_2$(cyclopropyl). Also included in this embodiment are compounds in which $R_a$ is F, Cl, —$CH_3$, or —$CH_2OH$; and z is zero or 1.

One embodiment provides at least one compound of Formula (I) wherein $R_1$ is —$CH_2CH_2CH_3$, —$CH_2CH_2CF_3$, or —$CH_2$(cyclopropyl); $R_2$ is —$CH_2CH_2CH_3$, —$CH_2CH_2CF_3$, —$CH_2CH_2F$, —$CH_2$(cyclopropyl), phenyl, or methylisoxazolyl; $R_3$ is H or —$CH_2CH_2OCH_3$; Ring A is phenyl; $R_b$ is Cl or —$CH_3$; each $R_c$ is independently H and/or F; y is zero; z is zero or 1; and X and n are defined in the first aspect.

One embodiment provides at least one compound of Formula (I) having the structure:

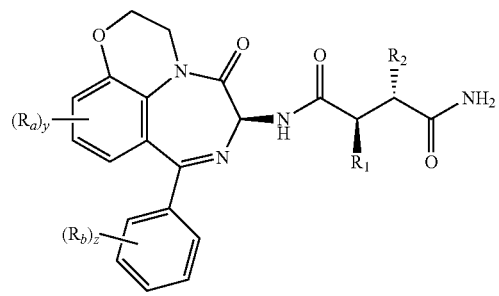

wherein $R_1$, $R_2$, $R_a$, $R_b$, y, and z are defined in the first aspect. Included in this aspect are compounds in which $R_1$ is —$CH_2CH_2CH_3$, —$CH_2CH_2CF_3$, or —$CH_2$(cyclopropyl); and $R_2$ is —$CH_2CH_2CH_3$, —$CH_2CH_2CF_3$, —$CH_2CH_2F$, —$CH_2$(cyclopropyl), phenyl, or methylisoxazolyl. Also included in this embodiment are compounds selected from:

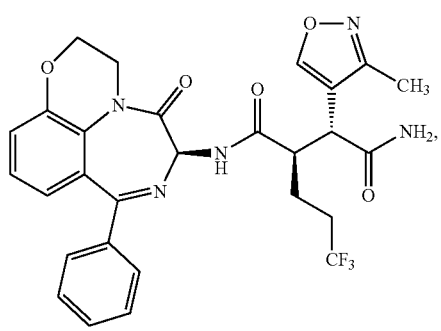
(4)
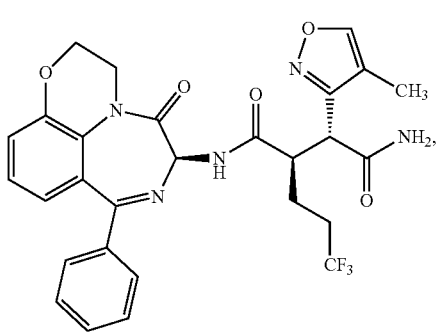
(9)
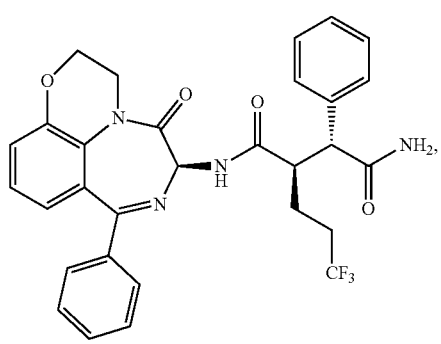
(5)
(6)
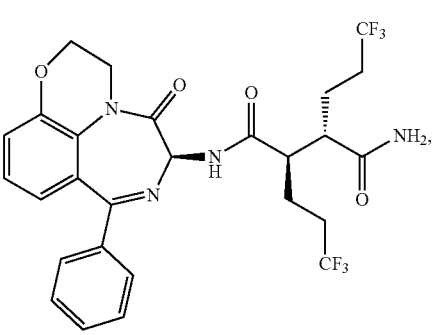
(10)
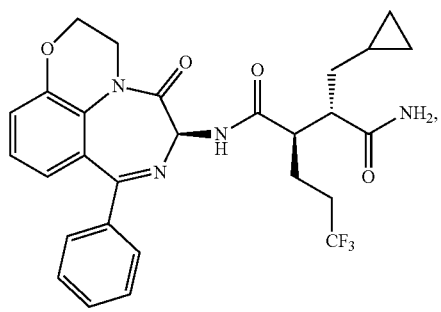
(7)
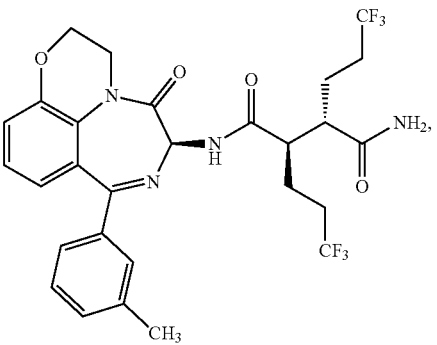
(11)
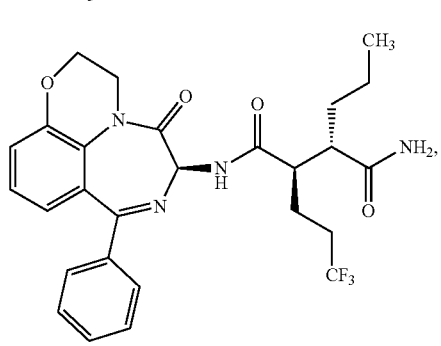
(8)
(12)

(13)
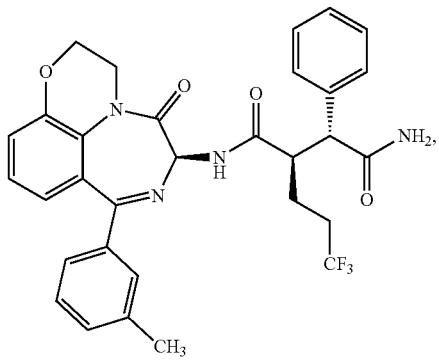

(14)
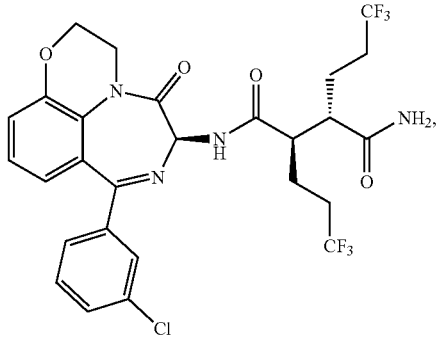

(15)
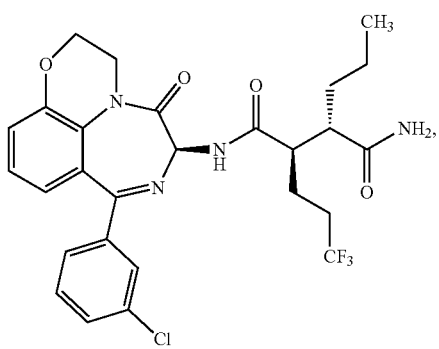

(16)
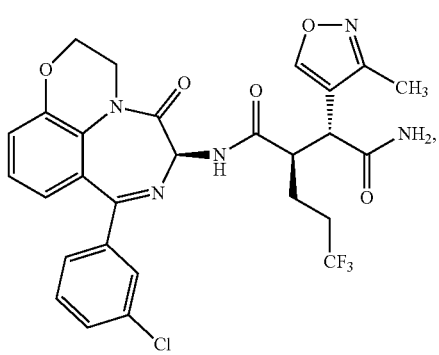

(17)
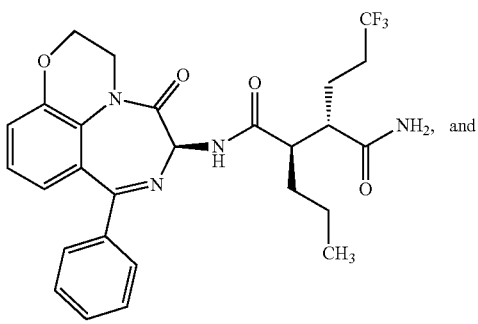

(18)
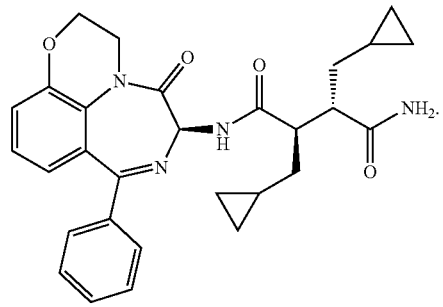

One embodiment provides at least one compound of Formula (I) having the structure:

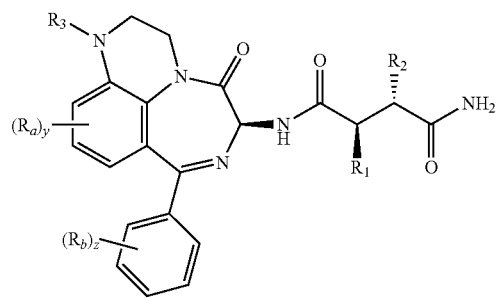

wherein $R_1$, $R_2$, $R_3$, $R_a$, $R_b$, y, and z are defined in the first aspect. Included in this aspect are compounds in which $R_1$ is —CH$_2$CH$_2$CH$_3$, —CH$_2$CH$_2$CF$_3$, or —CH$_2$(cyclopropyl); and $R_2$ is —CH$_2$CH$_2$CH$_3$, —CH$_2$CH$_2$CF$_3$, —CH$_2$CH$_2$CH$_2$F, —CH$_2$(cyclopropyl), phenyl, or methylisoxazolyl. Also included in this embodiment are compounds selected from:

(24)
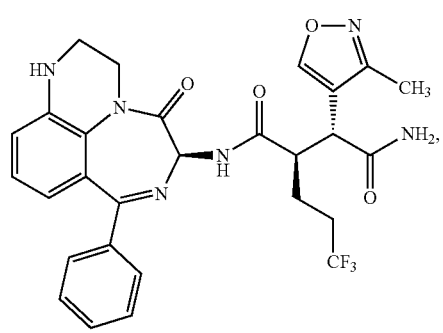

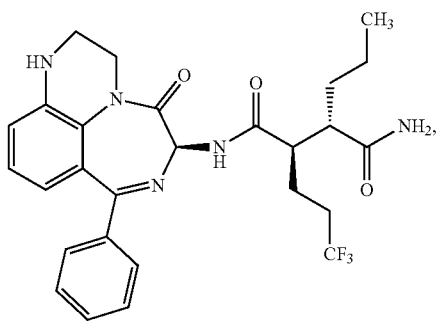
(25)

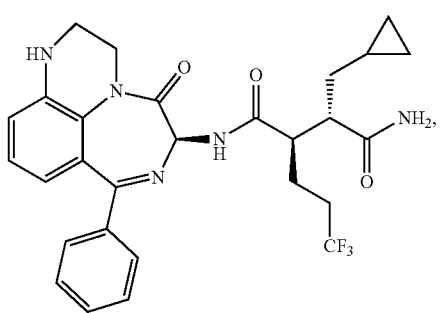
(26)

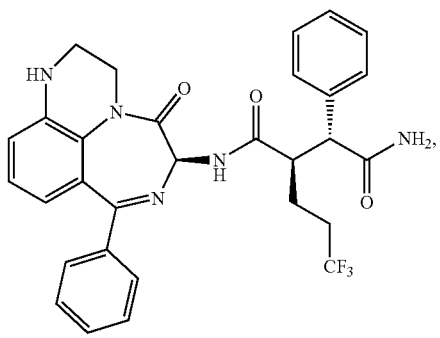
(27)

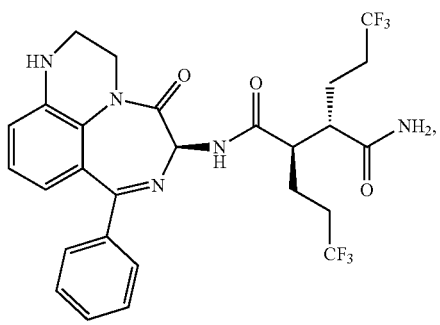
(28)

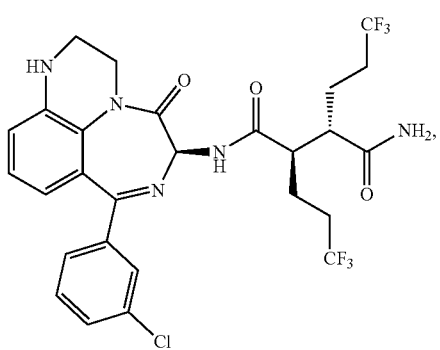
(29)

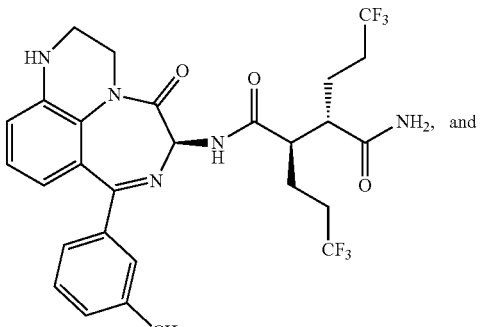
(30)

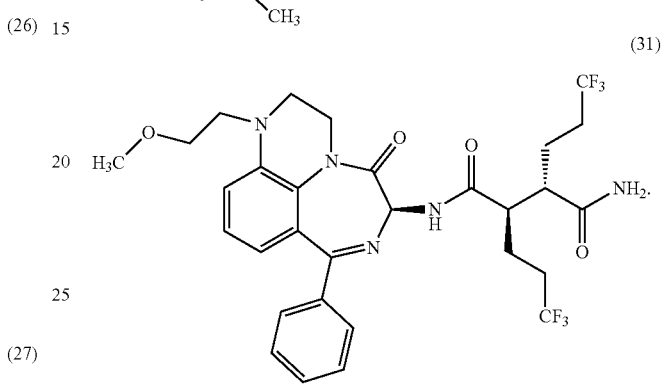
(31)

One embodiment provides at least one compound of Formula (I) having the structure:

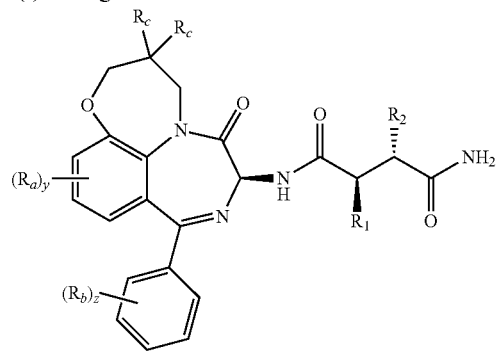

wherein $R_1$, $R_2$, $R_3$, $R_a$, $R_b$, $R_c$, y, and z are defined in the first aspect. Included in this aspect are compounds in which $R_1$ is —CH$_2$CH$_2$CH$_3$, —CH$_2$CH$_2$CF$_3$, or —CH$_2$(cyclopropyl); $R_2$ is —CH$_2$CH$_2$CH$_3$, —CH$_2$CH$_2$CF$_3$, —CH$_2$CH$_2$CH$_2$F, —CH$_2$(cyclopropyl), phenyl, or methylisoxazolyl; and each $R_c$ is independently H and/or F. Also included in this embodiment are compounds selected from:

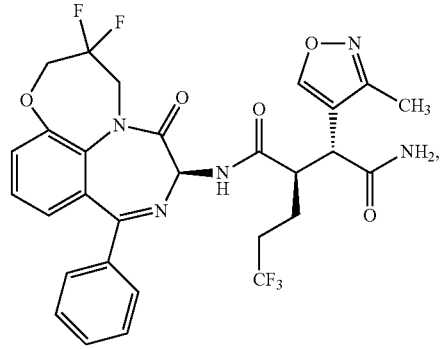
(1)

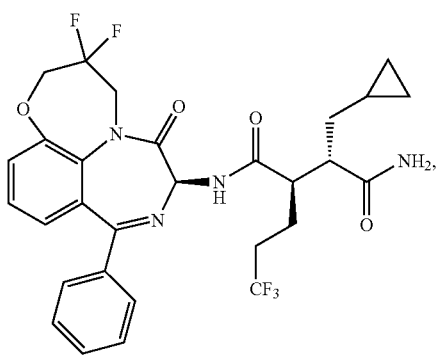
(2)

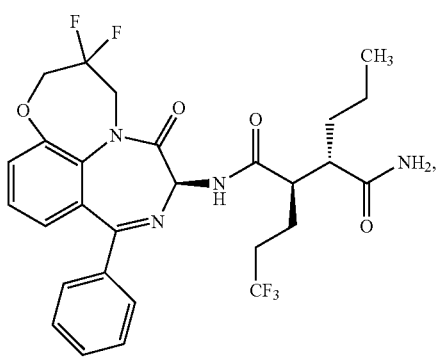
(3)

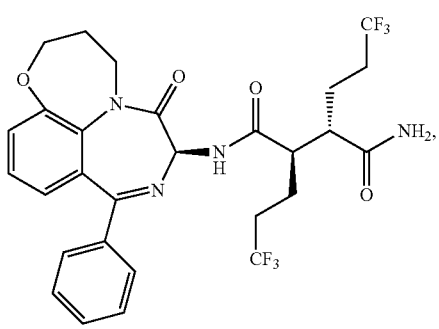
(19)

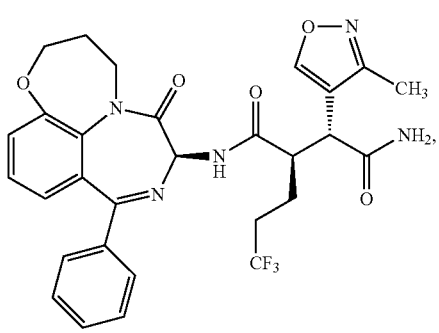
(20)

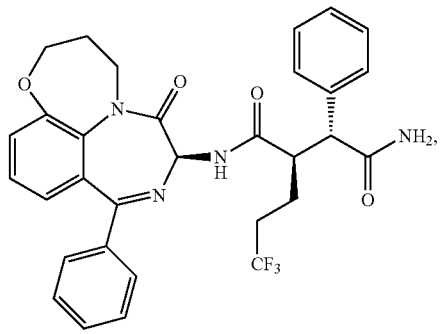
(21)

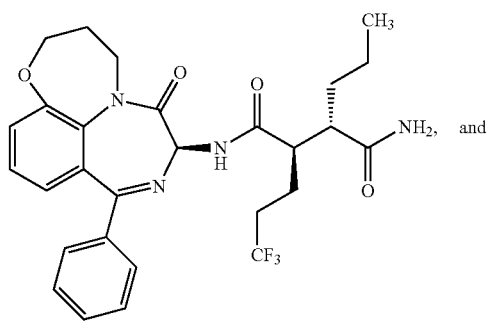
(22)

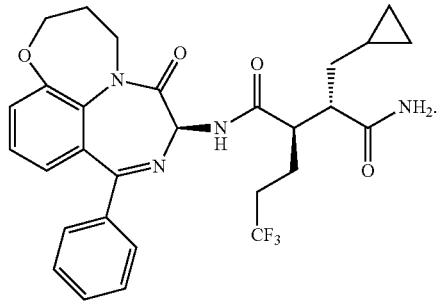
(23)

One embodiment provides a compound of Formula (I) selected from: (2R,3R)—N-((7S)-3,3-difluoro-6-oxo-9-phenyl-3,4,6,7-tetrahydro-2H-[1,4]diazepino[1,7,6-ef][1,5]benzoxazepin-7-yl)-3-(3-methyl-4-isoxazolyl)-2-(3,3,3-trifluoropropyl)succinamide (1); (2R,3S)-3-(cyclopropylmethyl)-N-((7S)-3,3-difluoro-6-oxo-9-phenyl-3,4,6,7-tetrahydro-2H-[1,4]diazepino[1,7,6-ef][1,5]benzoxazepin-7-yl)-2-(3,3,3-trifluoropropyl)succinamide (2); (2R,3S)—N-((7S)-3,3-difluoro-6-oxo-9-phenyl-3,4,6,7-tetrahydro-2H-[1,4]diazepino[1,7,6-ef][1,5]benzoxazepin-7-yl)-3-propyl-2-(3,3,3-trifluoropropyl)succinamide (3); (2R,3R)-3-(3-methyl-4-isoxazolyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl)succinamide (4); (2R,3R)—N-((6S)-5-oxo-8-phenyl-2,3,5,6-tetrahydro[1,4]oxazino[2,3,4-jk][1,4]benzodiazepin-6-yl)-3-phenyl-2-(3,3,3-trifluoropropyl)succinamide (5); (2R,3S)-3-(cyclopropylmethyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl)succinamide (6); (2R,3S)—N-((6S)-5-oxo-8-phenyl-2,3,5,6-tetrahydro[1,4]oxazino[2,3,4-jk][1,4]benzodiazepin-6-yl)-3-propyl-2-(3,3,3-trifluoropropyl)succinamide (7); (2R,3S)-3-(3-fluoropropyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl)succinamide (8); (2R,3R)-3-(4-methyl-3- isoxazolyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl)succinamide (9); (2R,3S)—N-((6S)-5-oxo-8-phenyl-2,3,5,6-tetrahydro[1,4]oxazino[2,3,4-jk][1,4]benzodiazepin-6-yl)-2,3-bis(3,3,3-trifluoropropyl)succinamide (10); (2R,3S)—N-((6S)-8-(3-methylphenyl)-5-oxo-2,3,5,6-tetrahydro[1,4]oxazino[2,3,4-jk][1,4]benzodiazepin-6-yl)-2,3-bis(3,3,3-trifluoropropyl)succinamide (11); (2R,3S)—N-((6S)-8-(3-methylphenyl)-5-oxo-2,3,5,6-tetrahydro[1,4]oxazino[2,3,4-jk][1,4]benzodiazepin-6-yl)-3-propyl-2-(3,3,3-trifluoropropyl)succinamide (12); (2R,3R)—N-((6S)-8-(3-methylphenyl)-5-oxo-2,3,5,6-tetrahydro[1,4]oxazino[2,3,4-jk][1,4]benzodiazepin-6-yl)-3-phenyl-2-(3,3,3-trifluoropropyl)succinamide (13); (2R,3S)—N-((6S)-8-(3-chlorophenyl)-5-oxo-2,3,5,6-tetrahydro[1,4]oxazino[2,3,4-jk][1,4]benzodiazepin-6-yl)-2,3-bis(3,3,3-trifluoropropyl)succinamide (14); (2R,3S)—N-((6S)-8-(3-chlorophenyl)-5-oxo-2,3,5,6-tetrahydro[1,4]oxazino[2,3,4-jk][1,4]benzodiazepin-6-yl)-3-propyl-2-(3,3,3-trifluoropropyl)succinamide (15); (2R,3R)—N-((6S)-8-(3-chlorophenyl)-5-oxo-2,3,5,6-tetrahydro[1,4]oxazino[2,3,4-jk][1,4]benzodiazepin-6-yl)-3-(3-methyl-4-isoxazolyl)-2-(3,3,3-trifluoropropyl)succinamide (16); (2R,3S)—N-((6S)-5-oxo-8-phenyl-2,3,5,6-tetrahydro[1,4]oxazino[2,3,4-jk][1,4]benzodiazepin-6-yl)-2-propyl-3-(3,3,3-trifluoropropyl)succinamide (17); (2R,3S)-2,3-bis(cyclopropylmethyl)-N-((6S)-5-oxo-8-phenyl-2,3,5,6-tetrahydro[1,4]oxazino[2,3,4-jk][1,4]benzodiazepin-6-yl)succinamide (18); (2R,3S)—N-((7S)-6-oxo-9-phenyl-3,4,6,7-tetrahydro-2H-[1,4]diazepino[1,7,6-ef][1,5]benzoxazepin-7-yl)-2,3-bis(3,3,3-trifluoropropyl)succinamide (19); (2R,3R)-3-(3-methyl-4-isoxazolyl)-N-((7S)-6-oxo-9-phenyl-3,4,6,7-tetrahydro-2H-[1,4]diazepino[1,7,6-ef][1,5]benzoxazepin-7-yl)-2-(3,3,3-trifluoropropyl)succinamide (20); (2R,3R)—N-((7S)-6-oxo-9-phenyl-3,4,6,7-tetrahydro-2H-[1,4]diazepino[1,7,6-ef][1,5]benzoxazepin-7-yl)-3-phenyl-2-(3,3,3-trifluoropropyl)succinamide (21); (2R,3S)—N-((7S)-6-oxo-9-phenyl-3,4,6,7-tetrahydro-2H-[1,4]diazepino[1,7,6-ef][1,5]benzoxazepin-7-yl)-3-propyl-2-(3,3,3-trifluoropropyl)succinamide (22); (2R,3S)-3-(cyclopropylmethyl)-N-((7S)-6-oxo-9-phenyl-3,4,6,7-tetrahydro-2H-[1,4]diazepino[1,7,6-ef][1,5]benzoxazepin-7-yl)-2-(3,3,3-trifluoropropyl)succinamide (23); (2R,3R)-3-(3-methyl-4-isoxazolyl)-N-((6S)-5-oxo-8-phenyl-2,3,5,6-tetrahydro-1H-[1,4]diazepino[1,7,6-de]quinoxalin-6-yl)-2-(3,3,3-trifluoropropyl)succinamide (24); (2R,3S)—N-((6S)-5-oxo-8-phenyl-2,3,5,6-tetrahydro-1H-[1,4]diazepino[1,7,6-de]quinoxalin-6-yl)-3-propyl-2-(3,3,3-trifluoropropyl)succinamide (25); (2R,3S)-3-(cyclopropylmethyl)-N-((6S)-5-oxo-8-phenyl-2,3,5,6-tetrahydro-1H-[1,4]diazepino[1,7,6-de]quinoxalin-6-yl)-2-(3,3,3-trifluoropropyl)succinamide (26); (2R,3R)—N-((6S)-5-oxo-8-phenyl-2,3,5,6-tetrahydro-1H-[1,4]diazepino[1,7,6-de]quinoxalin-6-yl)-3-phenyl-2-(3,3,3-trifluoropropyl)succinamide (27); (2R,3S)—N-((6S)-5-oxo-8-phenyl-2,3,5,6-tetrahydro-1H-[1,4]diazepino[1,7,6-de]quinoxalin-6-yl)-2,3-bis(3,3,3-trifluoropropyl)succinamide (28); (2R,3S)—N-((6S)-8-(3-chlorophenyl)-5-oxo-2,3,5,6-tetrahydro-1H-[1,4]diazepino[1,7,6-de]quinoxalin-6-yl)-2,3-bis(3,3,3-trifluoropropyl)succinamide (29); (2R,3S)—N-((6S)-8-(3-methylphenyl)-5-oxo-2,3,5,6-tetrahydro-1H-[1,4]diazepino[1,7,6-de]quinoxalin-6-yl)-2,3-bis(3,3,3-trifluoropropyl)succinamide (30); and (2R,3S)—N-((6S)-1-(2-methoxyethyl)-5-oxo-8-phenyl-2,3,5,6-tetrahydro-1H-[1,4]diazepino[1,7,6-de]quinoxalin-6-yl)-2,3-bis(3,3,3-trifluoropropyl)succinamide (31).

One embodiment provides at least one compound of Formula (I) having a metabolic half life value of at least 45 minutes as measured in the human metabolic stability half-life assay described herein.

One embodiment provides at least one compound of Formula (I) having a metabolic half life value of at least 60 minutes as measured in the human metabolic stability half-life assay described herein.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art, ⊰ is used in structural formulas herein to depict the bond that is the point of attachment of the moiety or substituent to the core or backbone structure.

The terms "halo" and "halogen", as used herein, refer to F, Cl, Br, or I.

The term "alkyl" as used herein, refers to both branched and straight chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

The compound of Formula (I) is intended to include solvates of compounds of Formula (I).

Any compound that can be converted in vivo to provide the bioactive agent (i.e., the compound of Formula (I)) is a prodrug within the scope and spirit of the invention.

Various forms of prodrugs are well known in the art and are described in:
a) Wermuth, C. G. et al., *The Practice of Medicinal Chemistry*, Chapter 31, Academic Press (1996);
b) Bundgaard, H. ed., *Design of Prodrugs*, Elsevier (1985);
c) Bundgaard, H., Chapter 5, "Design and Application of Prodrugs", Krogsgaard-Larsen, P. et al., eds., *A Textbook of Drug Design and Development*, pp. 113-191, Harwood Academic Publishers (1991); and
d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising at least one compound of Formula (I); and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art.

The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise the compound of Formula (I), or a prodrug thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

UTILITY

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof a compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of at least one compound of Formula (I) in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment at least one compound of Formula (I) for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient at least one compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof at least one compound of Formula (I); and administering one or more additional anticancer agents.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of at least one compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of at least one compound of Formula (I); and one or more additional agents in kit form, e.g., where they are packaged together or placed in separate packages to be sold together as a kit, or where they are packaged to be formulated together.

In one embodiment, a method is provided for treating cancer comprising administering to a mammal in need thereof at least one compound of Formula (I); administering dasatinib; and optionally, one or more additional anticancer agents.

In one embodiment, a method is provided for treating cancer comprising administering to a mammal in need thereof at least one compound of Formula (I) administering paclitaxel; and optionally, one or more additional anticancer agents.

In one embodiment, a method is provided for treating cancer comprising administering to a mammal in need thereof at least one compound of Formula (I) administering tamoxifen; and optionally, one or more additional anticancer agents.

In one embodiment, a method is provided for treating cancer comprising administering to a mammal in need thereof at least one compound of Formula (I) administering a glucocorticoid; and optionally, one or more additional anticancer agents. An example of a suitable glucocorticoid is dexamethasone.

In one embodiment, a method is provided for treating cancer comprising administering to a mammal in need thereof at least one compound of Formula (I) administering carboplatin; and optionally, one or more additional anticancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising at least one compound of Formula (I); one or more additional agents selected from a kinase inhibitory agent (small molecule, polypeptide, and antibody), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the at least one compound of Formula (I) is administered continuously to a patient in need thereof, one or more times daily. For example, a therapeutically effective amount of the compound of Formula (I) is administered to a patient in need thereof, one or more times daily for continuous days.

In one embodiment, the at least one compound of Formula (I) is administered intermittently to a patient in need thereof, one or more times daily. For example, a therapeutically effective amount of the compound of Formula (I) is administered to a patient in need thereof, one or more times daily according to an intermittent schedule.

In one embodiment, the at least one compound of Formula (I) is administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, the at least one compound of Formula (I) is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, at least one compound of Formula (I) is administered on one day, followed by 6 days of rest, and repeated on a weekly schedule.

In one embodiment, at least one compound of Formula (I) is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, at least one compound of Formula (I) is administered on two consecutive days, followed by 5 days of rest, and repeated on a weekly schedule.

In one embodiment, at least one compound of Formula (I) is administered on three consecutive days followed by four days of rest, and repeated on a weekly schedule.

In one embodiment, at least one compound of Formula (I) is administered on one day, followed by 10 to 13 days of rest.

In one embodiment, at least one compound of Formula (I) is administered once each day (QD). This embodiment include once daily oral administration.

In one embodiment, at least one compound of Formula (I) is administered twice each day (BID). This embodiment include twice daily oral administration.

In one embodiment, at least one compound of Formula (I) is administered on alternate days: one day on followed by one day of rest. This two day cycle can be repeated one or more times.

METHODS OF PREPARATION

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 8. The synthesis of aminobenzophenone intermediate iv may be accomplished by several methods skilled to one in the art, summarized in Schemes 1 to 2.

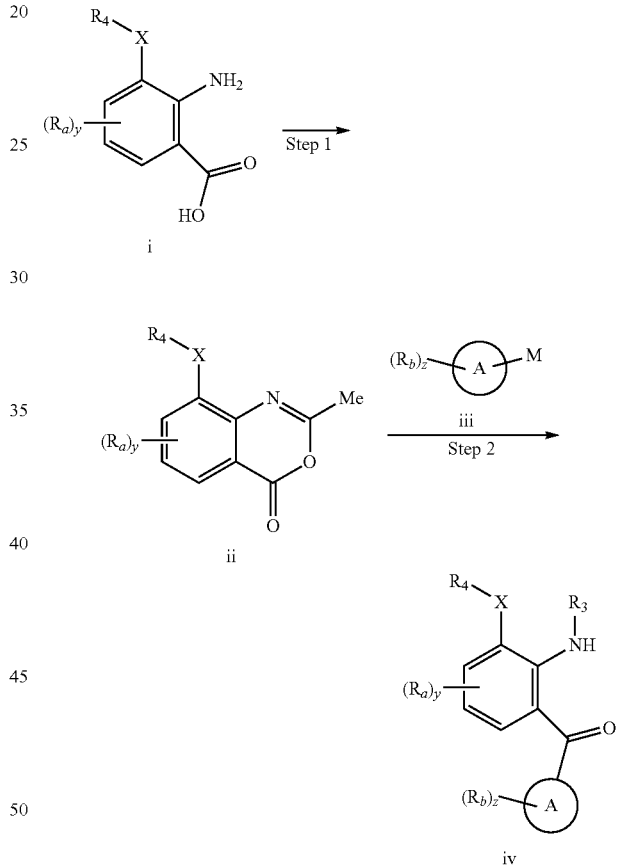

Step 1 of Scheme 1 may be accomplished by treatment of a suitably functionalized anthranilic acid i, readily available to one skilled in the art, with acetic anhydride at a suitable temperature, such as 180° C., to give intermediate ii.

Step 2: Intermediate ii may be transformed to aminobenzophenone iv by treatment with a functionalized organometallic reagent iii. For example, intermediate ii may be treated with a Grignard reagent iii (M=MgBr) in a solvent such as diethyl ether to give acetylated aminobenzophenone iv ($R_3$=Ac). The acetyl group may then be removed by many methods known to one skilled in the art, such as treatment with HCl in a solvent such as ethanol at a suitable temperature, such as 100° C., to give aminobenzophenone iv.

Scheme 2

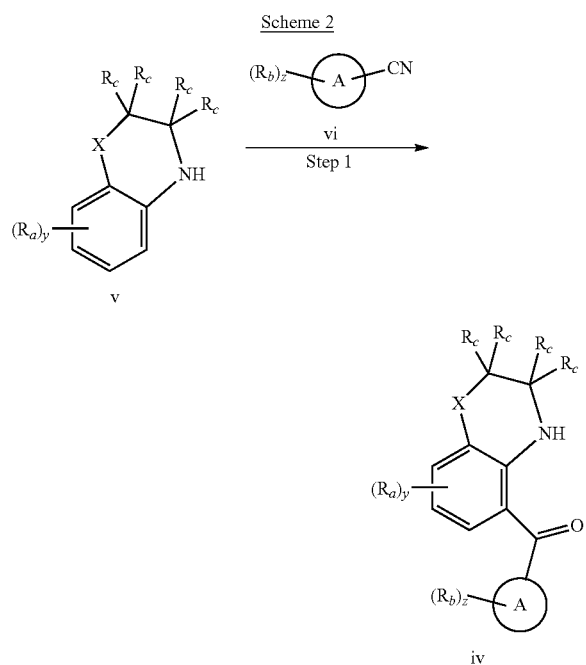

Step 1 of Scheme 2 may be accomplished by a number of methods known to one skilled in the art. For example, treatment of a suitably functionalized aniline v, readily available to one skilled in the art, with a suitable Lewis acid such as boron trichloride, followed by treatment with another Lewis acid, such as aluminum trichloride, and a suitably functionalized nitrile vi in an appropriate solvent such as toluene at an appropriate temperature such as 60° C. gives an imine intermediate, which forms aminobenzophenone iv upon treatment under appropriate hydrolysis conditions, such as treatment with hydrochloric acid.

Scheme 3

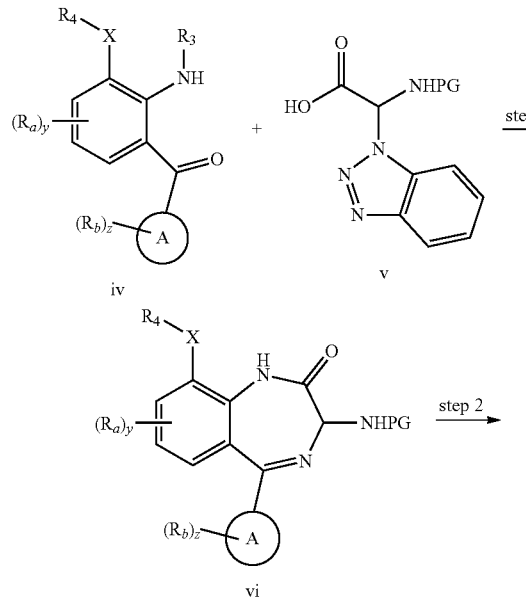

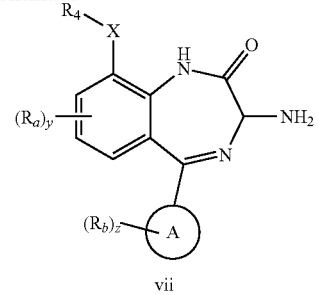

The preparation of benzodiazepinone (vii) may be accomplished in multitude of methods known to one skilled in the art. For example, as shown in Scheme 3, an appropriately substituted 2-aminobenzophenone (iv) (for example, from Walsh, D. A., *Synthesis*, 677 (1980); and references cited therein, or other methods known to one skilled in the art) may be coupled to the protected glycine derivative (v) (PG=protecting group, for example PG=CBz, see Katritzky, A. R. et al., *Org. Chem.*, 55:2206-2214 (1990)), treated with a reagent such as ammonia and subjected to cyclization to afford the benzodiazepinone (vi), according to the procedure outlined in the literature (for example Sherrill, R. G. et al., *J. Org. Chem.*, 60:730 (1995); or other routes known to one skilled in the art). The resulting racemic mixture may be separated (using procedures known to one skilled in the art) to get the individual enantiomers, or used as a racemate.

Step 2: The deprotection of (vi) may be accomplished in several ways known to one skilled in the art. For example, with PG=CBz, Compound (vi) may be treated with a reagent such as HBr in a solvent such as AcOH. Compound (vii) may be used as a racemate. Alternatively, compound (vii) may be subjected to enantiomeric resolution using standard methods (e.g., chiral preparative chromatography).

Scheme 4

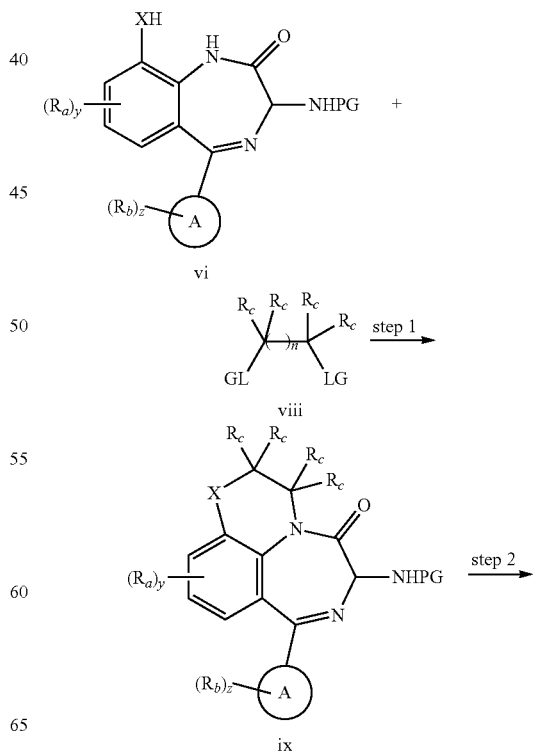

33

-continued

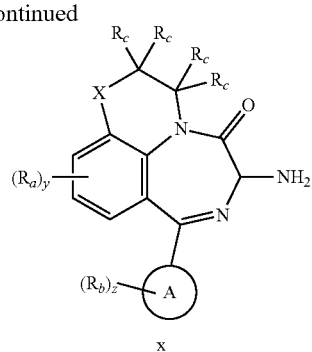

x

The preparation of tricyclic benzodiazepinone (x) may be accomplished in multitude of methods known to one skilled in the art. For example, as shown in Scheme 4.

Step 1: An appropriately substituted benzodiazepinone (vi) may be coupled to (viii) bearing two suitable leaving groups. For example, with LG=Br, in the presence of a base such as $Cs_2CO_3$ in a solvent such as DMF, at room temperature under an inert atmosphere such as $N_2$ to afford (ix).

Step 2: The deprotection of (ix) may be accomplished in several ways known to one skilled in the art. For example, with PG=Boc, Compound (ix) may be treated with a reagent such as TFA in a solvent such as $CH_2Cl_2$ to give x. Compound (x) may be used as a racemate. Alternatively, compound (x) may be subjected to enantiomeric resolution using standard methods (e.g., chiral preparative chromatography).

34

Step 1: The first step of Scheme 5 is accomplished by converting compound (xi) to the ester (xiii), employing one of the multiple ways known to one skilled in the art, such as treatment with a substituted acetimidate such as compound (xii) in the presence of a reagent such as boron trifluoride etherate at an appropriate temperature in a solvent such as THF.

Step 2: Acid (xiv) can be converted to compound (xv) in multiple ways known to one skilled in the art. For example, treatment of acid (xiv) with a reagent such as oxalyl chloride in a solvent such as DCM gives the acid chloride (xv, X=Cl). Compound (xv) can be treated with an oxazolidinone (xvi) under standard conditions to give compound (xvii) (Evans, D. A. et al., *J. Am. Chem Soc.*, 112:4011 (1990)).

Step 3: Compound (xvii) can be converted to compound (xviii) in multiple ways (Baran, P. et al., *J. Am. Chem. Soc.*, 130(34):11546 (2008)). For example, compound (xiii) is treated with a base such as LDA in a solvent such as toluene, at low temperature such as −78° C. under an inert atmosphere such as $N_2$. The resulting mixture is added to a solution of compound (xvii) treated with lithium chloride and a base such as LDA in a solvent such as toluene under an inert atmosphere such as $N_2$. To the resulting mixture of the enolates of compounds (xiii) and (xvii) is added bis(2-ethylhexanoyloxy) copper at a low temperature such as −78° C. under an inert atmosphere such as $N_2$ and warmed to room temperature to provide compound (xviii).

Step 4: Conversion of compound (xviii) to (xix) may be accomplished by treating it with hydrogen peroxide and lithium hydroxide at an appropriate temperature using a mix- Scheme 5

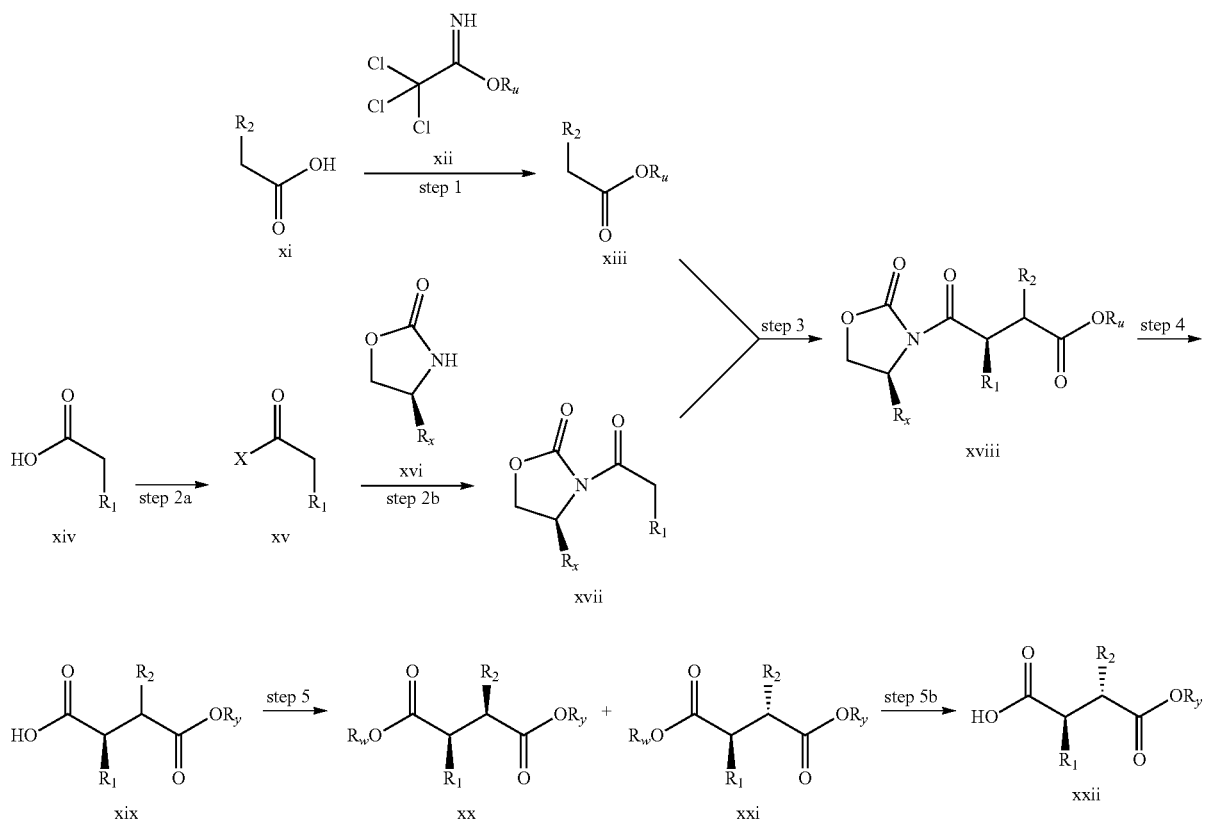

ture of solvents such as THF/water. If necessary, the diastereomers may be separated at this point via silica gel chromatography or preparative HPLC. Alternately, the mixture may be subjected to epimerization conditions, for example by treatment with LDA and diethylaluminum chloride followed by quenching with methanol or acetic acid to enrich the desired diastereomer.

Step 5: If desired, the desired (R,S)-diastereomer may be obtained in pure form by a series of steps involving protection of the carboxylic acid, separation of the diastereomers and deprotection, common steps known to one skilled in the art. For example, the mixture of diastereomers (xix) can be protected as the benzyl ester by treating with a reagent such as benzyl bromide in the presence of base such as potassium carbonate in a solvent such as DMF. This diastereomeric mixture can then be subjected to purification procedures, for example Preparative HPLC or silica gel chromatography. The diastereomerically pure material obtained can then be subjected to deprotection conditions (step 5b). For example, if R=Bn, the material can be treated under hydrogenation conditions using a catalyst such as palladium on carbon in a solvent such as MeOH under a hydrogen atmosphere.

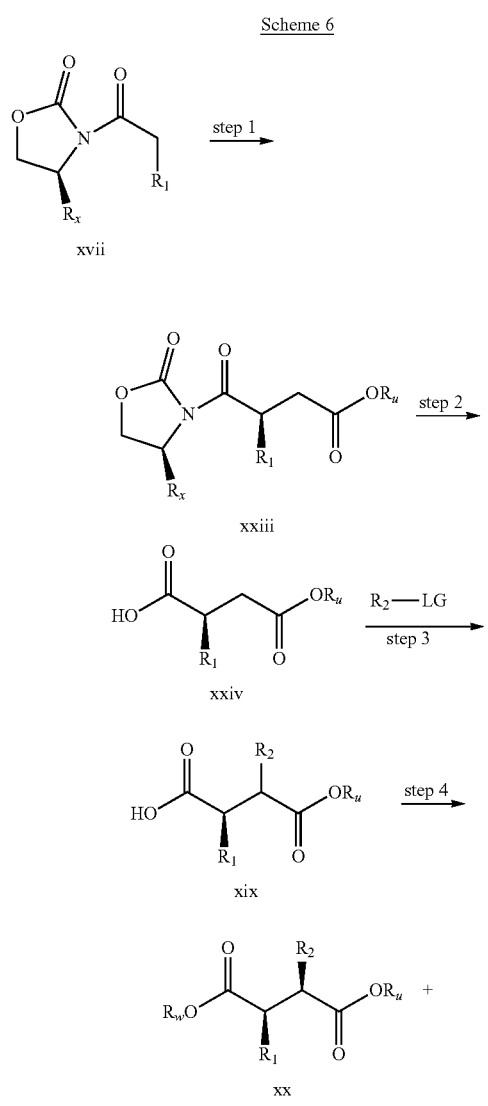

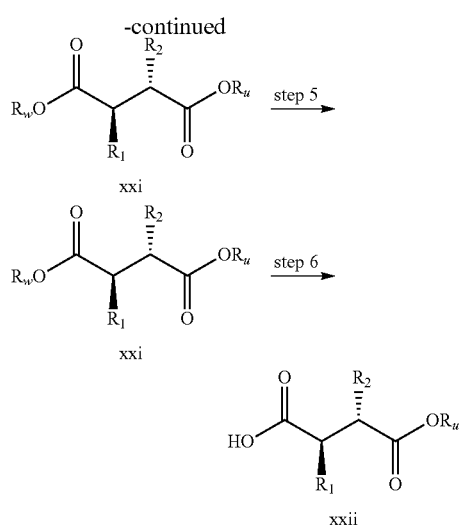

Compound (xix) in Scheme 5 may also be prepared from compound (xvii) by a synthetic sequence outlined in Scheme 6.

Step 1: The first step of Scheme 6 is accomplished by treating compound (xvii) with a base such as sodium bis(trimethylsilyl)-amide in a solvent such as THF at low temperature such as −78° C. under an inert atmosphere. To the resulting enolate of (xvii) is treated with a reagent such as tert-butyl bromoacetate to provide compound (xxiii).

Step 2: Conversion of compound (xxiii) to (xxiv) may be accomplished by treating compound (xxiii) with hydrogen peroxide and lithium hydroxide at an appropriate temperature using a mixture of solvents such as THF/water.

Step 3: Compound (xxiv) can be converted to compound (xix) by generating the enolate of (xxiv) with a base such as LDA in a solvent such as THF at low temperature such as −78° C. under an inert atmosphere and further treatment with a reagent ($R_2$-LG) bearing an appropriate leaving group (e.g., LG=triflate). Compound (xix) may then be utilized, for example, in step 1 of Scheme 8. Alternately, the mixture may be subjected to epimerization conditions, for example by treatment with LDA and diethylaluminum chloride followed by quenching with methanol or acetic acid to enrich the desired diastereomer. Moreover, a preferred embodiment entails the installation of a moiety that may later be transformed to another substituent. For example, using a different reactant ($R_2$-LG), such as allyl bromide, installs a suitable grouping for future modifications. Epimerization conditions, as noted above, may also be employed on this compound if desired.

Step 4: The fourth step of Scheme 6 is similar to that of step 5 in Scheme 5 and may be omitted if compound (xix) will be used directly in, for example, step 1 of Scheme 8. However, if further manipulation of, for example, $R_2$ of compound (xix) is desired, the carboxylic acid moiety of compound (xix) may be protected with a suitable protecting group, for example a benzyl group. Hence, compound (xix) may be treated with a reactant such as benzyl bromide, in the presence of a base such as potassium carbonate in a suitable solvent such as DMF. The resulting mixture of diastereoisomers may be separated if desired, employing suitable conditions such as preparative HPLC, preparative chiral HPLC or silica gel chromatography, and the resulting pure desired diastereoisomer compound (xxii) used in the subsequent steps.

Scheme 7

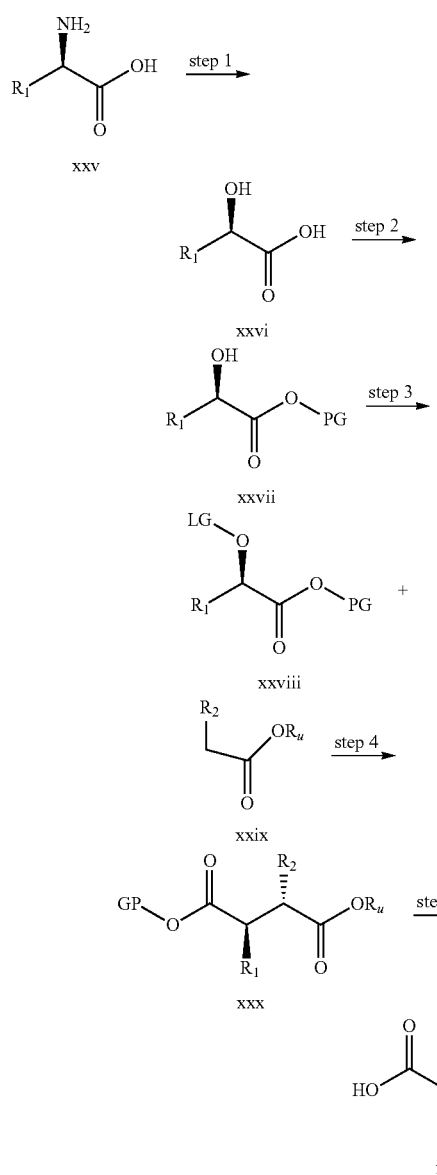

Step 1: The first step of Scheme 7 is accomplished by treating Compound (xxv) with a reagent such as sodium nitrite in an acid such as $H_2SO_4$ and a solvent such as water to provide Compound (xxvi).

Step 2: The acid group of Compound (xxvi) is protected with a protecting group to give Compound (xxvii), a strategy known to one skilled in the art. For example, the reaction may be performed using an alcohol such as benzyl alcohol in a solvent such as toluene and an acid such as $H_2SO_4$ to provide Compound (xxvii).

Step 3: Compound (xxviii) bearing a suitable leaving group may be prepared by treatment of Compound (xxvii) with a base such as 2,6-Lutidine and a reagent such as trifluoromethanesulfonic anhydride in a solvent such as DCM at an appropriate temperature.

Step 4: The preparation of Compound (xxx) may be effected by treating Compound (xxix) with a base such as LiHMDS in a solvent such as THF at an appropriate temperature such as −78° C., followed by the addition of a solution of Compound (xxviii) in a solvent such as THF.

Step 5: The protecting group of Compound (xxx) may be removed via many methods known to one skilled in the art. For example, a benzyl group may be removed by subjecting it to hydrogenation conditions using a palladium catalyst such as Pearlman's Catalyst in a solvent such as methanol to provide Compound (xxii).

Scheme 8

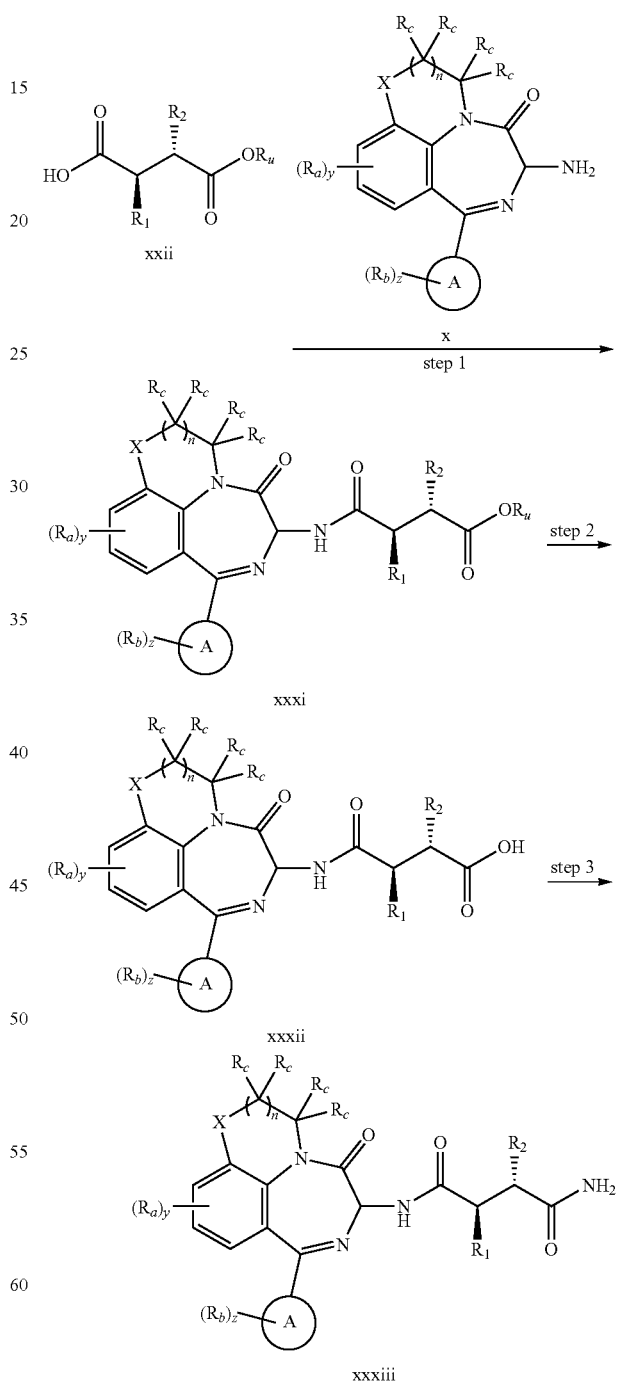

Step 1: Benzodiazepinone (x) may be coupled to either pure diastereomer compound (xxii) or diastereomeric mixture compound (xix) in the presence of a coupling reagent such as TBTU and a base such as TEA, in a solvent such as DMF to provide compound (xxxi) as either a diastereomerically pure compound or as a mixture of diastereoisomers, as appropriate. This mixture may be used as such in the subsequent step, or if desired, may be purified using an appropriate separation technique, such as chiral preparative chromatography to provide the diastereomerically pure compounds.

Step 2: Treatment of compound (xxxi) with an acid such as TFA at an appropriate temperature such as 25° C., in a solvent such as DCM provides compound (xxxii) as either a diastereomerically pure compound or as a mixture of diastereoisomers. This mixture may be used as such in the subsequent step, or if desired, may be purified using an appropriate separation technique, such as chiral preparative chromatography to provide the diastereomerically pure compounds.

Step 3: Conversion of compound (xxxii) to compound (xxxiii) may be accomplished via coupling of compound (xxxii) with an appropriate amine source such as ammonium chloride, a carbodiimide such as EDC, HOBT and a base such as TEA in a solvent such as DMF. If necessary the diastereomeric mixture can be separated using an appropriate separation technique, such as chiral preparative chromatography.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

ABBREVIATIONS

AcOH acetic acid
AlMe$_3$ trimethyl aluminum
Bn benzyl
Boc tert-butoxycarbonyl
Boc$_2$O di-tert-butyl dicarbonate
CBz benzyloxycarbonyl
DCC 1,3-dicyclohexylcarbodiimide
DCM dichloromethane
DMAP dimethylaminopyridine
DME dimethyl ether
DMF dimethylformamide
DMSO dimethyl sulfoxide
EDC 1-(3-dimethylaminopropyl)-3-ethylcarbodiimide hydrochloride
Et$_3$N triethyl amine
Et$_2$O diethyl ether
EtOH ethanol
EtOAc ethyl acetate
equiv. equivalence
g gram
h hour(s)
HOBt hydroxybenzotriazole
HPLC high pressure liquid chromatography
KOtBu potassium tert-butoxide
LCMS Liquid Chromatography-Mass Spectroscopy
LDA lithium diisopropylamide
LiHMDS lithium bis(trimethylsilyl)amide
MeI methyl iodide
MeOH methanol
min minute(s)
mL milliliter
mmol millimolar
NaHMDS sodium bis(trimethylsilyl)amide
n-BuLi n-butyl lithium
NH$_4$Oac ammonium acetate
Pd(OAc)$_2$ palladium acetate
RT retention time
t-Bu tertiary butyl
tBuOH tertiary butyl alcohol
tBuOMe tert-butyl methyl ether
TBTU O-(1H-benzotriazol-1-yl)-N,N,N',N'-tetramethyluroniumtetrafluoroborate
TEA triethylamine
TFA trifluoroacetic acid
THF tetrahydrofuran Intermediate S-1: (2R,3S)-3-(tert-Butoxycarbonyl)-6,6,6-trifluoro-2-(3,3,3-trifluoropropyl)hexanoic acid

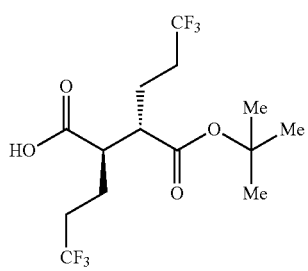

(S-1)

Intermediate S-1A: 3,3,3-Trifluoropropyl trifluoromethanesulfonate

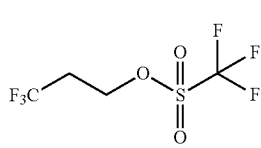

(S-1A)

To a cold (−25° C.), stirred solution of 2,6-lutidine (18.38 mL, 158 mmol) in DCM (120 mL) was added Tf$_2$O (24.88 mL, 147 mmol) over 3 min, and the mixture was stirred for 5 min. To the reaction mixture was added 3,3,3-trifluoropropan-1-ol (12 g, 105 mmol) over an interval of 3 min. After 2 hr, the reaction mixture was warmed to room temperature and stirred for 1 hr. The reaction mixture was concentrated to half its volume, then purified by loading directly on a silica gel column (330 g ISCO) and the product was eluted with DCM to afford Intermediate S-1A (13.74 g, 53%) as a colorless oil. $^1$H NMR (400 MHz, CDCl$_3$) δ ppm 4.71 (2H, t, J=6.15 Hz), 2.49-2.86 (2H, m).

Intermediate S-1B: (4S)-4-Benzyl-3-(5,5,5-trifluoropentanoyl)-1,3-oxazolidin-2-one

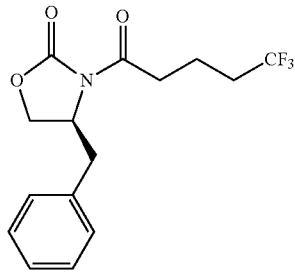

(S-1B)

To a stirring solution of 5,5,5-trifluoropentanoic acid (14.76 g, 95 mmol) and DMF (0.146 mL) in DCM (50 mL) was slowly added oxalyl chloride (8.27 mL, 95 mmol). After 2 h, the mixture was concentrated to dryness. A separate flask was changed with (S)-4-benzyloxazolidin-2-one (16.75 g, 95 mmol) in THF (100 mL) and then cooled to −78° C. To the solution was slowly added n-BuLi (2.5M, 37.8 mL, 95 mmol) over 10 min, stirred for 10 min, and then a solution of the above acid chloride in THF (50 mL) was slowly added over 5 min. The mixture was stirred for 30 min, and then warmed to room temperature. The reaction was quenched with saturated aqueous $NH_4Cl$. To the mixture, 10% aqueous LiCl was added, and then the mixture was extracted with $Et_2O$. The organic layer was washed with saturated aqueous $NaHCO_3$ then with brine, dried ($MgSO_4$), filtered and concentrated to dryness. The residue was purified by $SiO_2$ chromatography (ISCO, 330 g column, eluting with a gradient from 100% hexane to 100% EtOAc) to afford the product Intermediate S-1B; (25.25 g, 85%): $^1H$ NMR (400 MHz, $CDCl_3$) δ ppm 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Intermediate S-1C: tert-Butyl(3R)-3-(((4S)-4-benzyl-2-oxo-1,3-oxazolidin-3-yl)carbonyl)-6,6,6-trifluorohexanoate

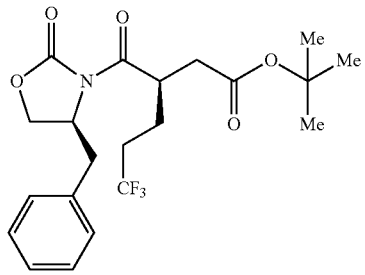

(S-1C)

To a cold (−78° C.), stirred solution of Intermediate S-1B (3.03 g, 9.61 mmol) in THF (20 mL) was added NaHMDS (1.0M in THF) (10.6 mL, 10.60 mmol) under a nitrogen atmosphere. After 2 hours, tert-butyl 2-bromoacetate (5.62 g, 28.8 mmol) was added neat via syringe at −78° C. and stirring was maintained at the same temperature. After 6 hours, the reaction mixture was warmed to room temperature. The reaction mixture was partitioned between saturated $NH_4Cl$ and EtOAc. The organic phase was separated, and the aqueous phase was extracted with EtOAc (3×). The combined organics were washed with brine, dried ($Na_2SO_4$), filtered and concentrated under reduced pressure. The residue was purified by flash chromatography (Teledyne ISCO CombiFlash Rf, 5% to 100% solvent A/B=hexanes/EtOAc, REDISEP® $SiO_2$ 120 g). Concentration of the appropriate fractions provided Intermediate S-1C (2.79 g, 67.6%) as a colorless viscous oil: $^1H$ NMR (400 MHz, $CDCl_3$) δ ppm 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Intermediate S-1D: (2R)-2-(2-tert-Butoxy-2-oxoethyl)-5,5,5-trifluoropentanoic acid

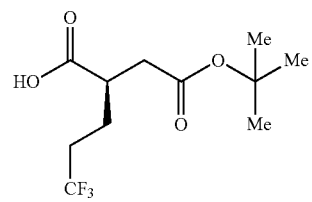

(S-1D)

To a cool (0° C.), stirred solution of Intermediate S-1C (2.17 g, 5.05 mmol) in THF (50 mL) and water (15 mL) was added a solution of LiOH (0.242 g, 10.11 mmol) and $H_2O_2$ (2.065 mL, 20.21 mmol) in $H_2O$ (2 mL). After 10 min, the reaction mixture was removed from the ice bath, stirred for 1 h, and then recooled to 0° C. Saturated aqueous $NaHCO_3$ (25 mL) and saturated aqueous $Na_2SO_3$ (25 mL) were added, and the reaction mixture was stirred for 10 min and then partially concentrated. The resulting mixture was extracted with DCM (2×), cooled with ice and made acidic with concentrated HCl to pH 3. The mixture was saturated with solid NaCl, extracted with EtOAc (3×), and then dried over $MgSO_4$, filtered and concentrated to a colorless oil to afford Intermediate S-1D, 1.2514 g, 92%): $^1H$ NMR (400 MHz, $CDCl_3$) δ ppm 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Intermediate S-1: (2R,3S)-3-(tert-Butoxycarbonyl)-6,6,6-trifluoro-2-(3,3,3-trifluoropropyl)hexanoic acid and Intermediate S-1E: (2R,3R)-3-(tert-Butoxycarbonyl)-6,6,6-trifluoro-2-(3,3,3-trifluoropropyl)hexanoic acid

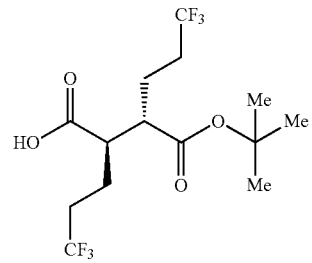

(S-1)

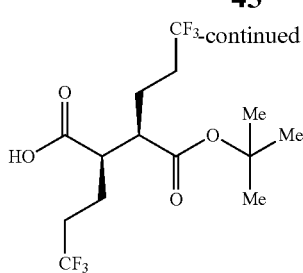
(S-1E)

To a cold (−78° C.), stirred solution of Intermediate S-1D (5 g, 18.50 mmol) in THF (60 mL) was slowly added LDA (22.2 mL, 44.4 mmol, 2.0M) over 7 min. After stirring for 2 hr, Intermediate S-1A (6.38 g, 25.9 mmol) was added to the reaction mixture over 3 min. After 60 min, the reaction mixture was warmed to −25° C. (ice/MeOH/dry ice) and stirred for an additional 60 min at which time saturated aqueous NH₄Cl was added. The separated aqueous phase was acidified with aqueous 1N HCl to pH 3, then extracted with Et₂O, washed the combined organic layers with brine (×2), dried over MgSO₄, filtered and concentrated to provide a 1:4 (I1: I1E) mixture (as determined by $^1$H NMR) of Intermediate S-1 and Intermediate S-1E (6.00 g, 89%) as a pale yellow solid. $^1$H NMR (500 MHz, CDCl₃) δ ppm 2.81 (1H, ddd, J=10.17, 6.32, 3.85 Hz), 2.63-2.76 (1H, m), 2.02-2.33 (4H, m), 1.86-1.99 (2H, m), 1.68-1.85 (2H, m), 1.47 (9H, s)

Intermediate S-1: (2R,3S)-3-(tert-Butoxycarbonyl)-6,6,6-trifluoro-2-(3,3,3-trifluoropropyl)hexanoic acid and Intermediate S-1E: (2R,3R)-3-(tert-Butoxycarbonyl)-6,6,6-trifluoro-2-(3,3,3-trifluoropropyl)hexanoic acid

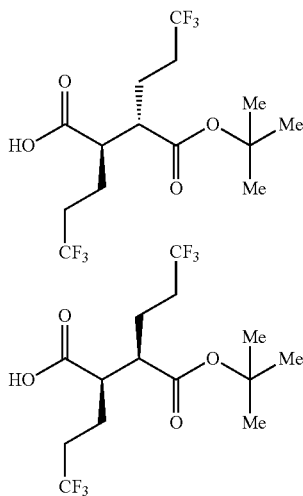

To a cold (−78° C.), stirred solution of a mixture of Intermediate S-1 and Intermediate S-1E (5.97 g, 16.30 mmol) in THF (91 mL) was added LDA (19 mL, 38.0 mmol, 2.0M in THF/hexane/ethyl benzene) dropwise via syringe over 10 min (internal temperature never exceeded −65° C., J-KEM® probe in reaction solution), stirred for 15 min, warmed to room temperature (24° C. water bath), stirred for 15 min, cooled to −78° C. for 15 min. To the reaction mixture was added Et₂AlCl (41 mL, 41.0 mmol, 1M in hexane) via syringe (internal temperature never exceeded −55° C.), stirred for 10 min, warmed to room temperature (24° C. bath) for 15 min then back to −78° C. for 15 min. Meanwhile, a 1000 mL round bottom flask was charged with MeOH (145 mL) and pre-cooled to −78° C. With vigorous stirring the reaction mixture was transferred via cannula over 5 min to the MeOH. The flask was removed from the bath, ice was added followed by slow addition of 1N HCl (147 mL, 147 mmol). Gas evolution was observed as the HCl was added. The reaction mixture was allowed to warm to room temperature during which the gas evolution subsided. The reaction mixture was diluted with EtOAc (750 mL), saturated with NaCl, the organic phase was separated, washed with a solution of potassium fluoride (8.52 g, 147 mmol) and 1N HCl (41 mL, 41.0 mmol) in water (291 mL), brine (100 mL), dried (Na₂SO₄) filtered and concentrated then dried under vacuum. $^1$H NMR showed product was 9:1 mixture of Intermediate S-1 and Intermediate S-1E. Obtained the enriched mixture of Intermediate S-1 and Intermediate S-1E (6.12 g, >99% yield) as a dark amber solid: $^1$H NMR (400 MHz, CDCl₃) δ ppm 2.64-2.76 (2H, m), 2.04-2.35 (4H, m), 1.88-2.00 (2H, m), 1.71-1.83 (2H, m), 1.48 (9H, s).

Alternate procedure to make Intermediate S-1:

Intermediate S-1F: (2R,3S)-1-Benzyl 4-tert-butyl 2,3-bis(3,3,3-trifluoropropyl)succinate

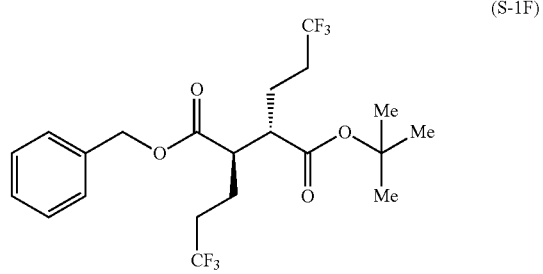 [SMILES: CC(C)(C)OC(=O)[C@@H](CCC(F)(F)F)[C@@H](CCC(F)(F)F)C(=O)OCc1ccccc1]
(S-1F)

To a stirred solution of a 9:1 enriched mixture of Intermediate S-1 and Intermediate S-1E (5.98 g, 16.33 mmol) in DMF (63 ml) was added potassium carbonate (4.06 g, 29.4 mmol) and benzyl bromide (2.9 ml, 24.38 mmol). The reaction mixture was stirred overnight. The reaction mixture was diluted with EtOAc (1000 mL), washed with 10% LiCl (3×200 mL), brine (200 mL) then dried (Na₂SO₄), filtered and concentrated then dried under vacuum. The residue was purified by SiO₂ chromatography using a toluene:hexane gradient. Obtained diastereomerically pure Intermediate S-1F (4.81 g, 65%) as a colorless solid: $^1$H NMR (400 MHz, chloroform-d) δ 7.32-7.43 (m, 5H), 5.19 (d, J=12.10 Hz, 1H), 5.15 (d, J=12.10 Hz, 1H), 2.71 (dt, J=3.52, 9.20 Hz, 1H), 2.61 (dt, J=3.63, 9.63 Hz, 1H), 1.96-2.21 (m, 4H), 1.69-1.96 (m, 3H), 1.56-1.67 (m, 1H), 1.45 (s, 9H).

Intermediate S-1: (2R,3S)-3-(tert-Butoxycarbonyl)-6,6,6-trifluoro-2-(3,3,3-trifluoropropyl)hexanoic acid

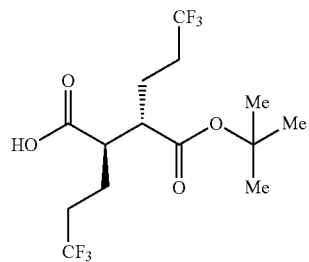
(S-1)

To a solution of Intermediate S-1F (4.81 g, 10.54 mmol) in MeOH (100 mL) was added 10% palladium on carbon (wet, Degussa type, 568.0 mg, 0.534 mmol) in a $H_2$-pressure flask. The vessel was purged with $N_2$ (4×) then with $H_2$ (2×), then pressurized to 50 psi and shaken overnight. The reaction mixture was depressurized and purged, the mixture was filtered through CELITE®, washed with MeOH then concentrated and dried under vacuum. Obtained Intermediate S-1 (3.81 g, 99% yield)) as a colorless solid: $^1$H NMR (400 MHz, chloroform-d) δ 2.62-2.79 (m, 2H), 2.02-2.40 (m, 4H), 1.87-2.00 (m, 2H), 1.67-1.84 (m, 2H), 1.48 (s, 9H).

Alternate procedure to make Intermediate S-1:

Intermediate S-1: (2R,3S)-3-(tert-Butoxycarbonyl)-6,6,6-trifluoro-2-(3,3,3-trifluoropropyl)hexanoic acid

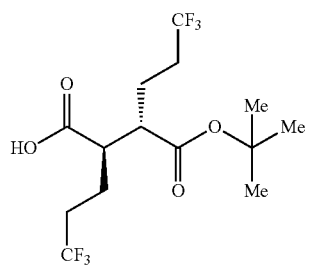

(S-1)

Intermediate S-1 as a mixture with Intermediate S-1E was prepared in a procedure identical as above from Intermediate S-1D to afford a 1:2.2 mixture of Intermediate S-1 and Intermediate S-1E (8.60 g, 23.48 mmol), which was enriched using LDA (2.0 M solution in THF, ethyl benzene and heptane, 28.2 mL, 56.4 mmol) and diethyl aluminum chloride (1.0 M solution in hexane, 59 mL, 59.0 mmol) in THF (91 mL). After workup as explained above, the resulting residue was found to be a 13.2:1 (by $^1$H NMR) mixture of Intermediate S-1 and Intermediate S-1E, which was treated as follows: The crude material was dissolved in MTBE (43 mL). Hexanes (26 mL) were slowly charged to the reaction mixture while maintaining a temperature below 30° C. The reaction mixture was stirred for 10 min. Next, tert-butylamine (2.7 mL, 1.1 eq) was charged slowly over a period of 20 minutes while maintaining a temperature below 30° C. This addition was observed to be exothermic. The reaction mixture was stirred for 2 hrs below 30° C. and filtered. The solid material was washed with 5:3 MTBE:hexane (80 mL), the filtrate was concentrated and set aside. The filtered solid was dissolved in dichloromethane (300 mL), washed with 1N HCl (100 mL), the organic layer was washed with brine (100 mL×2), then was concentrated under reduced pressure below 45° C. Obtained Intermediate S-1 (5.46 g, 64%).

A second alternate procedure for preparing Intermediate S-1:

Intermediate S-1G: tert-Butyl 5,5,5-trifluoropentanoate

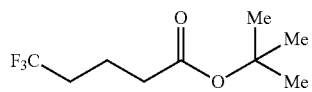

(S-1G)

To a stirred solution of 5,5,5-trifluoropentanoic acid (5 g, 32.0 mmol) in THF (30 mL) and hexane (30 mL) at 0° C., was added tert-butyl 2,2,2-trichloroacetimidate (11.46 mL, 64.1 mmol). The mixture was stirred for 15 min at 0° C. Boron trifluoride etherate (0.406 mL, 3.20 mmol) was added and the reaction mixture was allowed to warm to room temperature overnight. To the clear reaction mixture was added solid $NaHCO_3$ (5 g) and stirred for 30 min. The mixture was filtered through $MgSO_4$ and washed with hexanes (200 mL). The solution was allowed to rest for 45 min, and the resulting solid material was removed by filtering on the same $MgSO_4$ filter again, washed with hexanes (100 mL) and concentrated under reduced pressure without heat. The volume was reduced to about 30 mL, filtered through a clean fritted funnel, washed with hexane (5 mL), and then concentrated under reduced pressure without heat. The resulting neat oil was filtered through a 0.45 μm nylon membrane filter disk to provide Intermediate S-1G (6.6 g, 31.4 mmol 98% yield) as a colorless oil: $^1$H NMR (400 MHz, $CDCl_3$) δ ppm 1.38 (s, 9H) 1.74-1.83 (m, 2H) 2.00-2.13 (m, 2H) 2.24 (t, J=7.28 Hz, 2H).

Intermediate S-1H: (4S)-4-(Propan-2-yl)-3-(5,5,5-trifluoropentanoyl)-1,3-oxazolidin-2-one

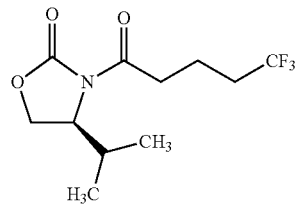

(S-1H)

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min and the solution was stirred until all bubbling subsided. The reaction mixture was concentrated under reduced pressure to give pale yellow oil. To a separate flask charged with a solution of (4S)-4-(propan-2-yl)-1,3-oxazolidin-2-one (4.18 g, 32.4 mmol) in THF (100 mL) at −78° C. was added n-BuLi (2.5M in hexane) (13.0 mL, 32.5 mmol) dropwise via syringe over 5 min. After stirring for 10 min, the above acid chloride dissolved in THF (20 mL) was added via cannula over 15 min. The reaction mixture was warmed to 0° C., and was allowed to warm to room temperature as the bath warmed and stirred overnight. To the reaction mixture was added saturated $NH_4Cl$, and then extracted with EtOAc (2×). The combined organics were washed with brine, dried ($Na_2SO_4$), filtered and concentrated under reduced pressure. The crude material was purified by flash chromatography (Teledyne ISCO CombiFlash Rf, 5% to 60% solvent A/B=hexanes/EtOAc, REDISEP® $SiO_2$ 120 g). Concentration of appropriate fractions provided Intermediate S-1H (7.39 g, 86%) as a colorless oil: $^1$H NMR (400 MHz, $CDCl_3$) δ ppm 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Intermediate S-1I: (2S,3R)-tert-Butyl 6,6,6-trifluoro-3-((S)-4-isopropyl-2-oxooxazolidine-3-carbonyl)-2-(3,3,3-trifluoropropyl)hexanoate and Intermediate S-1J: (2R,3R)-tert-Butyl 6,6,6-trifluoro-3-((S)-4-isopropyl-2-oxooxazolidine-3-carbonyl)-2-(3,3,3-trifluoropropyl)hexanoate

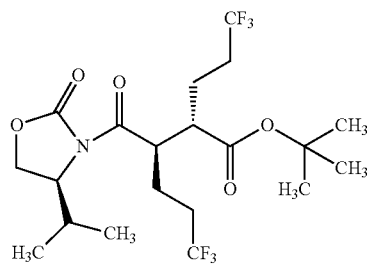

(S-1I)

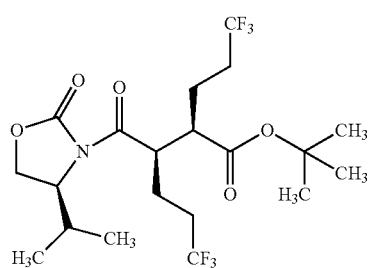

(S-1J)

To a cold (−78° C.), stirred solution of diisopropylamine (5.3 mL, 37.2 mmol) in THF (59 mL) under nitrogen atmosphere was added n-BuLi (2.5M in hexane) (14.7 mL, 36.8 mmol), then warmed to 0° C. to give a 0.5 M solution of LDA. A separate vessel was charged with Intermediate S-1H (2.45 g, 9.17 mmol), the material was azeotroped twice with benzene (the RotoVap air inlet was fitted with nitrogen inlet to completely exclude humidity), and then toluene (15.3 mL) was added. This solution was added to a flask containing dry lithium chloride (1.96 g, 46.2 mmol). To the resultant mixture, cooled to −78° C., was added LDA solution (21.0 mL, 10.5 mmol) and stirred at −78° C. for 10 min, warmed to 0° C. for 10 min, and then recooled to −78° C. To a separate reaction vessel containing Intermediate S-1G (3.41 g, 16.07 mmol), also azeotroped twice with benzene, was added toluene (15.3 mL), cooled to −78° C. and LDA (37.0 mL, 18.5 mmol) was added. The resulting solution was stirred at −78° C. for 25 min. At this time the enolate derived from the ester was transferred via cannula into the solution of the oxazolidinone enolate, stirred at −78° C. for an additional 5 min at which time the septum was removed and solid powdered bis(2-ethylhexanoyloxy)copper (9.02 g, 25.8 mmol) was rapidly added to the reaction vessel and the septum replaced. The vessel was immediately removed from the cold bath and immersed into a warm water bath (40° C.) with rapid swirling with a concomitant color change from the initial turquoise to brown. The reaction mixture was stirred for 20 min, was poured into 5% aqueous NH$_4$OH (360 mL) and extracted with EtOAc (2×). The combined organics were washed with brine, dried (Na$_2$SO$_4$), filtered and concentrated under reduced pressure. The residue was purified by flash chromatography (Teledyne ISCO CombiFlash Rf, 0% to 60% solvent A/B=hexanes/EtOAc, REDISEP® SiO$_2$ 120 g). Concentration of appropriate fractions provided a mixture of S-1I and S-1J (2.87 g, 66%) as pale yellow viscous oil. $^1$H NMR showed the product was a 1.6:1 mixture of diastereomers S-1I:S-1J as determined by the integration of the multiplets at 2.74 and 2.84 ppm: $^1$H NMR (400 MHz, CDCl$_3$) δ ppm 4.43-4.54 (2H, m), 4.23-4.35 (5H, m), 4.01 (1H, ddd, J=9.54, 6.27, 3.51 Hz), 2.84 (1H, ddd, J=9.41, 7.28, 3.64 Hz), 2.74 (1H, ddd, J=10.29, 6.27, 4.02 Hz), 2.37-2.48 (2H, m, J=10.38, 6.98, 6.98, 3.51, 3.51 Hz), 2.20-2.37 (3H, m), 1.92-2.20 (8H, m), 1.64-1.91 (5H, m), 1.47 (18H, s), 0.88-0.98 (12H, m).

Intermediate S-1: (2R,3S)-3-(tert-Butoxycarbonyl)-6,6,6-trifluoro-2-(3,3,3-trifluoropropyl)hexanoic acid and Intermediate S-1E: (2R,3R)-3-(tert-Butoxycarbonyl)-6,6,6-trifluoro-2-(3,3,3-trifluoropropyl)hexanoic acid

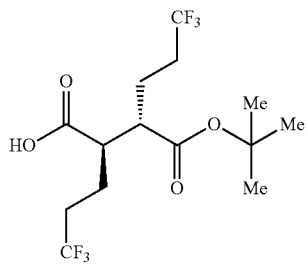

(S-1)

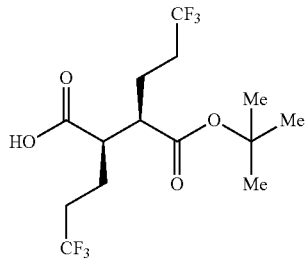

(S-1E)

To a cool (0° C.), stirred solution of Intermediate S-1I and Intermediate S-1J (4.54 g, 9.51 mmol) in THF (140 mL) and water (42 mL) was sequentially added hydrogen peroxide (30% in water) (10.3 g, 91 mmol) and LiOH (685.3 mg, 28.6 mmol) and the mixture was stirred for 1 hr. At this time the reaction vessel was removed from the cold bath and then stirred for 1.5 hr. The reaction was judged complete by HPLC. To the reaction mixture was added saturated NaHCO$_3$ (45 mL) and saturated Na$_2$SO$_3$ (15 mL), and then partially concentrated under reduced pressure. The resulting crude solution was extracted with DCM (3×). The aqueous phase was acidified to pH-1-2 with 1N HCl, extracted with DCM (3×) and EtOAc (1×). The combined organics were washed with brine, dried (Na$_2$SO$_4$), filtered and concentrated under reduced pressure to provide a mixture of Intermediates S-1 and S-1E (3.00 g, 86%) as a colorless oil: $^1$H NMR (400 MHz, CDCl$_3$) δ ppm 2.76-2.84 (1H, m, diastereomer 2), 2.64-2.76 (3H, m), 2.04-2.35 (8H, m), 1.88-2.00 (4H, m), 1.71-1.83 (4H, m), 1.48 (9H, s, diastereomer 1), 1.46 (9H, s, diastereomer 2); $^1$H NMR showed a 1.7:1 mixture of S-1E:S-1F by integration of the peaks for the t-butyl groups.

Intermediate S-1: (2R,3S)-3-(tert-Butoxycarbonyl)-6,6,6-trifluoro-2-(3,3,3-trifluoropropyl)hexanoic acid and Intermediate S-1F: (2R,3R)-3-(tert-Butoxycarbonyl)-6,6,6-trifluoro-2-(3,3,3-trifluoropropyl)hexanoic acid

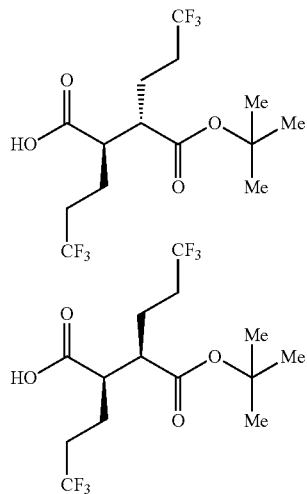

(S-1)

(S-1E)

To a cold (−78° C.), stirred solution of diisopropylamine (1.7 mL, 11.93 mmol) in THF (19 mL) under nitrogen atmosphere was added n-BuLi (2.5M in hexanes) (4.8 mL, 12.00 mmol). The mixture was stirred for 5 min and then warmed to 0° C. In a separate vessel, to a cold (−78° C.) stirred solution of the mixture of Intermediate S-1 and S-1E (1.99 g, 5.43 mmol) in THF (18 mL) was added the LDA solution prepared above via cannula slowly over 25 min. The mixture was stirred for 15 min, then warmed to room temperature (placed in a 24° C. water bath) for 15 min, and then again cooled to −78° C. for 15 min. To the reaction mixture was added Et$_2$AlCl (1M in hexane) (11.4 mL, 11.40 mmol) via syringe, stirred for 10 min, warmed to room temperature for 15 min and then cooled back to −78° C. for 15 min. Methanol (25 mL) was rapidly added, swirled vigorously while warming to room temperature, then concentrated to ~¼ original volume. The mixture was dissolved in EtOAc and washed with 1N HCl (50 mL) and ice (75 g). The aqueous phase was separated, extracted with EtOAc (2×). The combined organics were washed with a mixture of KF (2.85 g in 75 mL water) and 1N HCl (13 mL) [resulting solution pH 3-4], then with brine, dried (Na$_2$SO$_4$), filtered and concentrated under reduced pressure to give a 9:1 (S-1:S-1E) enriched diastereomeric mixture (as determined by $^1$H NMR) of Intermediate S-1 and Intermediate S-1E (2.13 g, >99%) as a pale yellow viscous oil: $^1$H NMR (400 MHz, CDCl$_3$) δ ppm 2.64-2.76 (2H, m), 2.04-2.35 (4H, m), 1.88-2.00 (2H, m), 1.71-1.83 (2H, m), 1.48 (9H, s).

Intermediate S2: (R)-2-((S)-1-tert-Butoxy-3-cyclopropyl-1-oxopropan-2-yl)-5,5,5-trifluoropentanoic acid

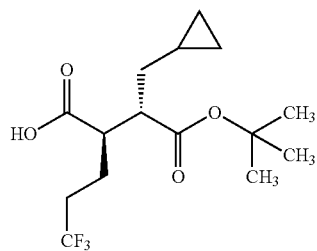

(S2)

Intermediate S2A: (4S)-4-(Propan-2-yl)-3-(5,5,5-trifluoropentanoyl)-1,3-oxazolidin-2-one

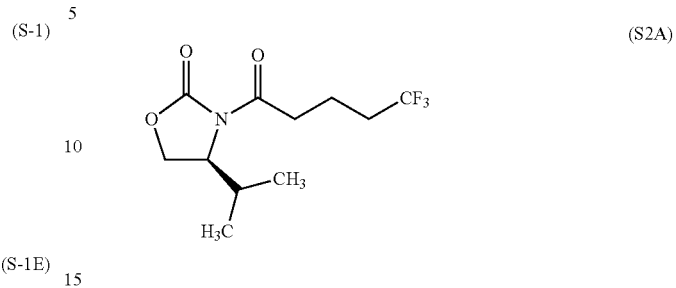

(S2A)

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min. The solution was stirred until all bubbling subsided. The reaction mixture was concentrated under reduced pressure to give a pale yellow oil. To a separate flask charged with a solution of (4S)-4-(propan-2-yl)-1,3-oxazolidin-2-one (4.18 g, 32.4 mmol) in THF (100 mL) at −78° C. was added n-BuLi (13.0 mL, 32.5 mmol, 2.5M in hexane) dropwise via syringe over 5 min. After stirring for 10 min, the above acid chloride dissolved in THF (20 mL) was added via cannula over 15 min. The reaction mixture was warmed to 0° C., and was allowed to warm to room temperature as the bath warmed and stirred overnight. To the reaction mixture was added saturated NH$_4$Cl, and then extracted with EtOAc (2×). The combined organics were washed with brine, dried (Na$_2$SO$_4$), filtered and concentrated under reduced pressure. The crude material was purified by silica gel chromatography (hexanes/EtOAc) to provide Preparation 1B (7.39 g, 86%) as a colorless oil: $^1$H NMR (400 MHz, CDCl$_3$) δ 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Intermediate S2B: tert-Butyl 3-cyclopropylpropanoate

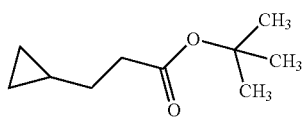

(S2B)

To a cool (0° C., precooled for at least 15 min), stirred solution of 3-cyclopropylpropanoic acid (5 g, 43.8 mmol) in hexane (30.0 mL) and THF (30 mL) under N$_2$ was added tert-butyl 2,2,2-trichloroacetimidate (15.7 mL, 88 mmol) portion wise over 5 min. The reaction mixture was stirred for 15 min. Boron trifluoride ether complex (0.555 mL, 4.38 mmol) was added and the reaction mixture was allowed to warm to room temperature as the bath warmed overnight. To the clear reaction mixture was added NaHCO$_3$ (5 g) and stirred for 60 min. The suspension was filtered through MgSO$_4$ and washed with 300 mL hexane. The filtrate was allowed to sit, then the formed solid was filtered through the same MgSO$_4$ filter, washed with hexane (100 mL). The filtrate was concentrated under vacuo with the water bath not turned on. The residue was purified by silica gel chromatography (hexanes/EtOAc) to provide Intermediate I1B (6.05 g, 81%) as clear oil: $^1$H NMR (400 MHz, CDCl$_3$) δ 2.29 (2H, t, J=7.48 Hz), 1.35-1.54 (11H, m), 0.60-0.75 (1H, m), 0.29-0.46 (2H, m), −0.06-0.10 (2H, m).

Intermediate S2C: (2S,3R)-tert-Butyl 2-(cyclopropylmethyl)-6,6,6-trifluoro-3-((S)-4-isopropyl-2-oxooxazolidine-3-carbonyl)hexanoate and Intermediate S1D: (2R,3R)-tert-Butyl 2-(cyclopropylmethyl)-6,6,6-trifluoro-3-((S)-4-isopropyl-2-oxooxazolidine-3-carbonyl)hexanoate

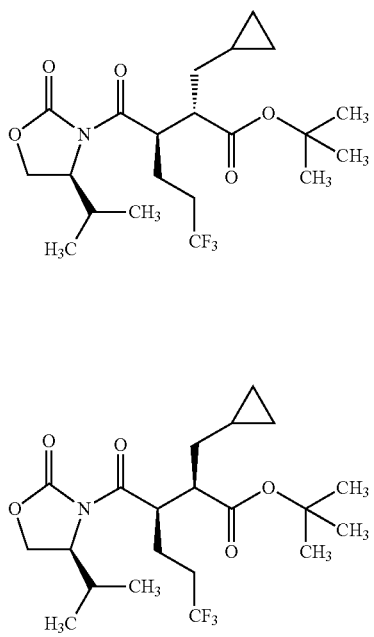

Diisopropylamine (6.64 ml, 46.6 mmol) was dissolved in 71.7 mL of THF and cooled to −78° C., then n-BuLi (18.0 mL, 44.9 mmol, 2.5M in hexane) was added dropwise over a period of 5 minutes. After 5 minutes, the resulting 0.5 M LDA solution was kept at 0° C.

In a separate flask, lithium chloride (2.62 g, 61.7 mmol) was dried under high vacuum with heating and cooled under nitrogen. Intermediate S1A (3.0 g, 11.23 mmol), azeotroped once with toluene, was transferred with 15.0 mL toluene to the flask containing LiCl, and cooled to −78° C. To this stirring suspension was added LDA (25.83 mL, 12.91 mmol, 1.15 equiv., 0.5M LDA) dropwise via syringe over 5 min. The reaction mixture was stirred at −78° C. for 15 minutes, then at 0° C. for 10 minutes and cooled to −78° C.

In a separate flask, Intermediate S2B (3.44 g, 20.21 mmol) was dissolved in 15.0 mL toluene under N$_2$ and cooled to −78° C. To this solution was added LDA (46.48 mL, 23.24 mmol, 1.15 equiv., 0.5M LDA) dropwise and stirred at −78° C. for 30 minutes, at which time this solution was added via cannula (fast negative pressure, all added within 30 seconds) to the LiCl/oxazolidone solution at −78° C. After 1 minute following transfer, solid bis(2-ethylhexanoyloxy)copper (10.80 g, 30.9 mmol) was added at −78° C., and the flask was transferred to 40° C. water bath and swirled vigorously for 15 minutes, and quenched over 5% NH$_4$OH solution (20 mL saturated NH$_4$OH and 100 mL water), and extracted with ethyl acetate (2×100 mL). The pooled organic phases were washed with brine, dried (Na$_2$SO$_4$), filtered, concentrated and purified by silica gel chromatography (hexanes/EtOAc) to afford a mixture of Intermediate S1C and Intermediate S1D (1.58 g, 32% yield) as an oil: $^1$H NMR showed this material to be a 1.5:1 mixture of S1C:S1D, by integration of the t-Bu peaks: $^1$H NMR of diastereoisomer mixture (400 MHz, CDCl$_3$) δ 4.53-4.41 (m, 2H), 4.39-4.19 (m, 5H), 4.10-4.01 (m, 1H), 2.89-2.77 (m, 2H), 2.47-2.26 (m, 2H), 2.16-1.72 (m, 8H), 1.47 (s, 9H, t-Bu of I1C, integrates for relative intensity of 1.5), 1.46 (s, 9H, t-Bu of I1D, integrates for relative intensity of 1), 0.98-0.86 (m, 16H), 0.78-0.64 (m, 2H), 0.56-0.37 (m, 4H), 0.14-0.01 (m, 4H).

Intermediate S2: (R)-2-((S)-1-tert-Butoxy-3-cyclopropyl-1-oxopropan-2-yl)-5,5,5-trifluoropentanoic acid and Intermediate S1E: (R)-2-((R)-1-tert-Butoxy-3-cyclopropyl-1-oxopropan-2-yl)-5,5,5-trifluoropentanoic acid

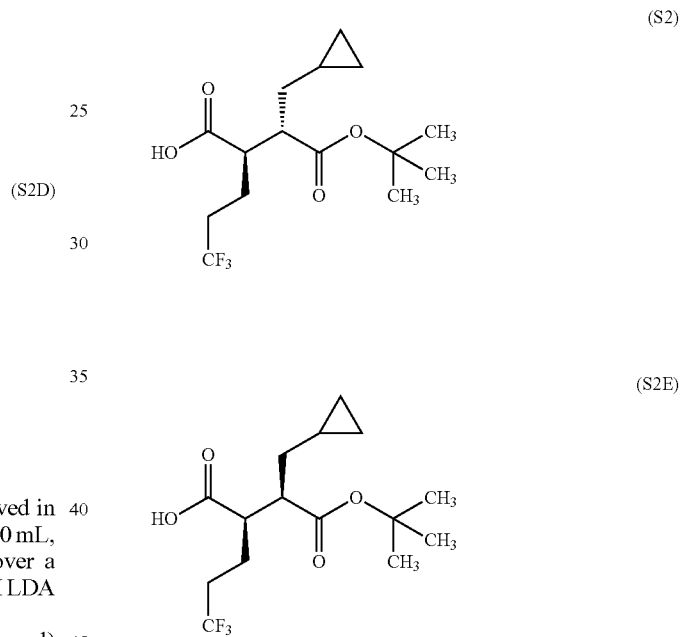

To a cool (0° C.), stirred solution of a mixture of Intermediates S1C:S1D (3.4 g, 7.81 mmol) in THF (60 mL) and water (20 mL) was added 30% H$_2$O$_2$ (4.82 mL, 79 mmol) followed by LiOH (0.567 g, 23.66 mmol). The reaction mixture was allowed to gradually warm up to room temperature and stirred at room temperature for 3 h. To the reaction mixture was added saturated Na$_2$SO$_3$ (20 mL) and saturated NaHCO$_3$ (40 mL), and then stirred for 5 min. The reaction mixture was partially concentrated and extracted with DCM (80 mL). The aqueous phase was acidified to pH ~2, saturated with NaCl, extracted with EtOAc (2×). The combined extracts were dried (MgSO$_4$), filtered and concentrated to provide a mixture of Intermediate S2 and Intermediate S2E (2.01 g, 79%): $^1$H NMR showed this material to be a 1.4:1 mixture of S1:S1E, by integration of the t-Bu peaks: $^1$H NMR of mixture of diastereomers (400 MHz, CDCl$_3$) δ 2.82-2.59 (m, 4H), 2.31-2.03 (m, 4H), 1.95-1.52 (m, 7H), 1.44 (s, 9H, t-Bu of I1, integrates for relative intensity of 1.4), 1.42 (s, 9H, t-Bu of I1E, integrates for relative intensity of 1), 0.93 (d, J=6.6 Hz, 1H), 0.88 (d, J=6.8 Hz, 1H), 0.74-0.57 (m, 2H), 0.43 (t, J=6.8 Hz, 3H), 0.11--0.04 (m, 3H).

Intermediate S2: (R)-2-((S)-1-tert-Butoxy-3-cyclopropyl-1-oxopropan-2-yl)-5,5,5-trifluoropentanoic acid and Intermediate S1E: (R)-2-((R)-1-tert-Butoxy-3-cyclopropyl-1-oxopropan-2-yl)-5,5,5-trifluoropentanoic acid, an enriched mixture (S2)

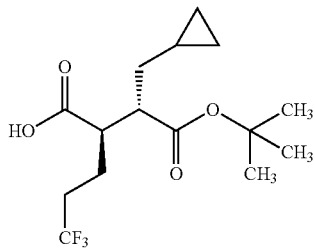

(S2E)

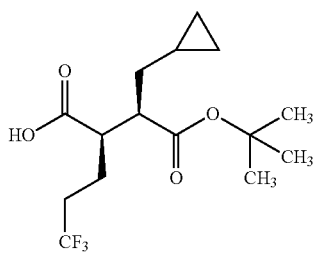

To a cold (−78° C.), stirred solution of a 1.4:1 mixture of Intermediate S1 and S1E (2.00 g, 6.17 mmol) in THF (30 mL) under N₂ was added LDA (7.54 mL, 13.57 mmol, 1.8M) via syringe over 5 min, stirred for 15 min, warmed to room temperature (24° C. water bath), stirred for 15 min, cooled to −78° C. for 15 min. To the reaction mixture was added diethylaluminum chloride (12.95 mL, 12.95 mmol, 1M in hexane) via syringe, stirred for 10 min, warmed to room temperature (24° C. bath) for 15 min then back to −78° C. for 25 min. MeOH (38.9 mL, 962 mmol) was rapidly added, removed from bath then ice and 1N HCl (55.5 mL, 55.5 mmol) was gradually added was added slowly. Once gas evolution subsided, the mixture was extracted with EtOAc (2×), the combined organics washed with a solution of potassium fluoride (3.26 g, 56.2 mmol) in water (106 mL, 5895 mmol) and 1N HCl (15.72 mL, 15.72 mmol), brine, and then dried (Na₂SO₄). The mixture was subsequently filtered and concentrated to afford a~2:1 (S1:S1E, as determined by integration of the t-Bu peaks in the ¹H NMR) enriched mixture of Intermediate S1 and Intermediate S1E (1.79 g, 90%): ¹H NMR of mixture of diastereomers (400 MHz, CDCl₃) δ 2.87-2.57 (m, 2H), 2.36-2.06 (m, 2H), 1.97-1.81 (m, 2H), 1.81-1.70 (m, 1H), 1.70-1.56 (m, 1H), 1.47 (s, 9H, t-Bu of I1, integrates for relative intensity of 2.0), 1.45 (s, 9H, t-Bu of I1E, integrates for relative intensity of 1), 0.99-0.87 (m, 1H), 0.77-0.61 (m, 1H), 0.54-0.38 (m, 2H), 0.16--0.01 (m, 2H).

Intermediate S2F: (2R,3S)-1-Benzyl 4-tert-butyl 3-(cyclopropylmethyl)-2-(3,3,3-trifluoropropyl)succinate and Intermediate S1G: (2R,3R)-1-Benzyl 4-tert-butyl 3-(cyclopropylmethyl)-2-(3,3,3-trifluoropropyl)succinate (S2F)

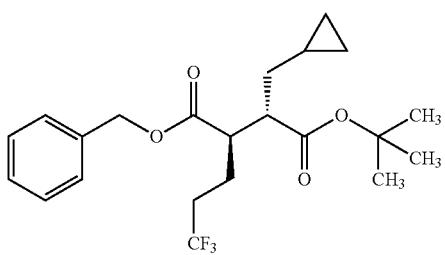

(S2G)

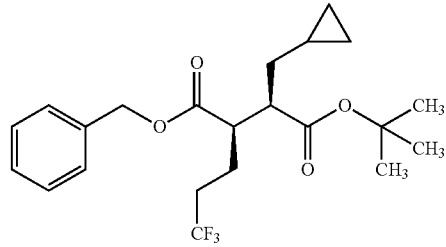

To a stirred solution of a 2.15:1 mixture of Intermediates S2 and S2E (2.22 g, 6.84 mmol) and benzyl bromide (0.98 ml, 8.24 mmol) in DMF (25 ml) was added potassium carbonate (1.41 g, 10.20 mmol). The reaction mixture was then stirred for 5.5 h. The reaction mixture was diluted with EtOAc (300 mL), washed with 10% LiCl (3×100 mL), saturated NaCl, then dried (Na₂SO₄), filtered and concentrated. The residue was purified by silica gel chromatography (hexane:toluene) to give Intermediate S2F (1.5 g, 53%) and Intermediate S1G (0.778 g, 27%): Intermediate S2F: ¹H NMR (400 MHz, CDCl₃) δ 7.43-7.31 (m, 29H), 5.17 (d, J=11.9 Hz, 6H), 5.13 (d, J=11.9 Hz, 6H), 2.75-2.64 (m, 11H), 2.19-1.94 (m, 12H), 1.93-1.81 (m, 6H), 1.79-1.69 (m, 6H), 1.63-1.56 (m, 4H), 1.46 (s, 47H), 1.14 (ddd, J=13.8, 7.2, 3.5 Hz, 6H), 0.68-0.55 (m, 6H), 0.45-0.37 (m, 11H), −0.02--0.11 (m, 6H). Intermediate I1G: ¹H NMR (400 MHz, CDCl₃) δ 7.40-7.32 (m, 5H), 5.16 (d, J=12.3 Hz, 1H), 5.13 (d, J=12.1 Hz, 1H), 2.88-2.79 (m, 1H), 2.74 (ddd, J=8.8, 7.3, 4.4 Hz, 1H), 2.18-1.93 (m, 2H), 1.90-1.79 (m, 2H), 1.70-1.59 (m, 1H), 1.44 (s, 9H), 1.31 (ddd, J=14.1, 7.3, 4.5 Hz, 1H), 0.73-0.61 (m, 1H), 0.49-0.38 (m, 2H), 0.10-0.03 (m, 1H), −0.01--0.07 (m, 1H).

Intermediate S2

(S1)

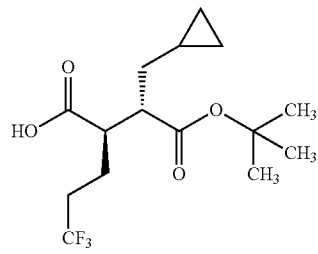

Intermediate S2F (2.80 g, 6.76 mmol) was dissolved in ethyl acetate (26.0 mL) and methanol (26.0 mL). Palladium on carbon (10% wet Degussa, 0.539 g, 0.507 mmol) was added, then the atmosphere was exchanged for H₂ three times. The reaction mixture was stirred about 2 h, then filtered with MeOH washes. The filtrate was concentrated to afford Intermediate S1 (2.19 g, 100% yield): ¹H NMR (400 MHz, CDCl₃) δ 2.79-2.67 (m, 2H), 2.36-2.21 (m, 1H), 2.18-2.03 (m, 1H), 1.94 (dtd, J=14.6, 9.8, 4.8 Hz, 1H), 1.78 (ddd, J=11.1, 5.3, 3.0 Hz, 1H), 1.63 (ddd, J=13.9, 9.2, 7.0 Hz, 1H), 1.49 (s, 9H), 1.35 (ddd, J=13.8, 7.0, 3.9 Hz, 1H), 0.77-0.63 (m, 1H), 0.48 (dq, J=8.1, 1.7 Hz, 2H), 0.15-0.02 (m, 2H).

An alternate method to prepare Intermediate S1F, and hence Intermediate S2:

Intermediate S2H: (S)-4-Benzyl-3-(5,5,5-trifluoropentanoyl)oxazolidin-2-one

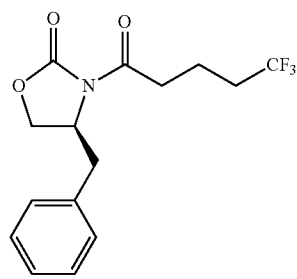
(S2H)

To a stirring solution of 5,5,5-trifluoropentanoic acid (71.4 g, 457 mmol) in DCM (315 mL) and 5 drops of DMF was added oxalyl chloride (229 mL, 457 mmol). The reaction mixture was then stirred until gas evolution subsided. The reaction mixture was concentrated, and the material was used below.

A separate flask was charged with (S)-4-benzyloxazolidin-2-one (60 g, 339 mmol) and THF (315 mL), cooled to −78° C., followed by the dropwise addition of n-butyl lithium (183 mL, 2.5M, 457 mmol). A heavy suspension resulted during addition, therefore additional THF (315 mL) was added. Once the addition of BuLi was ended, to the reaction mixture was added a solution of the above acid chloride in THF (150 mL) dropwise, stir for 10 minutes at −78° C., then allowed to warm to room temperature. The reaction was quenched with aqueous saturated NH$_4$Cl solution at 0-5° C. The reaction mixture was extracted with EtOAc, washed with water, brine, dried (Na$_2$SO$_4$), filtered and concentrated. The residue was purified by silica gel chromatography (hexane/EtOAc) to provide Intermediate S2H (87 g, 81%): $^1$H NMR (400 MHz, CDCl$_3$) δ 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Intermediate S2I: tert-Butyl(3R)-3-(((4S)-4-benzyl-2-oxo-1,3-oxazolidin-3-yl)carbonyl)-6,6,6-trifluorohexanoate

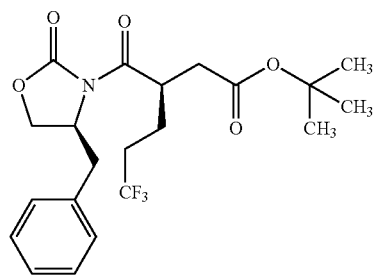
(S2I)

To a cold (−78° C.), stirred solution of Intermediate S1H (43 g, 136 mmol) in THF (150 mL) was added NaHMDS (150 mL, 1.0M in THF, 150 mmol) under nitrogen atmosphere. After 2 hours, tert-butyl 2-bromoacetate (53.2 g, 273 mmol) in THF (100 mL) was added at −78° C. and stirring was maintained at the same temperature. After 6 hours, the reaction mixture was warmed to room temperature. The reaction mixture was partitioned between saturated NH$_4$Cl and EtOAc. The organic phase was separated, and the aqueous was extracted with EtOAc (3×). The combined organics were washed with brine, dried (Na$_2$SO$_4$), filtered and concentrated under reduced pressure. The residue was purified by silica gel chromatography (hexane/EtOAc) to provide Intermediate S2I (37 g, 63%): $^1$H NMR (400 MHz, CDCl$_3$) δ 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Intermediate S2J: (2R)-2-(2-tert-Butoxy-2-oxoethyl)-5,5,5-trifluoropentanoic acid

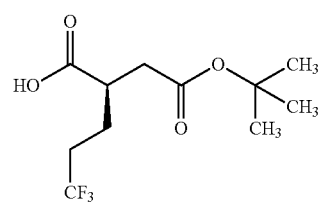
(S1J)

To a cool (0° C.), stirred solution of Intermediate S2I (26 g, 60.5 mmol) in THF (390 mL) and water (104 mL) was added H$_2$O$_2$ (24.1 mL, 236 mmol) followed by LiOH (2.75 g, 115 mmol) as a solution in water (28 mL). The reaction mixture was allowed to gradually warm to room temperature and stirred at room temperature for 3 h. The reaction mixture was cooled to 0° C., then saturated Na$_2$SO$_3$ and saturated NaHCO$_3$ were added. The reaction mixture was stirred for 5 min, and then partially concentrated and extracted with DCM (20 ml). The aqueous phase was acidified to pH ~3, extracted with EtOAc. The extract was dried (Na$_2$SO$_4$), filtered and concentrated to obtain Intermediate S1J (15 g, 92%): $^1$H NMR (400 MHz, CDCl$_3$) δ 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Intermediate S2K: (2R,3S)-3-(tert-Butoxycarbonyl)-2-(3,3,3-trifluoropropyl)hex-5-enoic acid and Intermediate S2L: (2R,3R)-3-(tert-Butoxycarbonyl)-2-(3,3,3-trifluoropropyl)hex-5-enoic acid

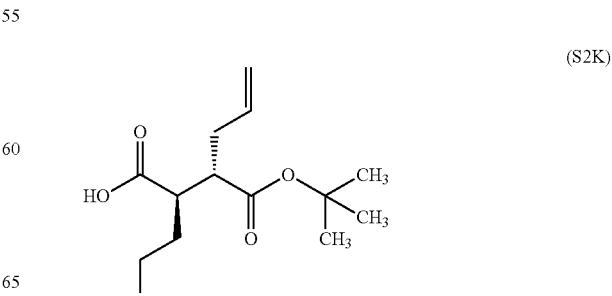
(S2K)

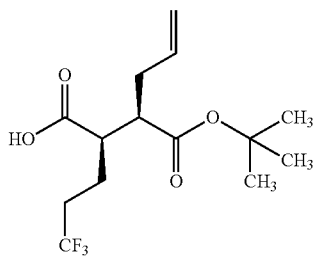

(S2L)

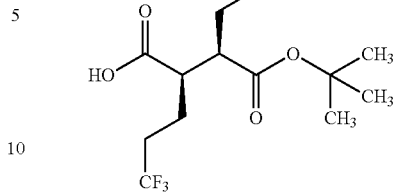

(S1L)

A flask was charged with THF (150 ml), then cooled to −20° C., then with stirring n-butyllithium (53.9 ml, 2.5 M in hexane, 135 mmol) was added, followed by diisopropylamine (19.4 ml, 137 mmol) over 55 min while maintaining the internal temperature at less than −8.5° C. After addition was complete, the solution was stirred at 0° C. for 45 min, and then cooled to −78° C. To this was added a solution of Intermediate S1J (14.56 g, 53.9 mmol) in THF (15.0 ml) over 20 min, while maintaining internal temperature at less than −72° C. After addition was complete, the mixture was stirred at −78° C. for 100 min. To this was added 3-bromoprop-1-ene (6.38 ml, 75 mmol) over 10 min. The reaction mixture was stirred allowed to slowly warm to room temperature as bath warmed, and stirred overnight. To the solution was added ice, quenched with 1N HCl (215 mL) to pH about 1, saturated with NaCl. The layers were separated. The aqueous layer was extracted with EtOAc (1×250 mL, 1×150 mL). The combined organic phases were washed with brine (1×300 mL), dried (MgSO$_4$), filtered, and evaporated. The residue was treated with benzene (50 mL) and evaporated twice, dried in vacuo to afford a mixture of Intermediate S2K and Intermediate S2L (16.8 g, 100%): $^1$H NMR indicated a ratio 1:2 for S1K:S1L: $^1$H NMR of diastereoisomer mixture (400 MHz, CDCl$_3$) δ 5.81-5.66 (m, 1H), 5.17-5.04 (m, 2H), 2.81-2.62 (m, 2H), 2.45-2.38 (m, 2H), 2.33-2.03 (m, 3H), 1.96-1.83 (m, 2H), 1.45 (s, 9H, t-Bu of S2K, integrates for relative intensity of 1), 1.44 (s, 9H, t-Bu of S1L, integrates for relative intensity of 2).

Intermediate S2K: (2R,3S)-3-(tert-Butoxycarbonyl)-2-(3,3,3-trifluoropropyl)hex-5-enoic acid and Intermediate S2L: (2R,3R)-3-(tert-Butoxycarbonyl)-2-(3,3,3-trifluoropropyl)hex-5-enoic acid, an enriched mixture (S1K)

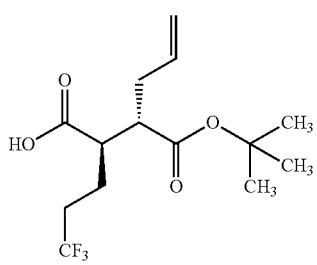

To a cold (−78° C.) stirred solution of a mixture of Intermediate S2K and Intermediate S2L (10 g, 32.2 mmol) in THF (150 mL) was slowly added LDA (39.4 mL, 70.9 mmol, 1.8M in heptane/THF/ethylbenzene). After stirring for 15 min the reaction mixture was placed in a room temperature water bath. After 15 min the reaction mixture was placed back in a −78° C. bath, stirred for 15 min then diethylaluminum chloride (81 mL, 81 mmol, 1M in hexane) was added via addition funnel. The reaction mixture was stirred at −78° C. After 10 min the reaction mixture was placed in a room temperature water bath for 15 min and then cooled back to −78° C. bath for 15 min. Meanwhile, a separate flask was charged MeOH (300 mL) and cooled to −78° C. The reaction mixture was then transferred to the cold and rapidly stirring MeOH via cannula by nitrogen pressure. After the transfer was complete ice (86 g) was added to the reaction mixture followed by slow addition of 1N HCl (300 mL). The reaction mixture was stirred until all gas evolution subsided. EtOAc (400 mL) was added, the phases separated, and the aqueous phase was extracted with EtOAc (300 mL). The combined EtOAc layers were washed with a mixture of potassium fluoride (17 g) in 600 mL H$_2$O and 1N HCl (86 mL), followed by brine. The organic phase was dried (Na$_2$SO$_4$), filtered and concentrated under reduced pressure to provide a 7:1 (S1K:S1L) enriched mixture of Intermediate S2K and Intermediate S2L (10.0 g, 100%): $^1$H NMR of diastereoisomer mixture (400 MHz, CDCl$_3$) δ 5.81-5.66 (m, 1H), 5.17-5.04 (m, 2H), 2.81-2.62 (m, 2H), 2.45-2.38 (m, 2H), 2.33-2.03 (m, 3H), 1.96-1.83 (m, 2H), 1.45 (s, 9H, t-Bu of I2K, integrates for relative intensity of 7), 1.44 (s, 9H, t-Bu of I2L, integrates for relative intensity of 1).

Intermediate S2M: (2S,3R)-4-Benzyl 1-tert-butyl 2-allyl-3-(3,3,3-trifluoropropyl)succinate (S2M)

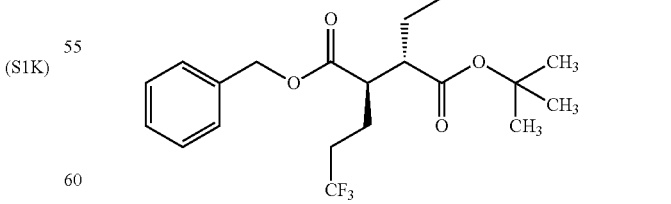

To a stirred solution of a 7:1 enriched mixture of Intermediate S1K and Intermediate S1L (10 g, 32.2 mmol) in DMF (100 ml) was added benzyl bromide (4.6 ml, 38.7 mmol) and potassium carbonate (6.68 g, 48.3 mmol). The reaction mixture was stirred for two hours at room temperature. To the reaction mixture was added Et₃N (9.0 mL. 64.5 mmol), followed by stirring for 60 min. The reaction mixture was diluted with Et₂O, washed with 10% LiCl (3×100 mL), brine (100 mL), and then dried (Na₂SO₄), filtered and concentrated. The residue was purified by silica gel chromatography (hexane/toluene) to provide Intermediate S2M (8.7 g, 67%): ¹H NMR (400 MHz, CDCl₃) δ 7.40-7.31 (m, 5H), 5.70 (ddt, J=16.9, 10.2, 7.1 Hz, 1H), 5.19-5.11 (m, 2H), 5.09-5.02 (m, 2H), 2.83-2.68 (m, 2H), 2.43-2.32 (m, 2H), 2.19-1.94 (m, 2H), 1.91-1.81 (m, 2H), 1.42 (s, 9H).

Intermediate S2F: (2R,3S)-1-Benzyl 4-tert-butyl 3-(cyclopropylmethyl)-2-(3,3,3-trifluoropropyl)succinate

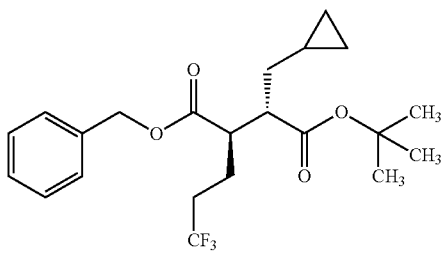

(S2F)

To a mixture of 40% KOH [KOH (6 g, 107 mmol) in water (9 mL)] and Et₂O (60 mL) cooled to 0° C. was added 1-methyl-3-nitro-1-nitrosoguanidine (1.5 g, 10.20 mmol) portion wise. The resulting solution was swirled several times. The ether layer (yellow solution) was pipetted to a mixture of Intermediate I1M (450 mg, 1.124 mmol) and Pd(OAc)₂ (25 mg, 0.11 mmol) in Et₂O (18 mL) at 0° C. The mixture was stirred at 0° C. for 3 h, and then the reaction was quenched with several drops of acetic acid. The resulting mixture was washed with saturated NaHCO₃ and brine, dried over MgSO₄, filtered and concentrated. The above oil was purified by silica gel chromatography (hexane/EtOAc) to afford Intermediate S2F (377 mg, 81%) as a colorless oil: HPLC: RT=3.790 min (H₂O/MeOH with TFA, CHROMOLITH® SpeedROD, 4.6×50 mm, gradient=4 min, wavelength=220 nm); MS(ES):m/z=415 [M+H⁺]; ¹H NMR (400 MHz, CDCl₃) δ 7.43-7.31 (m, 5H), 5.21-5.07 (m, 2H), 2.76-2.62 (m, 2H), 2.18-1.66 (m, 4H), 1.58-1.54 (m, 1H), 1.46 (s, 9H), 1.14 (ddd, J=13.8, 7.1, 3.5 Hz, 1H), 0.71-0.53 (m, 1H), 0.47-0.34 (m, 2H), 0.05--0.10 (m, 2H).

Intermediate S3: (2R,3S)-3-(tert-Butoxycarbonyl)-2-(3,3,3-trifluoropropyl)hexanoic acid

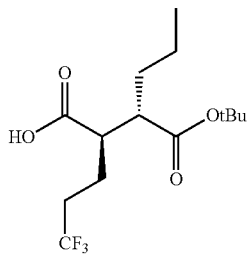

(S3)

Intermediate S3M (0.8 g, 1.998 mmol) was dissolved in MeOH (15.37 ml). Palladium on carbon (Degussa, 10%) (0.053 g, 0.050 mmol) was added, then the atmosphere was exchanged with H₂ three times. The reaction mixture was stirred for ca. 6 hours, then filtered with EtOAc rinses. The filtrate was concentrated to afford Intermediate S3 (627 mg, 100%): ¹H NMR (400 MHz, chloroform-d) δ 2.72-2.65 (m, 1H), 2.64-2.56 (m, 1H), 2.34-2.04 (m, 2H), 1.98-1.86 (m, 1H), 1.82-1.59 (m, 2H), 1.47 (s, 9H), 1.44-1.23 (m, 3H), 0.99-0.86 (m, 3H).

Intermediate S-4: (2R,3S)-3-(tert-Butoxycarbonyl)-6,6,6-trifluoro-2-(3-fluoropropyl)hexanoic acid

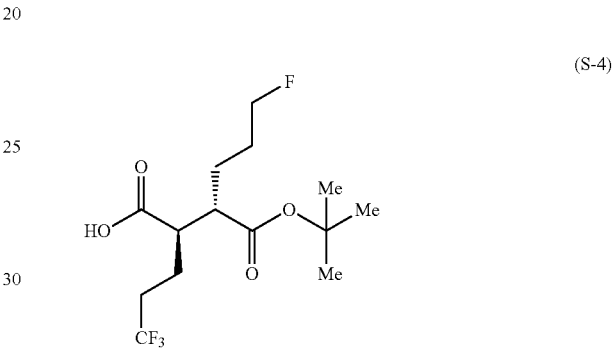

(S-4)

Intermediate S-4A: 3-Fluoropropyltrifluoromethanesulfonate

(S-4A)

To a cold (−25° C.), stirred solution of 2,6-Lutidine (4.60 mL, 39.5 mmoL) in DCM (30 mL) was added triflic anhydride (6.00 mL, 35.5 mmoL) over 3 min. Then 3-fluoropropane-1-ol (1.61 g, 20.6 mmoL) was added. The reaction mixture was warmed to room temperature for 2.5 h. The reaction mixture was then concentrated to half its volume and purified by flash chromatography (Teledyne ISCO CombiFlash, isocratic DCM, REDISEP® SiO₂ 120 g, detecting at 254 nM, and monitoring at 220 nM). Concentration of the appropriate fractions provided Intermediate S-4A (2.92 g, 67.4%). ¹H NMR (400 MHz, chloroform-d) δ ppm 4.69 (2H, t, J=6.16 Hz), 4.65 (1H, t, J=5.50 Hz), 4.54 (1H, t, J=5.61 Hz), 2.25 (1H, dt, J=11.39, 5.86 Hz), 2.19 (1H, dt, J=11.44, 5.94 Hz)

Intermediate S-4: (2R,3S)-3-(tert-Butoxycarbonyl)-6-fluoro-2-(3,3,3-trifluoropropyl)hexanoic acid and Intermediate S-4B: (2R,3R)-3-(tert-Butoxycarbonyl)-6-fluoro-2-(3,3,3-trifluoropropyl)hexanoic acid

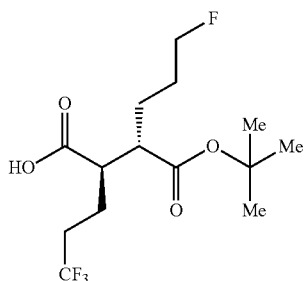
(S-4)

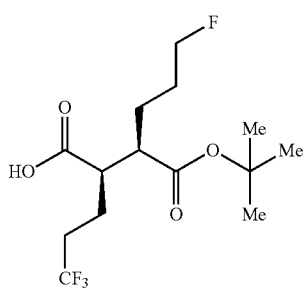
(S-4B)

To a cold (−78° C.), stirred solution of Intermediate S-1D (1.01 g, 3.73 mmol) in THF (15 mL) was slowly added LDA (4.56 mL, 8.21 mmol) over 5 min. After stirring for 1.5 h, Intermediate S-3A (1.02 g, 4.85 mmol) was added to the reaction mixture over 3 min. After 17 min, the reaction mixture was warmed to −25° C. bath (ice/MeOH/dry ice) for 1.5 h. The reaction was quenched with water (15 mL). The mixture was then extracted with CH$_2$Cl$_2$ (3×20 mL). The organic layer was again extracted with 1N NaOH (3×20 mL) and the aqueous layers were combined. The aqueous layer was cooled in ice/water bath and then acidified with 6 N HCl to pH 1. Next, the aqueous layer was saturated with solid NaCl and extracted with EtOAc (2×85 mL). The combined organics were washed with brine, dried over anhydrous magnesium sulfate, and concentrated under reduced pressure to provide a mixture of Intermediate S-4 and Intermediate S-4B (0.96 g, 78%) as an oil. $^1$H NMR (400 MHz, chloroform-d) δ ppm 4.48-4.56 (1H, m), 4.36-4.44 (1H, m), 2.75-2.83 (1H, m), 2.61-2.72 (1H, m), 2.08-2.34 (2H, m), 1.83-1.98 (3H, m), 1.66-1.82 (4H, m), 1.44-1.51 (9H, m). $^1$H NMR showed a 1:6.4 mixture diastereomers (Intermediate S-3:Intermediate S-3B) by integration of the peaks for the t-Bu groups.

Intermediate S-4: (2R,3S)-3-(tert-Butoxycarbonyl)-6,6,6-trifluoro-2-(3-fluoropropyl)hexanoic acid and Intermediate S-4B: (2R,3R)-3-(tert-Butoxycarbonyl)-6-fluoro-2-(3,3,3-trifluoropropyl)hexanoic acid

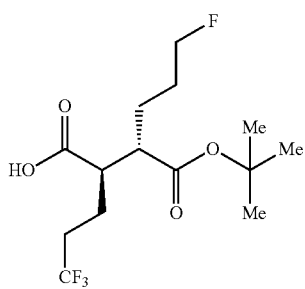
(S-4)

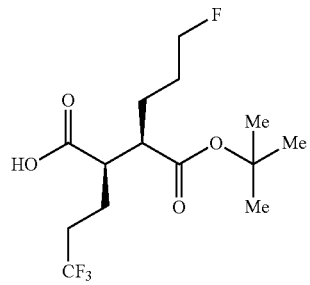
(S-4B)

A mixture of Intermediate S-4 and Intermediate S-4B (0.30 g, 0.91 mmol) was taken in THF (5 mL) to afford a colorless solution which was cooled to −78° C. Then, LDA (1.11 mL, 2.00 mmol) (1.8M in heptane/THF/ethylbenzene) was slowly added to the reaction mixture over 3 min. After stirring for 15 min the reaction mixture was placed in a room temperature water bath. After 15 min the reaction mixture was placed back in −78° C. bath and then diethylaluminum chloride (1.91 mL, 1.91 mmol) (1M in hexane) was added slowly over 5 min. The reaction mixture was stirred at −78° C. After 15 min the reaction mixture was placed in a room temperature water bath for 10 min and then cooled back to −78° C. bath. After 15 min the reaction was quenched with MeOH (5.51 mL, 136 mmol), removed from the −78° C. bath and concentrated. To the reaction mixture was added ice and HCl (8.17 mL, 8.17 mmol) then extracted with EtOAc (2×). The organic layer was washed with potassium fluoride (0.48 g, 8.26 mmol) in 16 mL H$_2$O and 10.0 ml, of 1N HCl. The organics were dried over anhydrous magnesium sulfate and concentrated under reduced pressure to provide a mixture of Intermediate S-4 and Intermediate S-4B (0.20 g, 65% yield) as a light yellow oil. $^1$H NMR (400 MHz, chloroform-d) δ ppm 4.47-4.56 (1H, m), 4.33-4.43 (1H, m), 2.59-2.76 (2H, m), 2.21-2.35 (1H, m), 2.06-2.19 (1H, m), 1.88-2.00 (1H, m), 1.59-1.85 (6H, m), 1.47 (9H, s). $^1$H NMR showed a 9:1 ratio in favor of the desired diastereomer Intermediate S-4.

Intermediate S-5: (R)-2-((R)-2-(tert-Butoxy)-2-oxo-1-phenylethyl)-5,5,5-trifluoropentanoic acid

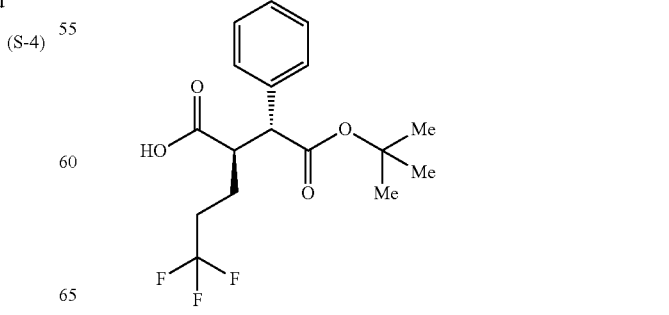
(S5)

Intermediate S5A: tert-Butyl 2-phenylacetate

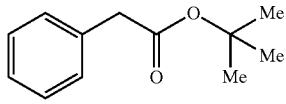
(S5A)

A solution of 2-phenylacetic acid (12 g, 88 mmol) in tBuOAc (250 mL) in a 1 L round-bottomed flask was treated with perchloric acid, 70% redistilled (0.212 mL, 3.53 mmol) stirred at room temperature for 20 hours. The solution was transferred very slowly to stirred mixture of saturated aqueous NaHCO$_3$ and Et$_2$O. Extensive bubbling was observed. The resulting layers were separated and the organic layer washed with saturated aqueous NaHCO$_3$, dried over MgSO$_4$, filtered, and concentrated to give tert-butyl 2-phenylacetate, Intermediate S5A (11.6 g, 68% yield). $^1$H NMR (500 MHz, chloroform-d) δ 7.34-7.29 (m, 2H), 7.28-7.22 (m, 3H), 3.52 (s, 2H), 1.44 (s, 9H).

Intermediate S5B: (2R)-5,5,5-Trifluoro-2-hydroxypentanoic acid

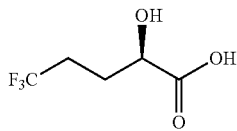
(S5B)

To a cool (0° C.), stirred solution of (2R)-2-amino-5,5,5-trifluoropentanoic acid (4.09 g, 23.90 mmol) (US 2009/0111858 A1) and H$_2$SO$_4$ (2.8 mL, 52.5 mmol) in water (95 mL) was added a solution of sodium nitrite (9.89 g, 143 mmol) in water (30 mL) dropwise via addition funnel over 60 min. The reaction mixture was allowed to slowly warm to room temperature and stirred overnight. The reaction mixture was diluted with Et$_2$O, the aqueous phase was separated and extracted with Et$_2$O (3×). The combined organics were dried (Na$_2$SO$_4$), filtered and concentrated under reduced pressure to provide Intermediate S5B (4.1551 g, >99%) as an amber oil. $^1$H NMR (400 MHz, CDCl$_3$) δ 4.33 (1H, dd, J=8.03, 4.27 Hz), 2.09-2.42 (3H, m), 1.88-2.02 (1H, m).

Intermediate S5C: Benzyl(2R)-5,5,5-trifluoro-2-hydroxypentanoate

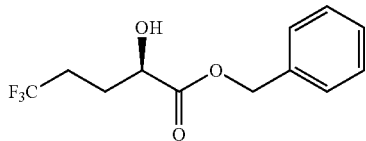
(S5C)

To a stirred solution of Intermediate S5B (4.1551 g, 24.14 mmol), benzyl alcohol (3.2 mL, 30.8 mmol) in benzene (40 mL) was added H$_2$SO$_4$ (0.28 mL, 5.25 mmol). The reaction mixture was heated to 50° C. for 10 h. The reaction mixture was cooled to room temperature, cooled in ice/water bath and then 0.5M NaOH (32 mL, 16.00 mmol) was added. The mixture was stirred for a few minutes, and was extracted with Et$_2$O, washed with brine, dried (Na$_2$SO$_4$), filtered and concentrated under reduced pressure. The residue was purified by flash chromatography (Teledyne ISCO CombiFlash Rf, 0% to 100% solvent CH$_2$Cl$_2$/EtOAc, REDISEP® SiO$_2$ 120 g). Concentration of appropriate fractions provided Intermediate S5C (3.88 g, 61%) as a colorless oil: $^1$H NMR (400 MHz, CDCl$_3$) δ 7.33-7.44 (5H, m), 5.25 (2H, s), 4.28 (1H, dt, J=8.09, 4.11 Hz), 2.85 (1H, d, J=4.77 Hz), 2.07-2.34 (3H, m), 1.84-1.96 (1H, m).

Intermediate S5D: Benzyl(2R)-5,5,5-trifluoro-2-{[(trifluoromethyl)sulfonyl]oxy}pentanoate

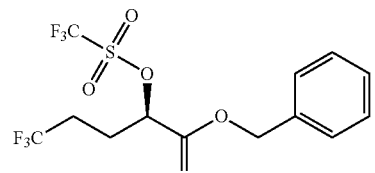
(S5D)

To a cold (−25° C.), stirred solution of 2,6-lutidine (2.352 mL, 20.19 mmol) in CH$_2$Cl$_2$ (30 mL) was added triflic anhydride (3.18 mL, 18.85 mmol) slowly over 2 minutes. The reaction mixture was stirred at −25° C. and became light yellow/orange in color. After 10 min, S5C (3.53 g, 13.46 mmol) was added dropwise over 5 min and stirred at −25° C. for 30 minutes. The reaction mixture was warmed to room temperature and concentrated to a small volume. The residue was diluted with heptane and loaded directly onto a silica gel column (220 g), eluted with a gradient from 20% CH$_2$Cl$_2$/heptane to 50% CH$_2$Cl$_2$/heptane. Concentration of appropriate fractions provided S5D (3.476 g, 66%): $^1$H NMR (400 MHz, CDCl$_3$) δ 7.33-7.45 (5H, m), 5.29 (2H, d, J=5.50 Hz), 5.21 (1H, t, J=5.50 Hz), 2.04-2.37 (4H, m).

Intermediate S5E: (2R,3R)-1-Benzyl 4-tert-butyl 3-phenyl-2-(3,3,3-trifluoropropyl)succinate

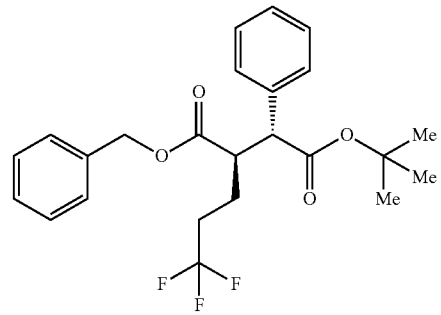
(S5E)

A solution of tert-butyl 2-phenylacetate, Intermediate S5A, (8.5 g, 44.2 mmol) in THF (400 mL) in a 1 L round-bottomed flask was cooled in −78° C. bath and treated with a solution of KHMDS, 0.5M in toluene (97 mL, 48.6 mmol) via cannula over 10 minutes. After 10 minutes, the mixture was removed from the −78° C. bath, placed in a room temperature water bath, stirred for 15 minutes, and then again cooled in -78° C. bath. After 15 minutes a solution of Intermediate S5D, (R)-benzyl 5,5,5-trifluoro-2-(((trifluoromethyl) sulfonyl)oxy)pentanoate (19.18 g, 48.6 mmol) in THF (50 mL) in a 100 mL round bottom flask was added over 10 min via cannula with a 20 mL THF rinse. The reaction mixture turned cloudy. The reaction mixture was stirred at -78° C. for 1 hour and then quenched with saturated aqueous NH$_4$Cl. The mixture was removed from -78° C. bath, diluted with 10% aqueous LiCl and extracted with Et$_2$O. The organic layer was dried over MgSO$_4$, filtered and concentrated. The resulting light brown residue was dissolved in 100 mL CH$_2$Cl$_2$ and treated with charcoal and MgSO$_4$. The mixture was filtered to give a nearly colorless solution. The CH$_2$Cl$_2$ solution was concentrated and diluted with hexane and cooled in -20° C. freezer. The resulting solids were filtered and rinsed with cold hexane (containing 5% MTBE) and dried on fritted filter funnel under a stream of nitrogen to give 8.16 g. The solid was triturated with 40 mL hexane and 4 mL MTBE. The white suspension was stirred at room temperature for 1 hour, cooled and stirred at -20° C. for 3 hours before filtering the white solid. The solid was washed with cold solvent (10:1 hexane: MTBE) to afford (2R,3R)-1-benzyl 4-tert-butyl 3-phenyl-2-(3,3,3-trifluoropropyl) succinate S5E (7.16 g, 37% yield) as a white solid. $^1$H NMR (500 MHz, chloroform-d) δ 7.32-7.23 (m, 8H), 7.05-6.97 (m, 2H), 4.89-4.76 (m, 2H), 3.69 (d, J=11.4 Hz, 1H), 3.23 (ddd, J=11.2, 9.9, 3.9 Hz, 1H), 2.19-2.04 (m, 2H), 2.03-1.88 (m, 2H), 1.40 (s, 9H).

Intermediate S5F: (R)-2-((R)-2-(tert-Butoxy)-2-oxo-1-phenylethyl)-5,5,5-trifluoropentanoic acid

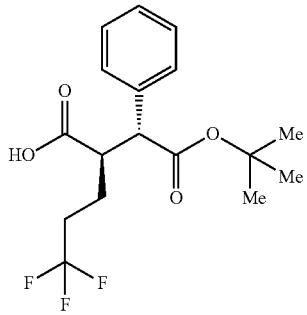

(S5)

In a 250 mL round-bottomed flask a suspension of (2R, 3R)-1-benzyl 4-tert-butyl 3-phenyl-2-(3,3,3-trifluoropropyl) succinate, Intermediate S5E, (7.16 g, 16.40 mmol) and Pd/C, 10% (1.746 g, 1.640 mmol) in ethyl acetate (35 mL) and MeOH (35 mL) was hydrogenated using a hydrogen filled balloon while stirring at room temperature. When the reaction was complete (monitored by HPLC) the suspension was filtered through 0.45 µm membrane and rinsed with MeOH and EtOAc. The filtrate was concentrated and dried under vacuum to afford Intermediate S5 (5.65 g, 99% yield). MS (m-1)= 345. $^1$H NMR (500 MHz, DMSO-d$_6$) δ 7.37-7.26 (m, 5H), 3.67 (d, J=10.5 Hz, 1H), 3.04 (td, J=10.3, 3.7 Hz, 1H), 2.38-2.20 (m, 2H), 1.88-1.70 (m, 2H), 1.37 (s, 9H).

Intermediate S6: (R)-2-((R)-2-tert-Butoxy-1-(3-methylisoxazol-4-yl)-2-oxoethyl)-5,5,5-trifluoropentanoic acid

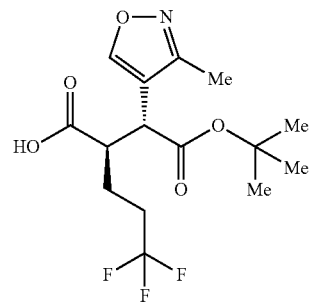

(S6)

Intermediate S6A: (2R,3R)-1-Benzyl 4-tert-butyl 3-(3-methylisoxazol-4-yl)-2-(3,3,3-trifluoropropyl) succinate

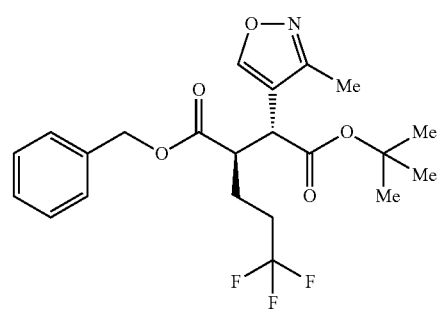

(S6A)

In a 250 mL round-bottomed flask, a solution of tert-butyl 2-(3-methylisoxazol-4-yl)acetate (1.75 g, 8.87 mmol) in THF (56 mL) and toluene (27 mL) was cooled in a -78° C. bath and treated with a solution of 1M KHMDS (11.09 mL, 11.09 mmol) in THF dropwise over 2 minutes via syringe. After stirring for 15 minutes at -78° C., the reaction mixture was placed in a room temperature water bath for 15 minutes and then placed in a -78° C. bath for another 15 minutes before a solution of Intermediate S5D, (R)-benzyl 5,5,5-trifluoro-2-(trifluoromethylsulfonyloxy)pentanoate (4.55 g, 11.53 mmol) in 6 mL THF and 3 mL toluene was added over 2 minutes. The reaction mixture was stirred in -78° C. bath for 2 hours before being quenched with saturated aqueous NH$_4$Cl and then warmed to room temperature. The mixture was diluted with brine and extracted with EtOAc. The organic layer was dried over MgSO$_4$ filtered and concentrated. The residue was purified on silica gel column (330 g ISCO) eluting with a gradient of 0-30% EtOAc/CH$_2$Cl$_2$. Tubes were collected containing the product, which was concentrated to afford Intermediate S6A (2.394 g, 61% yield) containing about 30% of the (2R,3S) isomer.

Intermediate S6: (R)-2-((R)-2-tert-Butoxy-1-(3-methylisoxazol-4-yl)-2-oxoethyl)-5,5,5-trifluoropentanoic acid In a 200 mL round-bottomed flask a colorless solution of (2R,3R)-1-benzyl 4-tert-butyl 3-(3-methylisoxazol-4-yl)-2-

(3,3,3-trifluoropropyl)succinate (2.4 g, 5.44 mmol) in MeOH (Volume: 50 mL) was treated with Pearlman's Catalyst (0.076 g, 0.544 mmol) and hydrogenated using a hydrogen-filled balloon at room temperature for 1 hour until the reaction was complete (monitored by HPLC). The mixture was filtered through a 0.45 μm membrane and rinsed with MeOH. The filtrated was concentrated to give 2.03 g of crude solid. The solid was purified on Prep HPLC [C18 Luna 30×100 eluting with a gradient from 10% B to 100% B (15 min)] to afford 99% pure Intermediate (896 mg, 46% yield) as a white solid. MS(ES):m/z=352 [M+H$^+$], m/z=350[M−H$^-$]. $^1$H NMR (500 MHz, chloroform-d) δ 8.40 (s, 1H), 3.62 (d, J=10.0 Hz, 1H), 3.08 (td, J=10.0, 3.6 Hz, 1H), 2.34 (s, 3H), 2.33-2.14 (m, 2H), 2.03-1.89 (m, 2H), 1.46 (s, 9H).

Intermediate S7: (R)-2-((R)-2-tert-Butoxy-1-(4-methylisoxazol-3-yl)-2-oxoethyl)-5,5,5-trifluoropentanoic acid

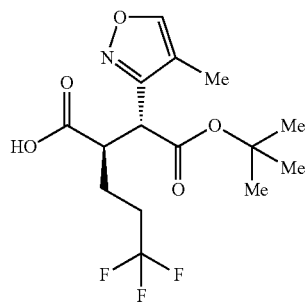

(S7)

Intermediate S7A: 2-(4-Methylisoxazol-3-yl)ethanol

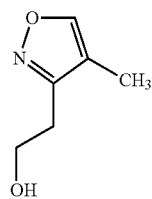

(S7A)

A solution of (Z)-3-(tert-butyldimethylsilyloxy)-N-hydroxypropanimidoyl chloride (90 mg, 0.378 mmol) in ClCH$_2$CH$_2$Cl (Volume: 2 mL) at room temperature was purged with N$_2$ for 2 min. Prop-1-yne (0.022 mL, 0.378 mmol) [Condensed at −78° C.] was added as a liquid, followed by chloro(1,5-cyclooctadiene)(pentamethylcyclopentadienyl)ruthenium (II) (7.17 mg, 0.019 mmol) and triethylamine (0.066 mL, 0.473 mmol). The reaction mixture was stirred at room temperature for 16 h. It was dark brown in color. The mixture was filtered through 0.45 μm membrane. The filtrate was concentrated, diluted with MeOH, and purified with prep HPLC (Waters Xbridge C18 19×100 mm), 20 mL/min flow rate with gradient of 30% B-100% B over 10 minutes Hold at 100% B for 2 min. (A: 0.1% TFA in water/MeOH (90:10), B: 0.1% TFA in water/MeOH (10:90) monitoring at 220 nm. After concentration, 2-(4-methylisoxazol-3-yl)ethanol (35 mg, 0.270 mmol, 71.3% yield) was obtained as light brown liquid. $^1$H NMR (400 MHz, chloroform-d) δ 8.13 (s, 1H), 4.03 (t, J=5.9 Hz, 2H), 2.89 (t, J=5.9 Hz, 2H), 2.02 (d, J=0.9 Hz, 3H).

Intermediate S7B: 2-(4-Methylisoxazol-3-yl)acetic acid

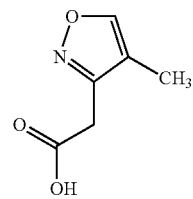

(S7B)

To a solution of 2-(4-methylisoxazol-3-yl)ethanol, Intermediate S7A, (7 mg, 0.055 mmol) in acetone (Volume: 0.5 mL) at room temperature was added 1.35M Jones reagent (0.082 mL, 0.110 mmol). The reaction mixture was stirred at room temperature for 5 h. The mixture was diluted with 2% NaHSO$_3$ and EtOAc. The organic layer was separated and the aqueous layer was extracted with EtOAc (2×). The combined organic layers were washed with brine, dried over MgSO$_4$, filtered and concentrated to afford 2-(4-methylisoxazol-3-yl) acetic acid, Intermediate S7B (6 mg, 0.043 mmol, 77% yield). $^1$H NMR (400 MHz, chloroform-d) δ 8.18 (s, 1H), 3.80 (s, 2H), 2.04 (s, 3H).

Intermediate S7C: tert-Butyl 2-(4-methylisoxazol-3-yl)acetate

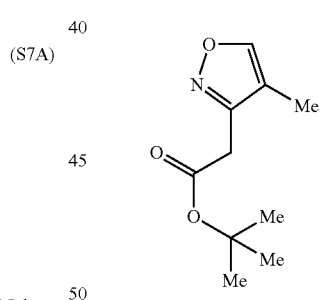

(S7C)

To a solution of 2-(4-methylisoxazol-3-yl)acetic acid, Intermediate S7B (130 mg, 0.921 mmol) in THF (Volume: 2 mL) at 0° C. was added tert-butyl 2,2,2-trichloroacetimidate (403 mg, 1.842 mmol), followed by boron trifluoride ether complex (0.091 mL, 0.737 mmol). The reaction mixture was then warmed to room temperature and stirred at room temperature for 16 h. The reaction mixture was passed through a silica-gel pad, eluted with CH$_2$Cl$_2$. The filtrate was concentrated and hexane was added. The solid was removed by filtration. The filtrate was concentrated and purified with ISCO 24 g column, 30 mL/min monitored at 220 nm. 0-30% EtOAc/hexane in 20 min. The desired product was eluted with 15% EtOAc/hexane. After concentration, tert-butyl 2-(4-methylisoxazol-3-yl)acetate, Intermediate S7C (68 mg, 0.345 mmol, 37.4% yield) was obtained as colorless liquid.

¹H NMR (400 MHz, chloroform-d) δ 8.14 (s, 1H), 3.65 (s, 2H), 2.02 (s, 3H), 1.47 (s, 9H).

Intermediate S7D: (2R,3R)-1-Benzyl 4-tert-butyl 3-(4-methylisoxazol-3-yl)-2-(3,3,3-trifluoropropyl) succinate

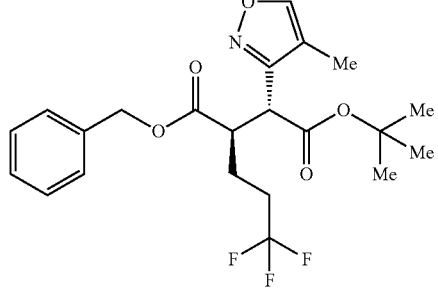

(S7D)

To tert-butyl 2-(4-methylisoxazol-3-yl)acetate (25 mg, 0.127 mmol) (S7C) in a 10 mL round bottomed flask at room temperature was added THF (Ratio: 4.00, Volume: 0.8 mL). The solution was colorless. The solution was stirred at −78° C. 10 min. Next, 0.5 M KHMDS in toluene (0.317 mL, 0.158 mmol) was added slowly. The color of the solution turned to light orange. The mixture was stirred at −78° C. for 10 min and then placed in a room temperature water bath. After 10 minutes, the reaction mixture was put into a −78° C. bath for 20 min. (R)-Benzyl 5,5,5-trifluoro-2-(trifluoromethylsulfonyloxy)pentanoate, Intermediate S5D (65.0 mg, 0.165 mmol) in THF (Ratio: 1.000, Volume: 0.2 mL) was added dropwise. The reaction mixture was stirred at −78° C. for 4 h. The reaction was quenched with saturated aqueous NH₄Cl at −78° C. The mixture was placed in a room temperature water bath and diluted with brine. After 5 minutes, the mixture was extracted with EtOAc. The organic layer was separated and washed with brine, dried over MgSO₄, filtered and concentrated to give a crude material as Intermediate S7D.

Intermediate S7

To Intermediate S7D in MeOH (1 mL) at room temperature was added 10% Pd/C (20 mg). The reaction mixture was purged with H₂ for 3 times and stirred under H₂ balloon for 1 h. The reaction mixture was filtered through a 0.45 μM membrane. The filtrate was concentrated to give a crude material. This crude material was diluted with MeOH and purified with prep HPLC (Waters Xbridge C18 19×100 mm), 20 mL/min flow rate with gradient of 20% B-100% B over 10 minutes. Hold at 100% B for 5 min. (A: 0.1% TFA in water/MeOH (90:10), B: 0.1% TFA in water/MeOH (10:90) monitoring at 220. After concentration, (R)-2-((R)-2-tert-butoxy-1-(4-methylisoxazol-3-yl)-2-oxoethyl)-5,5,5-trifluoropentanoic acid, Intermediate S7 (3 mg, 8.45 μmol, 6.67% yield) was obtained as a white solid. ¹H NMR (500 MHz, methanol-d₄) δ 8.36 (s, 1H), 4.03 (d, J=10.0 Hz, 1H), 3.35 (d, J=10.0 Hz, 1H), 2.43-2.19 (m, 2H), 2.10-2.05 (m, 2H), 2.05 (s, 3H), 1.44 (s, 9H).

Intermediate S8: (2R,3S)-4-tert-Butoxy-2,3-bis(cyclopropylmethyl)-4-oxobutanoic acid

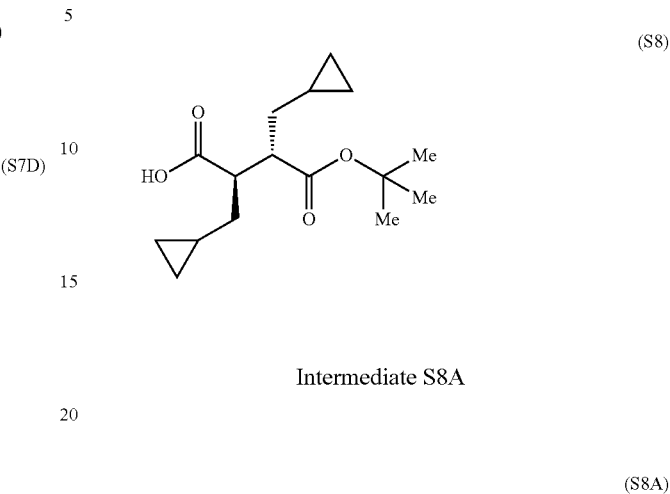

Intermediate S8A

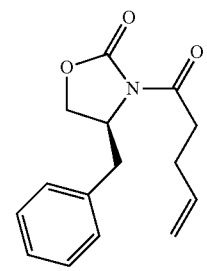

(S8A)

In a 250 mL round-bottomed flask was (S)-4-benzyloxazolidin-2-one (5 g, 28.2 mmol) and THF (30 mL) to give a colorless solution. Cooled in −78° C. bath. 2.5M BuLi in hexane (11.29 mL, 28.2 mmol) was added slowly to the oxazolidinone. Initially a thick white precipitate formed, added another 10 mL THF. At the end of the addition the reaction mixture became light orange and contained white solid material. The reaction mixture was stirred at −78° C. for 1 h, and then pent-4-enoyl chloride (3.11 mL, 28.2 mmol) was added dropwise to the oxazolidinone anion at −78° C. The orange color immediately discharged and the reaction became a pale yellow color. Still several large white chunks in the reaction. After 30 min. The reaction mixture was removed from −78° C. bath and let warm to room temperature. All the white chunks have dissolved. The reaction mixture was then stirred at room temperature for 4 h. The reaction was quenched with saturated NH₄Cl. The reaction mixture was diluted with 10% aqueous LiCl and Et₂O. The organic layer was separated and washed with saturated aqueous NaHCO₃ and then washed with brine. The organic layer was dried over MgSO₄, filtered and concentrated to give a crude material. This crude material was purified on silica gel column (120 g ISCO) eluting with a gradient from 100% hexane/EtOAc to 50% hexane/EtOAc. The product came off ~20% EtOAc/ hexane. The product was collected in tubes and concentrated to afford (S)-4-benzyl-3-(pent-4-enoyl)oxazolidin-2-one, Intermediate S8A (4.35 g, 16.78 mmol, 59.5% yield) as thick colorless oil. ¹H NMR (400 MHz, chloroform-d) δ 7.43-7.22 (m, 5H), 6.01-5.81 (m, 1H), 5.20-5.02 (m, 2H), 4.78-4.62 (m, 1H), 4.29-4.16 (m, 2H), 3.34 (dd, J=13.4, 3.3 Hz, 1H), 3.19-3.02 (m, 2H), 2.80 (dd, J=13.3, 9.6 Hz, 1H), 2.50 (d, J=7.3 Hz, 2H).

Intermediate S8B

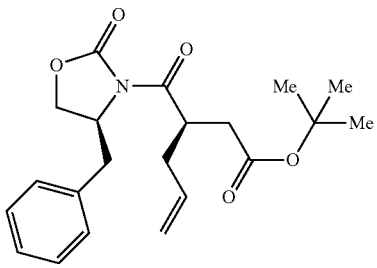

In a 250 mL round-bottomed flask, (S)-4-benzyl-3-(pent-4-enoyl)oxazolidin-2-one, Intermediate S8A (3.35 g, 12.92 mmol) was added to THF (40 mL) to give a colorless solution. The mixture was cooled in −78° C. bath for 10 min. Sodium bis(trimethylsilyl)amide (14.21 mL, 14.21 mmol) was added slowly to the reaction mixture. The reaction mixture turned a light orange color. The reaction mixture was stirred at −78° C. for 2 h. Then tert-butyl 2-bromoacetate (5.04 g, 25.8 mmol) was added slowly. The reaction mixture was stirred at −78° C. for 3 hr. The reaction was quenched with saturated NH$_4$Cl. The mixture was diluted with brine and extracted with Et$_2$O. The organic layer was dried over MgSO$_4$, filtered and concentrated to give a crude material that was purified on silica gel column (120 g ISCO) eluting with a gradient from 0-50% EtOAc/hexane. [The product showed weak UV absorption at 254 nm]. Tubes with product were collected and concentrated to afford (R)-tert-butyl 3-((S)-4-benzyl-2-oxooxazolidine-3-carbonyl)hex-5-enoate, Intermediate S8B (3.2 g, 8.40 mmol, 65.0% yield) as a white solid. $^1$H NMR (400 MHz, chloroform-d) δ 7.40-7.21 (m, 5H), 5.89-5.66 (m, 1H), 5.15-5.03 (m, 2H), 4.73-4.61 (m, 1H), 4.34-4.23 (m, 1H), 4.16 (d, J=5.1 Hz, 2H), 3.35 (dd, J=13.4, 3.1 Hz, 1H), 2.88-2.67 (m, 2H), 2.52-2.38 (m, 2H), 2.28-2.13 (m, 1H), 1.44 (s, 9H).

Intermediate S8C

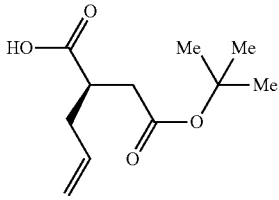

In a 250 mL round-bottomed flask, (R)-tert-butyl 3-((S)-4-benzyl-2-oxooxazolidine-3-carbonyl)hex-5-enoate, Intermediate S8B (3.2 g, 8.57 mmol) was added to THF (30 mL) to give a colorless solution. The mixture was cooled on ice/water bath. In a 100 mL flask, LiOH (0.616 g, 25.7 mmol) was added to water (22 mL) to give a colorless solution. The LiOH mixture was cooled in an ice/water bath. Next, 30% H$_2$O$_2$ in water (2.183 mL, 21.38 mmol) was added to the LiOH mixture. The mixture was stirred at ice/water bath for another 10 min. The LiOH/H$_2$O$_2$ solution was added to the THF solution of starting material. The resulting reaction mixture was stirred in ice/water bath. The reaction was monitored by HPLC and was found to be complete after 30 min. The mixture was stirred for another 1.5 h. Next, 15 mL sat NaHCO$_3$ was added, followed by the addition of ice and the slow addition of 20 mL saturated aqueous Na$_2$SO$_3$ to the mixture. The mixture was maintained at a temperature of less than 15° C. by the addition of ice. The mixture was stirred in the ice/water bath and periodically tested with a peroxide test strip until negative for peroxide. Water was added and the mixture was extracted with CH$_2$Cl$_2$ (3×). The aqueous layer was cooled with ice and acidified slowly with concentrated HCl to pH 4. EtOAc was added and solid NaCl was added very slowly with extensive bubbling. The organic layer was separated and the aqueous layer was twice extracted with EtOAc. The combined organic layers were washed twice with brine and then dried over MgSO$_4$. The layer was filtered and concentrated to afford (R)-2-(2-(tert-butoxy)-2-oxoethyl)pent-4-enoic acid, Intermediate S8C (0.44 g, 2.054 mmol, 86% yield) as a clear colorless oil. $^1$H NMR (400 MHz, chloroform-d) δ 5.84-5.63 (m, 1H), 5.16-5.03 (m, 2H), 2.98-2.84 (m, 1H), 2.66-2.54 (m, 1H), 2.52-2.39 (m, 2H), 2.36-2.24 (m, 1H), 1.44 (s, 9H).

Intermediate S8D

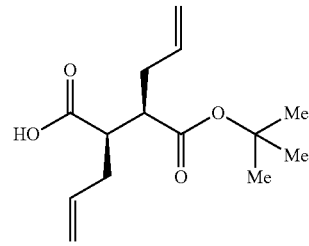

A solution of LDA (9.86 mL, 19.72 mmol) in THF (10 mL) was cooled to −78° C. A solution of (R)-2-(2-(tert-butoxy)-2-oxoethyl)pent-4-enoic acid, Intermediate S8C (1.69 g, 7.89 mmol) in THF (10 ml) was added over 30 min which maintaining the temperature below −73° C.). After the addition was complete, the mixture was stirred at −78° C. for 2 h. To this was added 3-bromoprop-1-ene (1.431 g, 11.83 mmol) over 15 min. The amber mixture was stirred with a cooling bath and allowed to slowly warm to ambient temperature and stirred under N$_2$ for 16 h. After 16 h, monitoring using LC/MS indicated the reaction mixture contained the desired product (M+Na 277.3) with estimated ~6% of allyl ester (M+Na=317.3). No starting material was detected. To the reaction mixture was added ice and the pH was adjusted to ~1 with 1N HCl. Saturated with NaCl was added and the mixture was extracted with EtOAc. The combined extracts were washed with brine (3×80 mL), dried over MgSO$_4$, evaporated, dried in vacuo to afford (2R,3R)-2-allyl-3-(tert-butoxycarbonyl)hex-5-enoic acid, Intermediate S8D (2.0 g, 7.86 mmol, 100% yield)$^1$H NMR (400 MHz, chloroform-d) δ 5.74 (ddd, J=17.1, 10.1, 7.2 Hz, 2H), 5.20-4.99 (m, 4H), 2.78 (dd, J=7.8, 5.6 Hz, 1H), 2.73-2.65 (m, 1H), 2.50-2.30 (m, 4H), 1.50-1.39 (m, 9H).

Intermediate S8E

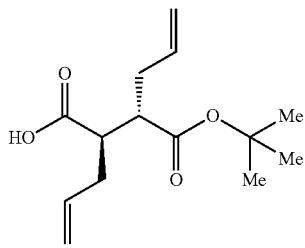

To a solution of (2R,3R)-2-allyl-3-(tert-butoxycarbonyl)hex-5-enoic acid, Intermediate S8D (2 g, 7.86 mmol) in THF (30 mL) under nitrogen at −78° C. was added 2 M LDA (8.65 mL, 17.30 mmol) dropwise through syringe. The temperature was maintained below −70° C. After the addition was complete, the reaction mixture was allowed to warm up in a water bath to room temperature. The reaction mixture was maintained at room temperature for 15 min. Then the reaction mixture was cooled to −78° C. The reaction mixture was charge with 1M diethylaluminum chloride in hexane (19.66 mL, 19.66 mmol) dropwise through syringe. The temperature of the reaction mixture was maintained below −70° C. After the addition was complete, the reaction mixture was warmed in a water bath to room temperature and maintained at room temperature for 15 min. Next, the mixture was cooled to −78° C. A solution of methanol (60 mL) was prepared and cooled to −78° C. The reaction mixture was transferred in to the methanol solution through a cannula by nitrogen pressure. After the transfer was complete, 20 g of ice was added to the reaction mixture, followed by the slow addition of 1N HCl (60 mL). Vigorous foaming was observed after ⅔ acid was added. The temperature increased to −10 to −20° C. The reaction mixture was stirred until off gassing subsided. Next, EtOAc (100 mL) was added and the reaction mixture was stirred for 5 min. The organic layer was separated and washed with KF solution (4.13 g in 100 mL water) and 1N HCl (20 mL), brine, and dried over $Na_2SO_4$. The mixture was filtered and concentrated on a rotovap to obtain Intermediate S8E (2.0 g (100% yield)) as a brown liquid. $^1$H NMR (400 MHz, chloroform-d) δ 5.84-5.65 (m, 2H), 5.15-4.95 (m, 4H), 2.72 (ddd, J=13.0, 8.9, 4.5 Hz, 2H), 2.48-2.34 (m, 2H), 2.34-2.19 (m, 2H), 1.45 (s, 9H).

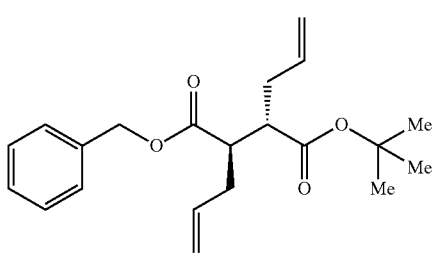

Intermediate S8F

To a solution of (2R)-2-allyl-3-(tert-butoxycarbonyl)hex-5-enoic acid, Intermediate S8E (1.8 g, 7.08 mmol) (anti:syn 4:1) in DMF (20 mL) at room temperature was added potassium carbonate (1.956 g, 14.16 mmol), followed by (bromomethyl)benzene (1.010 mL, 8.49 mmol). The reaction mixture was stirred at room temperature for 3 h and filtered to remove solid material. The filtrate was diluted with EtOAc and water. The organic layer was separated and washed with water, brine, dried over $MgSO_4$, filtered, and concentrated to give a crude material. This crude material was purified with ISCO 80 g column, 60 mL/min. 0-20% EtOAc/hexane in 25 min to afford (2R,3S)-1-benzyl 4-tert-butyl 2,3-diallylsuccinate, Intermediate S8F (1.5 g, 4.35 mmol, 61.5% yield) as a colorless liquid. $^1$H NMR (400 MHz, chloroform-d) δ 7.43-7.31 (m, 5H), 5.81-5.62 (m, 2H), 5.17-5.08 (m, 2H), 5.08-4.96 (m, 4H), 2.84-2.63 (m, 2H), 2.45-2.23 (m, 3H), 2.18 (d, J=1.5 Hz, 1H), 1.43 (s, 9H).

Intermediate S8G

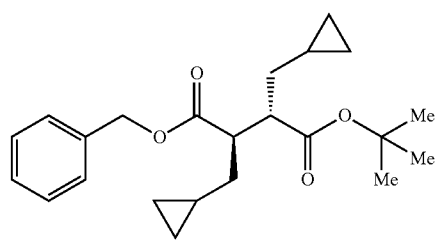

Diazomethane was prepared as follows: To a mixture of 40% KOH [KOH (12 g, 53.5 mmol) in water (30 mL)] and $Et_2O$ (30 mL) cooled to 0° C. was added N-methyl-N'-nitro-N-nitrosoguanidine (4.27 g, 29.0 mmol) portionwise. The resulting solution was swirled several times. The ether layer (yellow solution) was pipetted into a mixture of (2R,3S)-1-benzyl 4-tert-butyl 2,3-diallylsuccinate, Intermediate S8F (0.500 g, 1.452 mmol) and $Pd(OAc)_2$ (0.033 g, 0.145 mmol) in $Et_2O$ (20 mL) at 0° C. The color of the solution changed from light brown to darker brown. The mixture was stirred at 0° C. for 1 h. The mixture was filtered through CELITE® and the filtrate was concentrated to afford (2R,3S)-1-benzyl 4-tert-butyl 2,3-bis(cyclopropylmethyl)succinate, Intermediate S8G (0.530 g, 1.423 mmol, 98% yield) as a light yellow liquid. $^1$H NMR (400 MHz, chloroform-d) δ 7.42-7.31 (m, 5H), 5.23-5.01 (m, 2H), 2.79-2.71 (m, 1H), 2.66 (dd, J=10.2, 3.9 Hz, 1H), 1.71-1.54 (m, 2H), 1.45 (s, 9H), 1.38-1.22 (m, 2H), 0.80-0.62 (m, 2H), 0.51-0.36 (m, 4H), 0.16-0.05 (m, 2H), 0.05--0.02 (m, 2H).

Intermediate S8

To a solution of (2R,3S)-1-benzyl 4-tert-butyl 2,3-bis(cyclopropylmethyl)succinate, Intermediate S8G (0.530 g, 1.423 mmol) in MeOH (10 mL) was added 10% Pd/C (Degussa) (0.300 g, 1.423 mmol). The reaction mixture was evacuated with vacuum and filled with $H_2$ (Repeated this for 3×). Next, the reaction mixture was stirred under $H_2$ balloon for 1.5 h, evacuated, and filled with $N_2$. The mixture was then filtered through CELITE®. The filtrate was concentrated to afford (2R,3S)-4-(tert-butoxy)-2,3-bis(cyclopropylmethyl)-4-oxobutanoic acid, Intermediate S8 (0.400 g, 1.417 mmol, 100% yield) as a colorless liquid. $^1$H NMR (400 MHz, chloroform-d) δ 2.69 (td, J=9.9, 3.7 Hz, 2H), 1.71-1.54 (m, 2H), 1.47 (s, 9H), 1.38-1.22 (m, 2H), 0.80-0.62 (m, 2H), 0.51-0.36 (m, 4H), 0.16-0.05 (m, 2H), 0.05--0.02 (m, 2H).

Intermediate S9: (2R,3S)-3-(tert-Butoxycarbonyl)-6,6,6-trifluoro-2-propylhexanoic acid

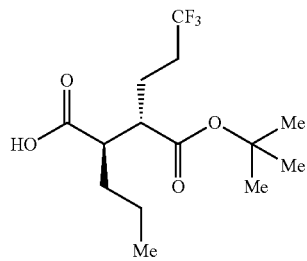

(S9)

Intermediate S9A

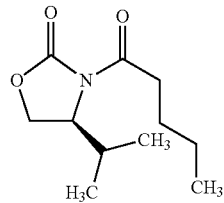

(S9A)

To a stirred solution of pentanoic acid (5.98 g, 58.6 mmol) in CH$_2$Cl$_2$ (100 mL) and 10 drops DMF was added oxalyl chloride (5.64 mL, 64.4 mmol) dropwise over 5 min and the solution stirred for 2.75 h, at which time all bubbling subsided. The solution was concentrated in vacuo. In a separate flask, to a cold (−78° C.), stirred solution of (S)-4-isopropyloxazolidin-2-one (7.56 g, 58.6 mmol) in THF (280 mL) was added n-BuLi (2.5M in hexane, 23.42 mL, 58.6 mmol) dropwise via addition funnel over 20 min (temperature never exceeded −68° C.). After stirring 10 min, the above acid chloride dissolved in THF (50 mL) was added via addition funnel over 25 min. After the addition was complete, the reaction mixture was allowed to warm to room temperature and stirred overnight. Water was added to the reaction mixture. The mixture was transferred to a separatory funnel and extracted with EtOAc (2×). The combined organic layers were washed with brine, dried (Na$_2$SO$_4$), filtered and concentrated to an amber oil. The residue was purified by flash chromatography (Teledyne ISCO CombiFlash Rf, 0% to 60% solvent A/B=hex/EtOAc, REDISEP® SiO$_2$ 120 g, applied as a DCM solution) to afford ((S)-4-isopropyl-3-pentanoyloxazolidin-2-one (6.51 g, 52%) as a colorless oil. $^1$H NMR (400 MHz, chloroform-d) δ ppm 4.44 (1H, ddd, J=8.16, 3.51, 3.39 Hz), 4.27 (1H, t, J=9.00 Hz), 4.21 (1H, dd, J=9.00, 3.01 Hz), 2.99 (1H, ddd, J=16.60, 8.50, 6.50 Hz), 2.86 (1H, ddd, J=16.60, 8.50, 6.78 Hz), 2.31-2.44 (1H, m), 1.56-1.72 (2H, m), 1.39 (2H, sxt, J=7.43 Hz), 0.94 (3H, t, J=7.28 Hz), 0.92 (3H, d, J=7.03 Hz), 0.88 (3H, d, J=6.78 Hz); HPLC: RT=2.497 min (CHROMOLITH® SpeedROD 4.6×50 mm (4 min grad) eluting with MeOH/H2O/0.1% TFA, 4 mL/min, monitoring at 220 nm); purity=100%.

Intermediate S9B

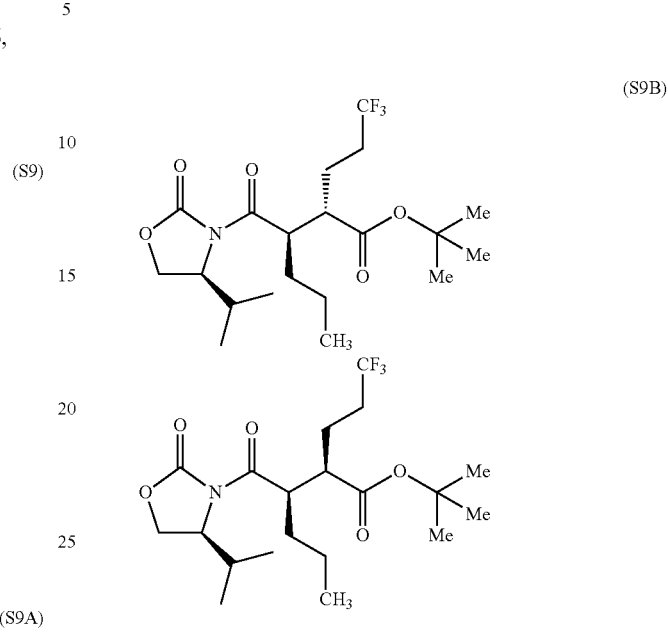

(S9B)

To a cold (−78° C.), stirred solution of diisopropylamine (5.4 mL, 37.9 mmol) in THF (60 mL) under nitrogen atmosphere was added n-BuLi (2.5M in hexane, 15 mL, 37.5 mmol). The mixture was warmed to 0° C. to give a 0.5M solution of LDA. A separate vessel was charged with oxazolidinone SM (1.99 g, 9.33 mmol), then toluene (15.3 mL) was added. This solution was added to a flask containing dry lithium chloride (2.05 g, 48.4 mmol). To the resultant mixture, cooled to −78° C., was added LDA solution (21.5 mL, 10.75 mmol) and stirred at −78° C. for 10 min, warmed to 0° C. for 10 min and then recooled to −78° C. To a separate reaction vessel containing tert-butyl 5,5,5-trifluoropentanoate (3.46 g, 16.30 mmol), was added toluene (15.3 mL), cooled to −78° C. and LDA (37.5 mL, 18.75 mmol) was added, the resulting solution was stirred at −78° for 25 min. At this time the enolate derived from the ester was transferred via cannula into the solution of the oxazolidinone enolate, stirred at −78° C. for an additional 5 min at which time the septum was removed and solid powdered bis(2-ethylhexanoyloxy) copper (9.04 g, 25.8 mmol) was rapidly added to the reaction vessel and the septum replaced. The vessel was immediately removed from the cold bath and immersed into a warm water bath (40° C.) with rapid swirling with a concomitant color change from the initial turquoise to brown. The reaction mixture was stirred for 25 min, was poured into 5% aqueous NH$_4$OH (360 mL) and extracted with EtOAc (2×). The combined organics were washed with brine, dried (Na$_2$SO$_4$), filtered and concentrated under reduced pressure. The residue was purified by flash chromatography (Teledyne ISCO CombiFlash Rf, 0% to 60% solvent A/B=hexanes/EtOAc, REDISEP® SiO$_2$ 120 g). Concentration of appropriate fractions provided a mixture of Intermediate S9B (1.92 g, 49%) as a pale yellow viscous oil. $^1$H NMR showed the product was a 1.45:1 mixture of diastereomers I1C:I1D as determined by the integration of the t-Bu singlets at 1.47 and 1.44 ppm: $^1$H NMR (400 MHz, chloroform-d) δ 4.48 (dt, J=7.8, 3.5 Hz, 1H), 4.44 (dt, J=7.7, 3.4 Hz, 1H), 4.33-4.19 (m, 3H), 4.06 (ddd, J=10.3, 7.0, 3.5 Hz, 1H), 2.83 (td, J=8.3, 4.4 Hz, 1H), 2.67 (ddd, J=10.5, 7.0, 3.9 Hz, 1H), 2.49-1.93 (m, 8H), 1.91-1.80 (m, 2H), 1.79-1.55 (m, 5H), 1.47 (s, 9H, major diastereomer), 1.44 (s, 9H, minor diastereomer), 0.98-0.85 (m, 18H).

Intermediate S9C

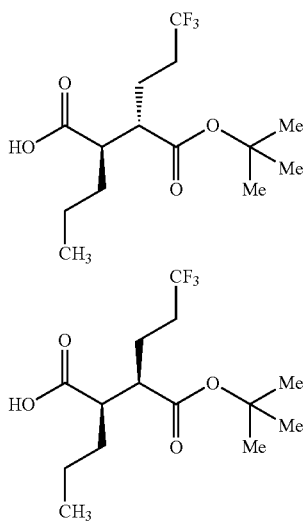

(S9C)

To a cool (0° C.), stirred solution of (3R)-tert-butyl 3-((S)-4-isopropyl-2-oxooxazolidine-3-carbonyl)-2-(3,3,3-trifluoropropyl)hexanoate (1.92 g, 4.53 mmol) in THF (67 mL) and water (20 mL) were added H$_2$O$_2$ (30% in water, 4.93 g, 43.5 mmol) followed by LiOH (329.0 mg, 13.74 mmol). After 60 min, the reaction mixture was warmed to room temperature, then after an additional 60 min, to the reaction mixture was added ice (to control exotherm), saturated NaHCO$_3$ (15 mL) and saturated Na$_2$SO$_3$ (15 mL). The mixture was partially concentrated in vacuo, extracted with twice with DCM (100 mL). The aqueous phase was acidified (to pH-1-2) with 1N HCl, saturated with NaCl, extracted with DCM (3×100) and EtOAc (1×100), the extracts were combined, dried (MgSO$_4$), filtered and concentrated to afford Intermediate S9C (666.3 mg, 47%) as a colorless oil. $^1$H NMR showed 1.83:1 mixture of diastereomers (integration of t-Bu peaks): $^1$H NMR (400 MHz, chloroform-d) δ 2.78-2.54 (m, 4H), 2.29-1.99 (m, 4H), 1.97-1.79 (m, 3H), 1.78-1.49 (m, 5H), 1.47 (s, 9H, minor diastereomer), 1.45 (s, 9H, major diastereomer), 1.44-1.17 (m, 4H), 0.98-0.85 (m, 6H).

Intermediate S9D

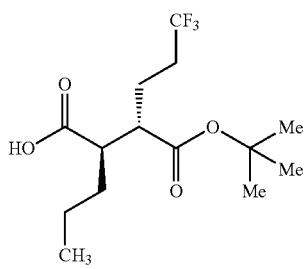

(S9D)

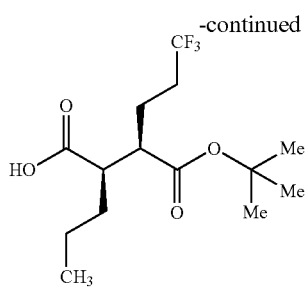

To a cold (−78° C.), stirred solution of (2R,3S)-3-(tert-butoxycarbonyl)-6,6,6-trifluoro-2-propylhexanoic acid (4.75 g, 15.21 mmol) in THF (84 mL) under N$_2$ was added LDA (1.8M, 20.3 mL, 36.5 mmol) dropwise over 10 min (internal temperature never exceeded −68° C.), stirred for 15 min, warmed to room temperature (24° C. water bath), stirred for 15 min, and cooled to −78° C. for 15 min. To the reaction mixture was added Et$_2$AlCl (1M in hexane, 32.0 mL, 32.0 mmol) via syringe, stirred for 10 min, warmed to room temperature (24° C. bath) for 15 min, and then back to −78° C. for 25 min. Meanwhile, a flask containing MeOH (140 mL) was cooled to −78° C. The reaction solution was rapidly transferred to the MeOH via cannula, removed from bath then ice and 1N HCl (137 mL, 137 mmol) was added slowly. Gas evolution with bubbling and foaming occurred. The mixture was extracted with EtOAc (2×300 mL), the combined organics washed with a solution of potassium fluoride (7.95 g, 137 mmol) in water (300 mL) and 1N HCl (38 mL, 38.0 mmol), brine then dried (Na$_2$SO$_4$), filtered and concentrated to a golden yellow oil. $^1$H NMR showed the product was 7.58:1 mixture of desired diastereomer. Obtained the Intermediate S9D (4.70 g, 99%) as a dark amber viscous oil: $^1$H NMR (400 MHz, chloroform-d) δ 1.47 (s, 9H, major diastereomer), 1.45 (s, 9H, minor diastereomer).

Intermediate S9E

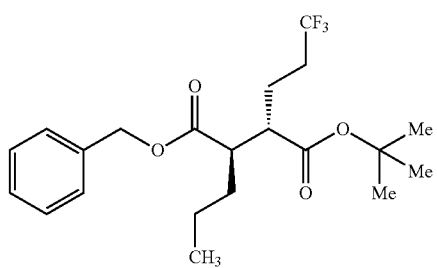

(S9E)

To a stirred solution of (2R,3S)-3-(tert-butoxycarbonyl)-6,6,6-trifluoro-2-propylhexanoic acid (4.70 g, 15.05 mmol) and benzyl bromide (2.2 mL, 18.50 mmol) in DMF (55 mL) was added potassium carbonate (3.16 g, 22.86 mmol). After 8.5 h, the reaction mixture was diluted with EtOAc (300 mL), washed with 10% LiCl (3×100 mL), sat NaCl, dried (Na$_2$SO$_4$), filtered and concentrated. The residue was purified by flash chromatography (Teledyne ISCO CombiFlash Rf, 50% to 80% solvent A/B=hexanes/toluene, REDISEP® SiO$_2$ 330 g Gold) to afford Intermediate S9D (4.9 g, 81%). $^1$H NMR (400 MHz, chloroform-d) δ 7.30-7.42 (m, 5H), 5.17 (d, J=12.10 Hz, 1H), 5.13 (d, J=12.10 Hz, 1H), 2.65-2.73 (m, 1H), 2.57 (dt, J=3.52, 9.79 Hz, 1H), 1.93-2.17 (m, 2H), 1.80

(dtd, J=5.17, 10.51, 13.64 Hz, 1H), 1.58-1.73 (m, 2H), 1.45 (s, 9H), 1.16-1.43 (m, 3H), 0.85-0.91 (m, 3H).

Intermediate S9

A solution of (2R,3S)-1-benzyl 4-tert-butyl 2-propyl-3-(3,3,3-trifluoropropyl)succinate (4.9 g, 12.18 mmol) in MeOH (60 ml) was treated with activated carbon, filtered through CELITE®, and washed with MeOH (60 ml). This solution was purged with vacuum/N$_2$ (3×), 10% palladium on carbon (wet, Degussa type, 328.1 mg, 0.308 mmol) was added, purged 3× with N$_2$, then purged with H$_2$ (balloon, 3×), and stirred. After 4.5 h, the reaction mixture was purged with N$_2$ (3×), filtered through CELITE®, washed with MeOH, concentrated, and dried under vacuum overnight. Obtained Intermediate S9 (3.45 g, 91%) as a colorless oil. $^1$H NMR (400 MHz, chloroform-d) δ 2.71-2.64 (m, 1H), 2.63-2.56 (m, 1H), 2.26-2.00 (m, 2H), 1.90 (dtd, J=13.7, 10.3, 5.3 Hz, 1H), 1.78-1.61 (m, 2H), 1.48 (s, 9H), 1.46-1.38 (m, 2H), 1.37-1.23 (m, 1H), 0.93 (t, J=7.0 Hz, 3H).

Intermediate A-1: (S)-9-Amino-6,6-difluoro-11-phenyl-6,7-dihydro-5H-4-oxa-7a,10-diazabenzo[ef]heptalen-8(9H)-one

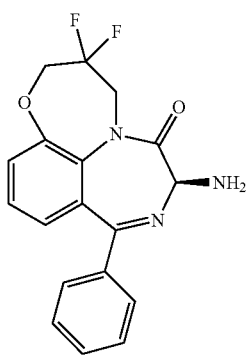

(A-1)

Intermediate A-1A:
8-Methoxy-2-methyl-4H-benzo[d][1,3]oxazin-4-one

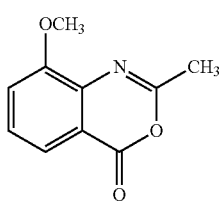

(A-1A)

To a 100 mL round-bottomed flask, 2-amino-3-methoxybenzoic acid (10.1 g, 60.4 mmol) and acetic anhydride (50 ml, 530 mmol) were added to give a suspension. The mixture was heated to 140° C. with stirring for 180 min. The reaction mixture was cooled to room temperature and concentrated to provide 8-methoxy-2-methyl-4H-benzo[d][1,3]oxazin-4-one (11.51 g, 100%): $^1$H NMR (400 MHz, DMSO-d$_6$) δ 7.59 (dd, J=6.9, 2.3 Hz, 1H), 7.52-7.42 (m, 2H), 3.89 (s, 3H), 2.39 (s, 3H); HPLC: RT=0.795 min (H$_2$O/MeOH with TFA, Sunfire C18 2.5 μm, 2.1×30 mm, gradient=2 min, wavelength=220 nm); MS(ES): m/z=292 [M+H]$^+$.

Intermediate A-1B:
(2-Amino-3-methoxyphenyl)(phenyl)methanone

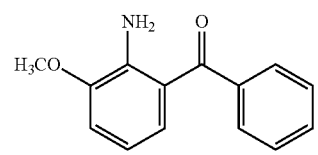

(A-1B)

A 100 mL round-bottomed flask containing 8-methoxy-2-methyl-4H-benzo[d][1,3]oxazin-4-one, Intermediate A-1A (1 g, 5.23 mmol) in diethyl ether (20 mL), toluene (10 mL) and THF (10 mL) was cooled to 0° C. Phenyl magnesium bromide (1.9 mL, 5.75 mmol, 3M in Et$_2$O) was added in one portion. The reaction mixture was allowed to warm to room temperature and stirred overnight. The reaction mixture was cooled to 0° C. and 30 g crushed ice and 25 ml 6N HCl were added. The reaction mixture was allowed to slowly warm to room temperature. The reaction mixture was partitioned with ethyl acetate (100 mL) and brine (50 mL). The aqueous phase was separated and extracted with ethyl acetate (1×100 mL). The combined organic layers were dried (MgSO$_4$), filtered and concentrated. The residue was purified by silica gel chromatography to provide 882 mg colorless solid. This material was dissolved in AcOH (10 mL) and treated with concentrated HCl (6 mL, 72.0 mmol), then heated to 100° C. with stirring overnight. The mixture was cooled to room temperature, concentrated and dried under vacuum. The residue was diluted with ethyl acetate (100 mL), the pH was adjusted to pH 10 with saturated NaHCO$_3$, and then the phases separated. The aqueous phase was extracted with ethyl acetate (2×50 mL), the combined organic phases were dried (MgSO$_4$), filtered and concentrated. The residue was purified by silica gel chromatography (EtOAc/hexane) to provide (2-Amino-3-methoxyphenyl)(phenyl) methanone, Intermediate A-1B (370 mg, 31%): $^1$H NMR (400 MHz, DMSO-d$_6$) δ 9.43 (br. s., 2H), 7.70-7.63 (m, 1H), 7.33-7.22 (m, 5H), 7.10-7.03 (m, 1H), 6.91 (dd, J=6.7, 2.1 Hz, 1H), 3.87 (s, 3H): HPLC: RT=1.888 min (H$_2$O/MeOH with TFA, Sunfire C18 2.5 μm, 2.1×30 mm, gradient=2 min, wavelength=220); MS(ES): m/z=228[M+H]$^+$.

Intermediate A-1C: Benzyl 9-methoxy-2-oxo-5-phenyl-2,3-dihydro-1H-benzo[e][1,4]diazepin-3-ylcarbamate

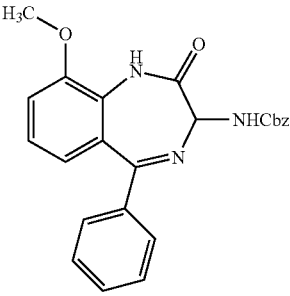

(A-1C)

To a stirred suspension of 2-(1H-benzo[d][1,2,3]triazol-1-yl)-2-(benzyloxycarbonylamino)acetic acid (1.08 g, 3.31 mmol) in CH$_2$Cl$_2$ (Ratio: 4.00, Volume: 20 mL) and DMF (5 drops) at room temperature was added oxalyl chloride (0.31 mL, 3.54 mmol). The reaction mixture was stirred at 0° C. for 20 min. The above solution was transferred to an addition funnel, then was added dropwise over 25 min to a cool (0° C.), stirred solution of (2-amino-3-methoxyphenyl)(phenyl)methanone, Intermediate A-1B (379.3 mg, 1.669 mmol) and triethyl amine (0.52 mL, 3.73 mmol) in CH$_2$Cl$_2$ (5 mL). The reaction mixture was removed from the ice bath after 30 min and stirred at room temperature for 1 h. The mixture was washed with saturated NaHCO$_3$ and brine, then dried (MgSO$_4$), filtered and partially concentrated to ~10 mL. To this was added MeOH (40 mL) and the mixture was partially concentrated to 20 mL. Ammonia (2.0M in MeOH) (5.0 mL, 10.00 mmol) was added to the stirring methanolic solution. The mixture was stirred for 16 h. AcOH (20 mL) was added and the mixture was stirred at room temperature for 5 h. The reaction mixture was then concentrated, the residue was dissolved in CH$_2$Cl$_2$ and water, brought to pH ~9-10 with 1M NaOH. The organic phase was separated, washed with brine, dried (MgSO$_4$), filtered and concentrated. The residue was purified by flash chromatography (Teledyne ISCO Combi-Flash Rf, 0% to 100% solvent A/B=1:1 heptane:DCM/EtOAc, REDISEP® SiO$_2$ 80 g, loaded as DCM solution). Fractions containing product were collected and concentrated to afford (benzyl 9-methoxy-2-oxo-5-phenyl-2,3-dihydro-1H-benzo[e][1,4]diazepin-3-ylcarbamate, Intermediate A-1C (529.6 mg, 1.275 mmol, 76% yield)) as a pale yellow solid: $^1$H NMR (400 MHz, chloroform-d) δ ppm 7.98 (1H, s), 7.55 (2H, d, J=7.0 Hz), 7.29-7.50 (8H, m), 7.10-7.19 (1H, m), 7.03-7.09 (1H, m), 6.94 (1H, dd, J=7.9, 1.1 Hz), 6.60 (1H, d, J=8.4 Hz), 5.34 (1H, d, J=8.4 Hz), 5.18 (2H, s), 3.97 (3H, s).

Intermediate A-1D: 3-Amino-9-hydroxy-5-phenyl-1H-benzo[e][1,4]diazepin-2(3H)-one

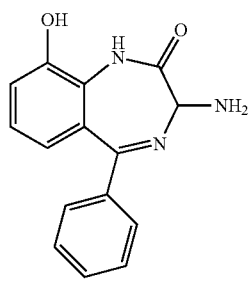

(A-1D)

To a solution of benzyl 9-methoxy-2-oxo-5-phenyl-2,3-dihydro-1H-benzo[e][1,4]diazepin-3-ylcarbamate A-1C (9 g, 21.66 mmol) in CH$_2$Cl$_2$ (Volume: 100 mL) at room temperature was added 1 M BBr$_3$ (76 ml, 76 mmol) slowly. The mixture became a yellow suspension. The reaction mixture was stirred at room temperature for 16 h. MeOH was added and the mixture became a clear solution. The mixture was stirred at room temperature for 1 h. Then solvent was removed. This was repeated 3 times to afford a light brown residue. To this residue was added Et$_2$O and the mixture was allowed to sit for 30 min. A precipitate formed and was filtered to collect solid. The solid was dissolved in MeOH and concentrated again. Et$_2$O was added and precipitate was collected by filtration and left on vacuum for 16 h. 3-amino-9-hydroxy-5-phenyl-1H-benzo[e][1,4]diazepin-2(3H)-one, HBr salt, Intermediate A-1D (9.2 g, 19.78 mmol, 91% yield) was obtained as a yellow solid. $^1$H NMR (400 MHz, DMSO-d$_6$) δ ppm 10.34 (1H, s), 8.95 (3H, d, J=3.3 Hz), 7.47-7.65 (5H, m), 7.03-7.25 (2H, m), 6.72 (1H, dd, J=7.7, 1.3 Hz), 5.04 (1H, d, J=4.8 Hz) LC-MS: M+H=268.2.

Intermediate A-1E: tert-Butyl 9-hydroxy-2-oxo-5-phenyl-2,3-dihydro-1H-benzo[e][1,4]diazepin-3-ylcarbamate

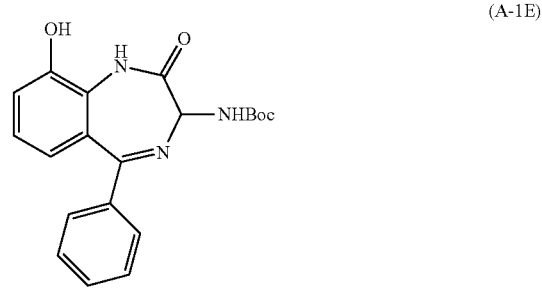 [SMILES: CC(C)(C)OC(=O)NC1N=C(c2ccccc2)c2cccc(O)c2NC1=O]

(A-1E)

To a suspension of 3-amino-9-hydroxy-5-phenyl-1H-benzo[e][1,4]diazepin-2(3H)-one, Intermediate A-1D (8.3 g, 19.39 mmol) in dioxane (Volume: 10 mL) at room temperature was added di-t-butyldicarbonate (5.80 mL, 25.2 mmol), followed by triethyl amine (7.03 mL, 50.5 mmol). The mixture became a clear solution and then precipitate formed. The suspension was stirred at room temperature for 4 h, and then filtered to collect the solid material. The filtrate was predominately bis product with a minor yield of the desired product. The solid material was added to water, MeOH, and EtOAc. The solid was partially dissolved. This undissolved solid was dried under vacuum for 48 h to give 4.5 g of white solid. The filtrate was transferred to a reparatory funnel and the organic layer was separated and washed with water and brine, concentrated to give crude solid. This solid was added to MeOH and collected by filtration to afford tert-butyl 9-hydroxy-2-oxo-5-phenyl-2,3-dihydro-1H-benzo[e][1,4]diazepin-3-ylcarbamate, Intermediate A-1E 5.2 g (0.75 g) as a white solid. Total. $^1$H NMR (400 MHz, DMSO-d$_6$) δ 6.76-6.65 (m, 3H), 6.65-6.54 (m, 2H), 6.34-6.19 (m, 2H), 5.96 (dd, J=6.9, 1.9 Hz, 1H), 4.38-4.27 (m, 1H), 2.90-2.77 (m, 3H), 0.69 (s, 9H).

Intermediate A-1F: tert-Butyl(6,8-dioxo-11-phenyl-6,7,8,9-tetrahydro-5H-4-oxa-7a,10-diazabenzo[ef]heptalen-9-yl)carbamate

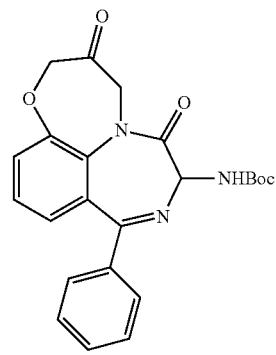

(A-1F)

To a solution of tert-butyl 9-hydroxy-2-oxo-5-phenyl-2,3-dihydro-1H-benzo[e][1,4]diazepin-3-ylcarbamate, Intermediate A1-E (7.6 g, 19.65 mmol) in DMF (Volume: 100 mL) at room temperature were added cesium carbonate (16.01 g, 49.1 mmol), followed by 1,3-dibromopropan-2-one (16.97 g, 59.0 mmol). The reaction mixture was stirred at room temperature for 4 h, and then filtered to remove the solid material. The solid material was rinsed with DMF and discarded. The filtrate was diluted with water, and precipitate formed. EtOAc was added and the organic layer was separated and the aqueous layer was extracted with EtOAc (6×). The combined organic layer was washed with brine, dried over MgSO$_4$, filtered and concentrated to give a brown liquid. This material was separated into two portions and purified with ISCO separately. 220 g column, 150 mL/min. 0-100% EtOAC/hexane in 30 min. The desired product was eluted with about 45% EtOAc/hexane to afford tert-butyl(6,8-dioxo-11-phenyl-6,7,8,9-tetrahydro-5H-4-oxa-7a,10-diazabenzo[ef]heptalen-9-yl)carbamate, Intermediate A-1F (6.0 g, 71%) as an off-white solid. $^1$H NMR (400 MHz, chloroform-d) δ 7.72-7.58 (m, 2H), 7.48 (d, J=7.5 Hz, 1H), 7.45-7.35 (m, 2H), 7.27-7.23 (m, 1H), 7.10 (dd, J=6.7, 2.3 Hz, 1H), 6.34 (d, J=8.6 Hz, 1H), 5.51 (d, J=8.6 Hz, 1H), 5.01-4.83 (m, 2H), 4.48 (d, J=15.4 Hz, 1H), 4.32 (d, J=15.8 Hz, 1H), 1.54-1.44 (m, 9H).

Intermediate A-1G: tert-Butyl(6,6-difluoro-8-oxo-11-phenyl-6,7,8,9-tetrahydro-5H-4-oxa-7a,10-diazabenzo[ef]heptalen-9-yl)carbamate

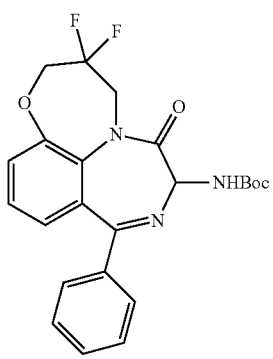

(A-1G)

To a solution of tert-butyl(6,8-dioxo-11-phenyl-6,7,8,9-tetrahydro-5H-4-oxa-7a,10-diazabenzo[ef]heptalen-9-yl)carbamate, Intermediate A-1F (6.0 g, 14.24 mmol) at 0° C. was added diethylaminosulfur trifluoride (13.77 g, 85 mmol). The reaction mixture was stirred at room temperature for 16 h. The reaction mixture was diluted with CH$_2$Cl$_2$ and poured slowly into saturated aqueous NaHCO$_3$ with the formation of bubbles. The mixture was allowed to stir for 10 min. The organic layer was separated and washed with brine, dried over MgSO$_4$, filtered and concentrated to give a crude material. This crude material was purified with ISCO 220 g 150 mL/min. 0-50% EtOAc/hexane in 30 min to give tert-butyl (6,6-difluoro-8-oxo-11-phenyl-6,7,8,9-tetrahydro-5H-4-oxa-7a,10-diazabenzo[ef]heptalen-9-yl)carbamate, Intermediate A-1G (3.8 g, 48%) as a yellow solid. $^1$H NMR (400 MHz, chloroform-d) δ 7.67-7.58 (m, 2H), 7.54-7.39 (m, 3H), 7.28-7.20 (m, 1H), 7.11 (dd, J=7.5, 1.8 Hz, 1H), 6.47 (d, J=8.8 Hz, 1H), 5.57-5.47 (m, 1H), 5.09 (dd, J=14.5, 11.9 Hz, 1H), 4.66-4.44 (m, 1H), 4.43-4.26 (m, 1H), 3.77-3.52 (m, 1H), 1.54-1.46 (m, 9H).

Intermediate A-1H: (S)-tert-Butyl(6,6-difluoro-8-oxo-11-phenyl-6,7,8,9-tetrahydro-5H-4-oxa-7a,10-diazabenzo[ef]heptalen-9-yl)carbamate

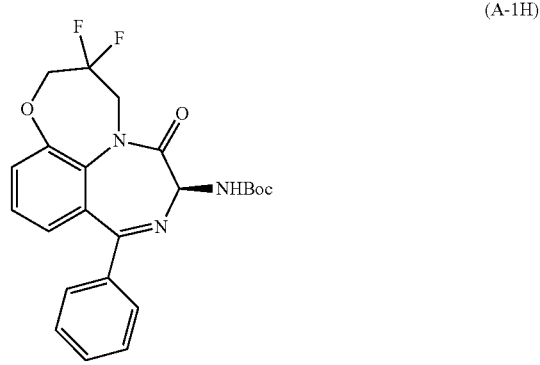 [SMILES: CC(C)(C)OC(=O)N[C@H]1N=C(c2ccccc2)c2cccc3c2N(CC(F)(F)CO3)C1=O]

(A-1H)

Intermediate A-1G (3.8 g, 6.86 mmol) was resolved by chiral SFC (Instrument: Berger SFC MGII, Column: CHIRALPAK® OJ-H 25×5 cm, 5 μm; column temp: 40° C.; Mobile Phase: CO$_2$/MeOH (90/10); Flow rate: 280 mL/min; Detection at 220 nm.) to afford (S)-tert-butyl(6,6-difluoro-8-oxo-11-phenyl-6,7,8,9-tetrahydro-5H-4-oxa-7a,10-diazabenzo[ef]heptalen-9-yl)carbamate, Intermediate A-1H (0.87 g, 28%)$^1$H NMR (400 MHz, chloroform-d) δ 7.67-7.56 (m, 2H), 7.48 (t, J=7.4 Hz, 1H), 7.40 (t, J=7.5 Hz, 2H), 7.26-7.18 (m, 2H), 7.08 (dd, J=7.5, 1.8 Hz, 1H), 6.44 (d, J=8.6 Hz, 1H), 5.49 (d, J=8.8 Hz, 1H), 5.07 (dd, J=14.5, 11.9 Hz, 1H), 4.63-4.43 (m, 1H), 4.35-4.23 (m, 1H), 3.76-3.58 (m, 1H), 1.50 (s, 9H).

Intermediate A-1: (S)-9-Amino-6,6-difluoro-11-phenyl-6,7-dihydro-5H-4-oxa-7a,10-diazabenzo[ef]heptalen-8(9H)-one

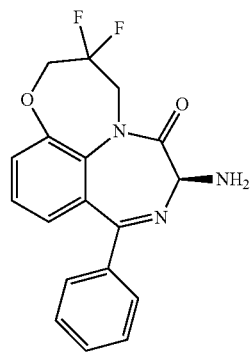

(A-1)

To a solution of Intermediate A-1H (0.87 g, 1.96 mmol) in CH$_2$Cl$_2$ (6 mL) was added 4N HCl/dioxane (2.94 mL, 11.77 mmol). The reaction mixture was initially clear and then formed a suspension. After 5 h, HPLC showed the product formed and no starting material was detected. The mixture was concentrated and dried under vacuum for 16 h to afford (S)-9-amino-6,6-difluoro-11-phenyl-6,7-dihydro-5H-4-oxa-7a,10-diazabenzo[ef]heptalen-8(9H)-one, Intermediate A-1 (745 mg, 1.962 mmol, 100% yield) as an off-white solid as HCl salt. HPLC: RT=2.115 min (H₂O/MeOH with H₃PO₄, YMC S5 ODS, 4.6×50 mm, gradient=4 min, flow rate=4 mL/min., wavelength=220 nm); MS(ES):m/z=344.3 [M+H]⁺.

Intermediate B-1: (S)-9-Amino-7-phenyl-1,2-dihydro-3-oxa-8,10a-diazacyclohepta[de]naphthalen-10(9H)-one

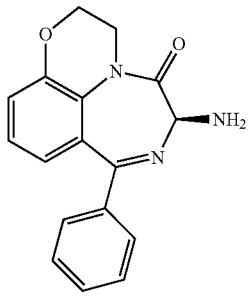

(B-1)

Intermediate B-1A: tert-Butyl(10-oxo-7-phenyl-1,2,9,10-tetrahydro-3-oxa-8,10a-diazacyclohepta[de]naphthalen-9-yl)carbamate

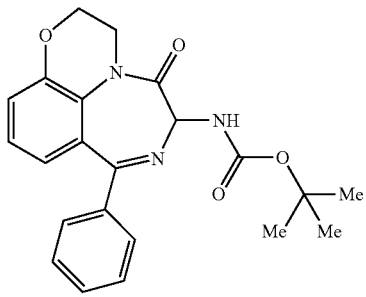

(B-1A)

To a solution of Intermediate A-1E (200 mg, 0.544 mmol) in DMF (10 mL) was added cesium carbonate (390 mg, 1.198 mmol), followed by ethylene dibromide (0.141 mL, 1.633 mmol). The reaction mixture was stirred at room temperature for 24 h and then filtered to remove solids. The filtrate was diluted with EtOAc and water, and the organic phase was separated. The organic phase was washed with water, brine, dried over anhydrous MgSO₄, filtered and concentrated. MeOH was added and the precipitate was collected by filtration to afford 110 mg of Intermediate 1C as a white solid. The filtrate was purified by flash chromatography (Teledyne ISCO CombiFlash Rf, 0-50% solvent EtOAc in hexanes, REDISEP® SiO₂ 12 g). The desired product was eluted with about 25% EtOAc/hexane to afford 80 mg of product as white solid. The solids were combined to afford tert-butyl(10-oxo-7-phenyl-1,2,9,10-tetrahydro-3-oxa-8,10a-diazacyclohepta[de]naphthalen-9-yl)carbamate, Intermediate B-1A (190 mg, 0.478 mmol, 88%) as a white solid. ¹H NMR (400 MHz, chloroform-d) δ 7.62-7.55 (m, 2H), 7.49-7.36 (m, 3H), 7.11 (d, J=4.2 Hz, 2H), 6.98-6.85 (m, 1H), 6.40 (d, J=8.6 Hz, 1H), 5.47 (d, J=8.8 Hz, 1H), 5.00-4.89 (m, 1H), 4.58-4.49 (m, 1H), 4.26 (td, J=11.2, 2.9 Hz, 1H), 3.18 (ddd, J=13.6, 11.1, 2.9 Hz, 1H), 1.50 (s, 9H).

Intermediate B-1: (S)-9-Amino-7-phenyl-1,2-dihydro-3-oxa-8,10a-diazacyclohepta[de]naphthalen-10(9H)-one

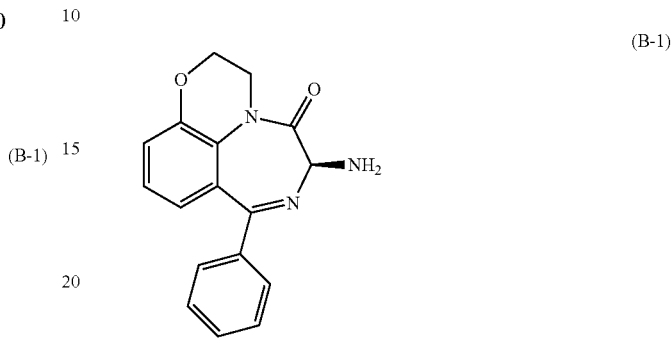

(B-1)

To a solution of Intermediate B-1A (190 mg, 0.478 mmol) in CH₂Cl₂ (8 mL) at room temperature was slowly added TFA (2 mL, 26.0 mmol). The reaction mixture was stirred at room temperature for 2 h. The liquids were removed under reduced pressure and the resulting residue was diluted with EtOAc and saturated aqueous NaHCO₃. The layers were separated and the pH of the aqueous layer was adjusted to 7. The aqueous layer was extracted with EtOAc (2×) and the organic layers were combined and dried over anhydrous MgSO₄, filtered and concentrated. The concentrate was purified by flash chromatography (Teledyne ISCO CombiFlash Rf, 0-10% MeOH in CH₂Cl₂, REDISEP® SiO₂ 12 g) to afford (0.072 g, 0.245 mmol, 45%) of racemic material as a white solid. This material was resolved by chiral SFC (Instrument: Berger SFC MGII, Column: Chiral Lux 25×3 cm, 5 μm; column temp: 40° C.; Mobile Phase: CO₂/MeOH (75/25); Flow rate: 85 mL/min; Detection at 220 nm.) to afford (S)-9-amino-7-phenyl-1,2-dihydro-3-oxa-8,10a-diazacyclohepta[de]naphthalen-10(9H)-one, Intermediate B-1 (0.024 g, 0.082 mmol, 34%). ¹H NMR (400 MHz, chloroform-d) δ 7.68-7.58 (m, 2H), 7.52-7.38 (m, 3H), 7.19-7.07 (m, 2H), 6.95 (dd, J=6.2, 2.9 Hz, 1H), 5.08-4.92 (m, 1H), 4.68 (s, 1H), 4.60-4.51 (m, 1H), 4.26 (td, J=11.2, 3.0 Hz, 1H), 3.26-3.14 (m, 1H), 2.55 (br. s., 2H).

Intermediate C-1: 9-Amino-7-(m-tolyl)-1,2-dihydro-3-oxa-8,10a-diazacyclohepta[de]naphthalen-10(9H)-one

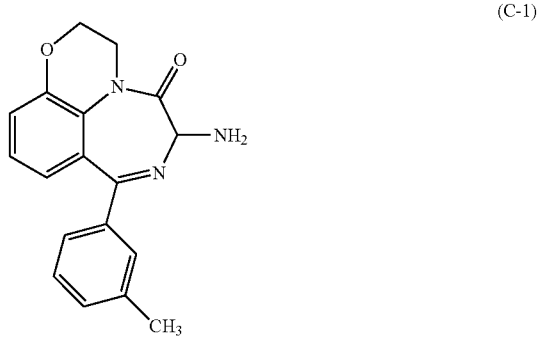 [SMILES: Cc1cccc(C2=NC(N)C(=O)N3CCOc4cccc2c43)c1]

(C-1)

Intermediate C-1A: (3,4-Dihydro-2H-benzo[b][1,4]oxazin-5-yl)(m-tolyl)methanone

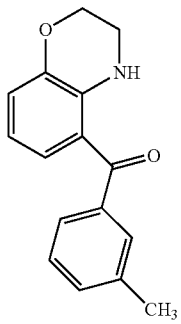

(C-1A)

A dried 200 mL round bottom was charged with boron trichloride (1.0 M PhMe) (4.67 mL, 4.67 mmol) and cooled to 0° C. for 15 min. Next, 3,4-dihydro-2H-benzo[b][1,4]oxazine (574 mg, 4.25 mmol) in toluene (Volume: 9.4 mL) was added dropwise over about 5 min, and then the solution was stirred for 10 minutes. Aluminum chloride (623 mg, 4.67 mmol) was added and the solution was stirred for 5 minutes. Then, 3-methylbenzonitrile (0.605 mL, 5.10 mmol) was added. The reaction mixture was stirred at 0° C., for about 1 h, then allowed to warm to room temperature and heated to reflux for 8 h. HCl (1.5 M) (28.3 mL, 42.5 mmol) was added, and the reaction mixture was heated to reflux for 2 h. The reaction mixture was cooled to room temperature, basified to pH 9 with 1 M NaOH, and extracted three times with $CH_2Cl_2$. The organic layers were dried with $MgSO_4$ and evaporated. The residue was purified via ISCO (40 g column; hex/EtOAc; 2 min, 0%, 27 min, 40%, 30 min 40%;) to afford (3,4-dihydro-2H-benzo[b][1,4]oxazin-5-yl)(m-tolyl)methanone, Intermediate C-1A (0.73 g, 2.9 mmol, 68%) $^1$H NMR (400 MHz, chloroform-d) δ 8.31 (br. s., 1H), 7.47-7.39 (m, 2H), 7.37-7.33 (m, 2H), 7.12 (dd, J=8.1, 1.5 Hz, 1H), 6.99-6.88 (m, 1H), 6.48 (t, J=7.9 Hz, 1H), 4.29 (t, J=4.5 Hz, 2H), 3.63 (td, J=4.6, 2.8 Hz, 2H), 2.43 (s, 3H).

Intermediate C-1B: 7-(m-Tolyl)-1,2-dihydro-3-oxa-8,10a-diazacyclohepta[de]naphthalen-10(9H)-one

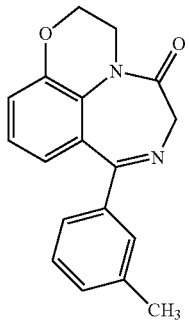

(C-1B)

(3,4-Dihydro-2H-benzo[b][1,4]oxazin-5-yl)(m-tolyl)methanone (0.514 g, 2.029 mmol) was dissolved in DCM (Volume: 20.29 ml) and cooled to 0° C. Pyridine (0.410 ml, 5.07 mmol) was added, followed by the addition of bromoacetyl bromide (0.353 ml, 4.06 mmol). After 1 h, more pyridine (0.410 ml, 5.07 mmol) and bromoacetyl bromide (0.353 ml, 4.06 mmol) were added. The reaction mixture was stirred at room temperature for 2.5 h. Then ammonia (2 M in MeOH) (22.32 ml, 44.6 mmol) was added. The reaction mixture was stirred at room temperature for 1.5 h. Acetic acid (44 ml, 769 mmol) was added and stirred at room temperature for 20 min. The reaction mixture was evaporated. The black oil was azeotroped twice with DCM and one with PhMe. The DCM soluble portion of the crude tar was purified via ISCO (40 g column; hex/EtOAc; 0 min, 5%, 2 min, 5%; 26 min, 40%, 33 min, 40%;). Some mixed fractions were repurified using the same method to afford 7-(m-tolyl)-1,2-dihydro-3-oxa-8,10a-diazacyclohepta[de]naphthalen-10(9H)-one, Intermediate C-1B (0.27 g, 0.93 mmol, 46% $^1$H NMR (400 MHz, chloroform-d) δ 7.49-7.43 (m, 1H), 7.35-7.25 (m, 3H), 7.13-7.03 (m, 2H), 6.92 (dd, J=6.2, 3.1 Hz, 1H), 5.00-4.84 (m, 2H), 4.52 (d, J=9.7 Hz, 1H), 4.20 (br. s., 1H), 3.96 (d, J=10.8 Hz, 1H), 3.12 (br. s., 1H), 2.39 (s, 3H).

Intermediate C-1C: 9-Azido-7-(m-tolyl)-1,2-dihydro-3-oxa-8,10a-diazacyclohepta[de]naphthalen-10(9H)-one

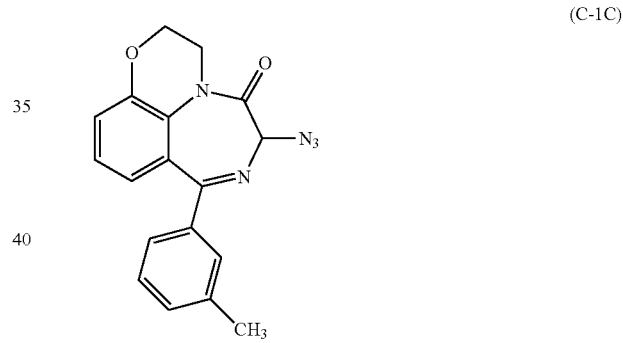

(C-1C)

To a solution of 7-(m-tolyl)-1,2-dihydro-3-oxa-8,10a-diazacyclohepta[de]naphthalen-10(9H)-one, Intermediate C-1B (0.27 g, 0.93 mmol) in THF (Ratio: 1.000, Volume: 4.65 ml) at −78° C. was added KHMDS (1.0 M in THF) (1.396 ml, 1.396 mmol) over about 5 min. The reaction mixture was stirred at −78° C. for 40 min. Next, 2,4,6-triisopropylbenzenesulfonyl azide (0.720 g, 2.326 mmol) in THF (Ratio: 1.000, Volume: 4.65 ml) was added dropwise over about 5 minutes. The resulting mixture was stirred at −78° C. for 1 h. Acetic acid (0.799 ml, 13.96 mmol) was added and the reaction mixture warmed to room temperature and stirred at room temperature for 16 h. The reaction mixture was quenched with saturated $NaHCO_3$ and extracted three times with DCM. EtOH was used to break the emulsion. The organic layers were washed with $H_2O$, dried with $MgSO_4$ and evaporated. The residue was purified via ISCO (24 g column; DCM/10% MeOH in DCM; 1 min, 0%, 15 min, 20%. 18 min, 20%) to afford 9-azido-7-(m-tolyl)-1,2-dihydro-3-oxa-8,10a-diazacyclohepta[de]naphthalen-10(9H)-one, Intermediate C-1C (0.27 g, 0.82 mmol, 35%) $^1$H NMR (400 MHz, chloroform-d) δ 7.52 (s, 1H), 7.45-7.37 (m, 1H), 7.35-7.24 (m, 2H), 7.19-7.09 (m, 2H), 6.98 (dd, J=4.8, 4.2 Hz, 1H), 5.01-4.91 (m, 1H), 4.77 (s, 1H), 4.60-4.49 (m, 1H), 4.26 (td, J=11.2, 3.0 Hz, 1H), 3.19 (ddd, J=13.6, 11.1, 3.1 Hz, 1H), 2.45-2.38 (s, 3H).

Intermediate C-1: 9-Amino-7-(m-tolyl)-1,2-dihydro-3-oxa-8,10a-diazacyclohepta[de]naphthalen-10(9H)-one

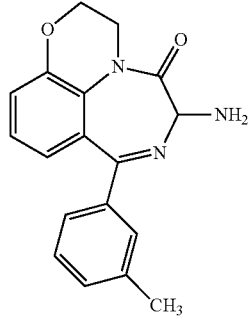

(C-1)

To a solution of 9-azido-7-(m-tolyl)-1,2-dihydro-3-oxa-8,10a-diazacyclohepta[de]naphthalen-10(9H)-one, Intermediate C-1C (0.065 g, 0.195 mmol) in THF (Volume: 0.975 ml) at room temperature was added triphenylphosphine (0.153 g, 0.585 mmol) and H$_2$O (0.035 ml, 1.950 mmol). The reaction mixture was stirred for 16 h. The mixture was evaporated and the residue was purified via ISCO (12 g column; DCM/10% MeOH in DCM; 1 min, 0%; 17 min, 100%, 19 min 100%) to afford 9-amino-7-(m-tolyl)-1,2-dihydro-3-oxa-8,10a-diazacyclohepta[de]naphthalen-10(9H)-one, Intermediate C-1 (0.031 g, 0.10 mmol, 52%). $^1$H NMR (400 MHz, chloroform-d) δ 7.48 (s, 1H), 7.33-7.22 (m, 3H), 7.13-7.05 (m, 2H), 6.91 (dd, J=6.5, 2.8 Hz, 1H), 5.00-4.84 (m, 1H), 4.63 (s, 1H), 4.56-4.45 (m, 1H), 4.21 (td, J=11.2, 3.0 Hz, 1H), 3.16 (ddd, J=13.7, 11.1, 3.0 Hz, 1H), 2.49 (br. s., 2H), 2.37 (s, 3H).

Intermediate D-1: 9-Amino-7-(3-chlorophenyl)-1,2-dihydro-3-oxa-8,10a-diazacyclohepta[de]naphthalen-10(9H)-one

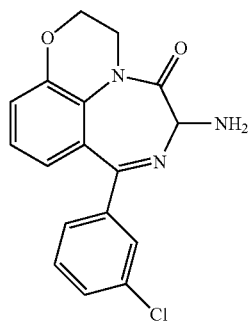

(D-1)

Intermediate D-1 was prepared from 3-chlorobenzonitrile and 3,4-dihydro-2H-benzo[b][1,4]oxazine according to the procedure shown for Intermediate C-1. NMR: $^1$H NMR (400 MHz, DMSO-d$_6$) δ ppm 7.56 (2H, m), 7.45 (2H, m), 7.20 (2H, m), 6.85 (1H, m), 4.75 (1H, d, J=4.8 Hz), 4.5 (2H, m), 4.20 (1H, m), 3.20 (1H, m), 2.70 (2H, bs).

Intermediate E-1: (S)-6-Amino-8-phenyl-2,3-dihydro-1H-[1,4]diazepino[1,7,6-de]quinoxalin-5(6H)-one

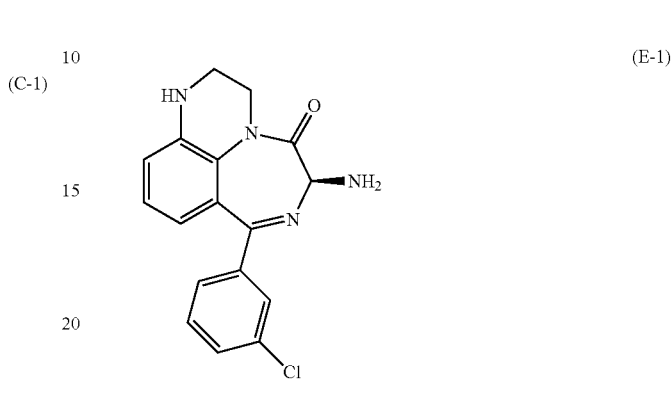

(E-1)

Intermediate E-1A: 3,4-Dihydroquinoxalin-2(1H)-one

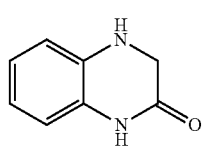

(E-1A)

To a solution of benzene-1,2-diamine (150 g, 1387 mmol) and triethylamine (193 mL, 1387 mmol) in DMF (Ratio: 20 times, Volume: 3000 mL) was added ethyl bromoacetate (232 g, 1387 mmol). The reaction mixture was heated at 120° C. for 36 h. The reaction mixture was cooled to room temperature and diluted with EtOAc and water. The organic layer was separated and washed with brine, dried over Na$_2$SO$_4$, filtered, and concentrated to give crude material. The crude product was purified via ISCO, eluted with 50% EtOAC/hexane to afford 3,4-dihydroquinoxalin-2(1H)-one, Intermediate E-1A (140 g, 945 mmol, 68.1%). $^1$H NMR (400 MHz, CDCl$_3$) δ ppm 7.7 (1H, bs), 6.9 (1H, m), 6.75 (1H, m), 6.70 (2H, m), 4.0 (1H, s), 3.85 (1H, bs).

Intermediate E-1B: 1,2,3,4-Tetrahydroquinoxaline

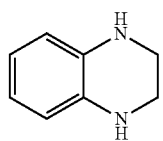

(E-1B)

To a solution of lithium aluminum hydride (28.2 g, 742 mmol) in THF (1500 mL) at 0° C. was added 3,4-dihydroquinoxalin-2(1H)-one (50 g, 337 mmol) portion wise. The reaction mixture was warmed up to room temperature and heated at 80° C. for 4 h. The reaction mixture was cooled to 0°

C. and quenched with water (20 mL) dropwise. The insoluble inorganics was filtered through CELITE®. The filtrate was dried over Na₂SO₄, filtered, concentrated to afford 1,2,3,4-tetrahydroquinoxaline (36 g, 268 mmol, 80% yield). NMR: ¹H NMR (400 MHz, CDCl₃) δ ppm 6.6 (2H, m), 6.5 (2H, m), 3.65 (2H, bs), 3.40 (4H, s).

Intermediate E-1C: (3-Chlorophenyl)(1,2,3,4-tetrahydroquinoxalin-5-yl)methanone

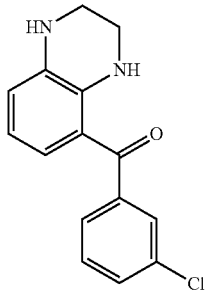
(E-1C)

To a solution of 1,2,3,4-tetrahydroquinoxaline (50 g, 373 mmol) in toluene (Ratio: 20 times, Volume: 20 mL) at 0° C. was added BCl₃ (1M solution in DCM, 9.0 mL, 447 mmol). Then aluminum chloride (59.6 g, 447 mmol) and 3-chlorobenzonitrile (61.5 g, 447 mmol) were added. The reaction mixture was warmed up to room temperature and heated at 110° C. for 8 h. The reaction mixture was cooled to room temperature. HCl (15.0 mL, 1.5 N) was added and the mixture was heated at 110° C. for 3 h. The reaction mixture was cooled to room temperature and basified with 10% NaHCO₃. The aqueous layer was extracted with EtOAc. The combined organic layers were washed with brine, dried over Na₂SO₄, filtered, concentrated to give a crude material. This crude material was purified via BIOTAGE®, eluted with 20% EtOAC/hexane to afford (3-chlorophenyl)(1,2,3,4-tetrahydroquinoxalin-5-yl)methanone, Intermediate E-1C (50 g, 183 mmol, 49.2% yield)¹H NMR (400 MHz, CDCl₃) δ ppm 8.6 (1H, bs), 7.6 (1H, s), 7.5 (2H, m), 7.4 (1H, m), 6.8 (1H, m), 6.6 (1H, m), 6.4 (1H, m), 3.8 (1H, bs), 3.6 (2H, m), 3.4 (2H, m).

Intermediate E-1D: Benzyl 5-(3-chlorobenzoyl)-3,4-dihydroquinoxaline-1(2H)-carboxylate

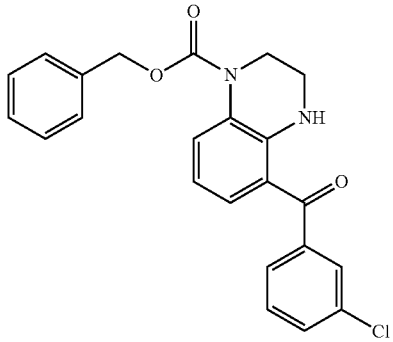
(E-1D)

To a solution of (3-chlorophenyl)(1,2,3,4-tetrahydroquinoxalin-5-yl)methanone (50 g, 183 mmol) in DCM (200 mL) at 0° C. was added pyridine (17.79 mL, 220 mmol). Then CBZ—Cl (26.2 mL, 183 mmol) in DCM (1.0 mL) was added dropwise. The reaction mixture was warmed up to room temperature and stirred at room temperature for 3 h. The reaction mixture was washed with H₂O, saturated NaHCO₃, and brine, dried over Na₂SO₄, filtered, concentrated to give crude material. This crude material was purified via BIOTAGE®, eluted with 10% EtOAC/hexane to afford benzyl 5-(3-chlorobenzoyl)-3,4-dihydroquinoxaline-1(2H)-carboxylate, Intermediate E-1D (60 g, 147 mmol, 80% yield). ¹H NMR (400 MHz, CDCl₃) δ ppm 8.5 (1H, bs), 7.6 (1H, s), 7.45 (2H, m), 7.4 (7H, m), 7.25 (1H, m), 6.5 (1H, m), 5.2 (2H, m), 3.9 (2H, m), 3.6 (2H, m).

Intermediate E-1E: Benzyl 5-(3-chlorobenzoyl)-3,4-dihydroquinoxaline-1(2H)-carboxylate

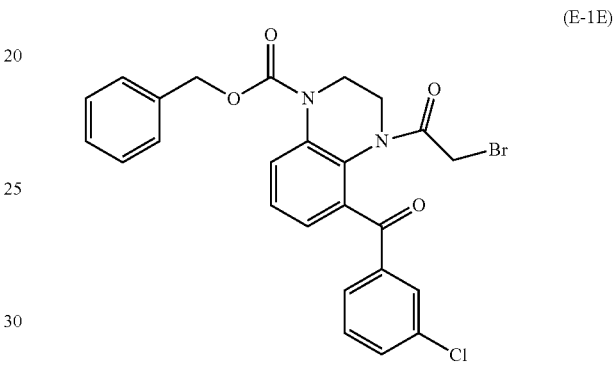
(E-1E)

To a solution of benzyl 5-(3-chlorobenzoyl)-3,4-dihydroquinoxaline-1(2H)-carboxylate, Intermediate E-1D (50 g, 123 mmol) in DCM (500 mL) at 0° C. was added pyridine (14.91 ml, 184 mmol). Bromoacetyl bromide (26.7 ml, 307 mmol) in DCM (1.0 mL) was added dropwise. The reaction mixture was stirred at 0° C. for 3 h. The reaction mixture was washed with H₂O, saturated NaHCO₃, and brine, dried over Na₂SO₄, filtered, concentrated to afford benzyl 4-(2-bromoacetyl)-5-(3-chlorobenzoyl)-3,4-dihydroquinoxaline-1 (2H)-carboxylate, Intermediate E-1E (55 g, 104 mmol, 85% yield). ¹H NMR (400 MHz, CDCl₃) δ ppm 8.0 (1H, bs), 7.85 (1H, s), 7.75 (1H, m), 7.6 (2H, m) 7.4 (7H, m), 7.10 (1H, m), 5.3 (2H, s), 4.15 (2H, m), 4.0 (2H, m), 3.8 (2H, m).

Intermediate E-1F: Benzyl 8-(3-chlorophenyl)-5-oxo-2,3,5,6-tetrahydro-1H-[1,4]diazepino[1,7,6-de]quinoxaline-1-carboxylate

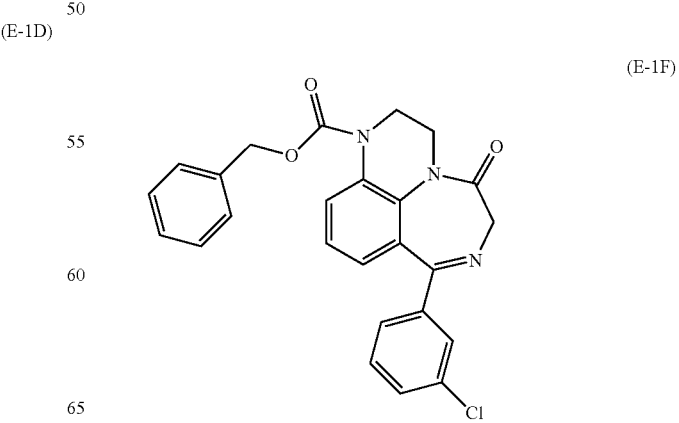
(E-1F)

To benzyl 4-(2-bromoacetyl)-5-(3-chlorobenzoyl)-3,4-dihydroquinoxaline-1(2H)-carboxylate, Intermediate E-1E (14 g, 26.5 mmol) in a 250 round bottle flask was added in 2M methanolic ammonia (70 ml, 26.5 mmol). The mixture was stirred at room temperature for 16 h. The reaction mixture concentrated and purified via BIOTAGE®, eluted with 20% EtOAC/hexane to afford benzyl 8-(3-chlorophenyl)-5-oxo-2,3,5,6-tetrahydro-1H-[1,4]diazepino[1,7,6-de]quinoxaline-1-carboxylate, Intermediate E-1F (8 g, 17.94 mmol, 67% yield). $^1$H NMR (400 MHz, CDCl$_3$) δ ppm 8.1 (1H, bs), 7.6 (1H, s), 7.5-7.3 (9H, m), 7.2 (1H, m) 7.05 (1H, m), 5.3 (2H, m), 4.9 (1H, m), 4.6 (1H, m), 4.25 (1H, m), 3.9 (1H, m), 3.8 (1H, m), 3.35 (1H, m).

Intermediate E-1G: Benzyl 6-azido-8-(3-chlorophenyl)-5-oxo-2,3,5,6-tetrahydro-1H-[1,4]diazepino[1,7,6-de]quinoxaline-1-carboxylate

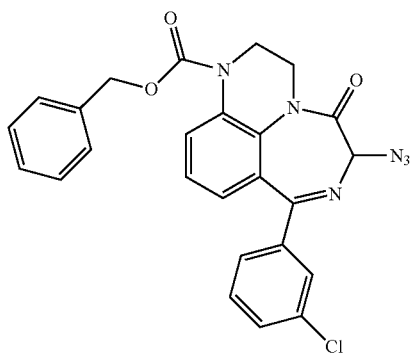

(E-1G)

To a solution of benzyl 8-(3-chlorophenyl)-5-oxo-2,3,5,6-tetrahydro-1H-[1,4]diazepino[1,7,6-de]quinoxaline-1-carboxylate, Intermediate E-1F (7.0 g, 15.7 mmol) in tetrahydrofuran (10 mL) at −78° C. was added potassium hexamethyldisilazide (18.84 mL, 18.84 mmol, 1M in THF). The reaction mixture was stirred at −78° C. for 1 h. Then 2,4,6-triisopropylbenzenesulfonyl azide (5.83 g, 18.84 mmol) in THF (1.0 mL) was added. The reaction mixture was stirred at −78° C. for 1 h. Acetic acid (21 mL, 367 mmol) was added and the reaction mixture was allowed to warm to room temperature and stirred at room temperature for 16 h. The reaction was quenched with 10% NaHCO$_3$ solution. The aqueous layer was extracted with ethyl acetate (3×50 ml). The combined organic layers were washed with brine, dried over Na$_2$SO$_4$, filtered, concentrated to give crude material. The crude material was purified via BIOTAGE®, eluted with 20% EtOAC/hexane to afford benzyl 6-azido-8-(3-chlorophenyl)-5-oxo-2,3,5,6-tetrahydro-1H-[1,4]diazepino[1,7,6-de]quinoxaline-1-carboxylate, Intermediate E-1G (4.2 g, 8.63 mmol, 54.9% yield). $^1$H NMR (400 MHz, CDCl$_3$) δ ppm 8.1 (1H, s), 7.6 (1H, s), 7.55 (1H, m), 7.45 (1H, m), 7.35 (7H, m), 7.25 (1H, m), 7.15 (1H, m), 5.3 (2H, m), 4.65 (2H, m), 4.3 (1H, m), 3.8 (1H, m), 3.4 (1H, m).

Intermediate E-1: 6-Amino-8-(3-chlorophenyl)-2,3-dihydro-1H-[1,4]diazepino[1,7,6-de]quinoxalin-5(6H)-one

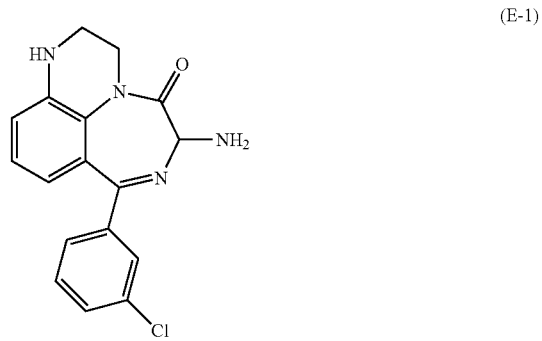 [SMILES: NC1N=C(c2cccc(Cl)c2)c2cccc3c2N(CCN3)C1=O]

(E-1)

To a solution of benzyl 6-azido-8-(3-chlorophenyl)-5-oxo-2,3,5,6-tetrahydro-1H-[1,4]diazepino[1,7,6-de]quinoxaline-1-carboxylate, Intermediate E-1G (4.2 g, 8.63 mmol) in ethyl acetate (150 mL) at room temperature was added 10% palladium hydroxide on carbon (1.2 g, 8.54 mmol). The reaction mixture was stirred under H$_2$ balloon for 4 h. The reaction mixture was filtered through CELITE®. The filtrate was concentrated to afford Intermediate E-1 (0.9 g, 2.75 mmol, 31.9% yield). $^1$H NMR (400 MHz, DMSO-d$_6$) δ 7.60-7.49 (m, 2H), 7.48-7.34 (m, 2H), 6.98 (t, J=7.9 Hz, 1H), 6.82 (dd, J=8.0, 1.2 Hz, 1H), 6.66 (d, J=4.4 Hz, 1H), 6.40 (dd, J=7.7, 1.3 Hz, 1H), 4.68 (dd, J=12.5, 3.3 Hz, 1H), 4.41 (s, 1H), 3.57-3.45 (m, 1H), 3.20 (td, J=11.8, 4.0 Hz, 1H), 2.82 (td, J=12.0, 3.3 Hz, 1H), 2.63 (br. s., 2H).

Intermediate F-1: 9-Amino-7-(m-tolyl)-1,2-dihydro-3-oxa-8,10a-diazacyclohepta[de]naphthalen-10(9H)-one

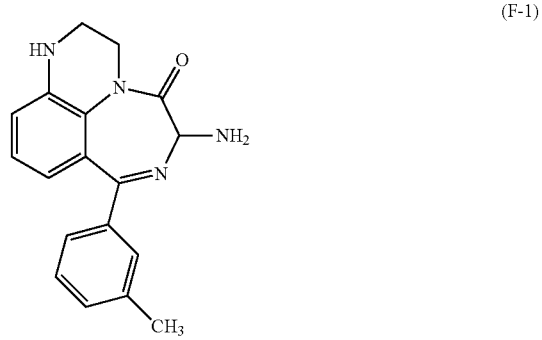 [SMILES: Cc1cccc(C2=NC(N)C(=O)N3CCNc4cccc2c43)c1]

(F-1)

Intermediate F-1 was prepared from 3-chlorobenzonitrile and Intermediate E-1B according to the procedure shown for Intermediate E-1. $^1$H NMR (400 MHz, DMSO-d$_6$) δ 7.36 (s, 1H), 7.32-7.20 (m, 3H), 6.96 (t, J=7.8 Hz, 1H), 6.80 (dd, J=8.1, 1.3 Hz, 1H), 6.64 (d, J=4.4 Hz, 1H), 6.38 (dd, J=7.7, 1.3 Hz, 1H), 4.69 (dd, J=12.4, 3.4 Hz, 1H), 4.44 (s, 1H), 3.57-3.44 (m, 1H), 3.20 (td, J=11.7, 3.9 Hz, 1H), 2.81 (td, J=12.0, 3.3 Hz, 1H), 2.31 (s, 3H).

Intermediate G-1: (S)-6-Amino-8-phenyl-2,3-dihydro-1H-[1,4]diazepino[1,7,6-de]quinoxalin-5(6H)-one

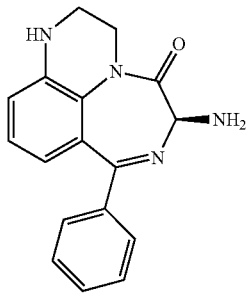

(G-1)

Intermediate G-1 was prepared from benzonitrile and Intermediate E-1B according to the procedure shown for Intermediate E-1. The racemate material (4.5 g) was resolved by chiral SFC (Instrument: Berger SFC MGII, Column: AS-H 25×5 cm, 5 μm; column temp: 40° C.; Mobile Phase: CO₂/MeOH with 0.1% DEA (70/30); Flow rate: 85 mL/min; Detection at 220 nm.) to afford Intermediate G-1 (1.98 g, 44%).

Intermediate H-1: 9-Amino-11-phenyl-6,7-dihydro-5H-4-oxa-7a,10-diazabenzo[ef]heptalen-8(9H)-one

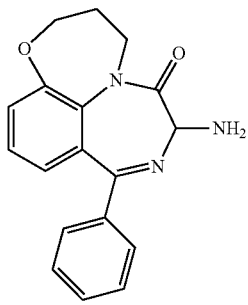

(H-1)

Intermediate H-1A: tert-Butyl(8-oxo-11-phenyl-6,7,8,9-tetrahydro-5H-4-oxa-7a,10-diazabenzo[ef]heptalen-9-yl)carbamate

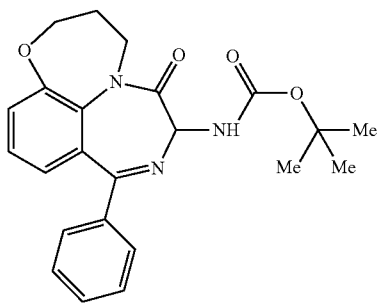

(H-1A)

To a solution of tert-butyl 9-hydroxy-2-oxo-5-phenyl-2,3-dihydro-1H-benzo[e][1,4]diazepin-3-ylcarbamate, Intermediate A-1E (0.5 g, 1.36 mmol) in DMF (10 mL) at room temperature was added cesium carbonate (887 mg, 2.72 mmol), followed by 1,3-dibromopropane (0.417 mL, 4.08 mmol). The reaction mixture was stirred at room temperature for 3 h, and then filtered to remove the solid material. The filtrate was diluted with EtOAc and water. The organic layer was separated and washed with water (2×), brine, dried over MgSO₄, filtered and concentrated to give crude material. This crude material was triturated with MeOH and the solid material was collected by filtration to afford Intermediate F-1A (0.36 g, 0.88 mmol, 64%). ¹H NMR (400 MHz, chloroform-d) δ 7.69-7.63 (m, 2H), 7.49 (t, J=7.3 Hz, 1H), 7.41 (t, J=7.5 Hz, 2H), 7.20-7.12 (m, 2H), 7.06-6.89 (m, 1H), 6.48 (d, J=8.6 Hz, 1H), 5.46 (d, J=8.8 Hz, 1H), 4.55 (dd, J=13.6, 4.2 Hz, 1H), 4.41-4.20 (m, 2H), 3.45 (td, J=12.4, 4.8 Hz, 1H), 2.42-2.27 (m, 1H), 2.21 (d, J=9.7 Hz, 1H), 1.52 (s, 9H).

Intermediate H-1: 9-Amino-11-phenyl-6,7-dihydro-5H-4-oxa-7a,10-diazabenzo[ef]heptalen-8(9H)-one

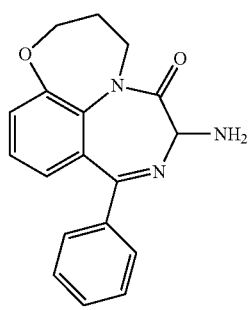

(H-1)

To tert-butyl(8-oxo-11-phenyl-6,7,8,9-tetrahydro-5H-4-oxa-7a,10-diazabenzo[ef]heptalen-9-yl)carbamate, Intermediate F-1A (0.36 g, 0.88 mmol) was slowly added 4N HCl/dioxane (6 mL). The mixture became a yellow solution. The reaction mixture was stirred at room temperature for 3 h. Solvent was removed using a Rotovap to afford 9-amino-11-phenyl-6,7-dihydro-5H-4-oxa-7a,10-diazabenzo[ef]heptalen-8(9H)-one, HCl salt (0.3 g, 0.82 mmol, 60.3% yield) as an off-white solid. ¹H NMR (400 MHz, chloroform-d) δ 7.71-7.62 (m, 2H), 7.52-7.36 (m, 3H), 7.22-7.10 (m, 2H), 7.00 (dd, J=7.3, 2.0 Hz, 1H), 4.66 (s, 1H), 4.64-4.51 (m, 1H), 4.41-4.18 (m, 2H), 3.41 (ddd, J=13.6, 11.7, 4.8 Hz, 1H), 2.45 (br. s., 2H), 2.41-2.28 (m, 1H), 2.26-2.12 (m, 1H).

Example 1

(2R,3R)—N-((7S)-3,3-Difluoro-6-oxo-9-phenyl-3,4,6,7-tetrahydro-2H-[1,4]diazepino[1,7,6-ef][1,5]benzoxazepin-7-yl)-3-(3-methyl-4-isoxazolyl)-2-(3,3,3-trifluoropropyl)succinamide

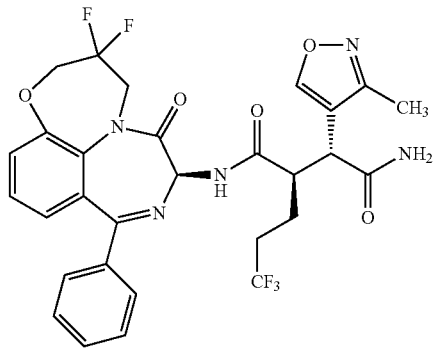 [SMILES: Cc1nocc1[C@H](C(N)=O)[C@@H](CCC(F)(F)F)C(=O)N[C@H]1N=C(c2ccccc2)c2cccc3c2N(CC(F)(F)CO3)C1=O]

Preparation 1A

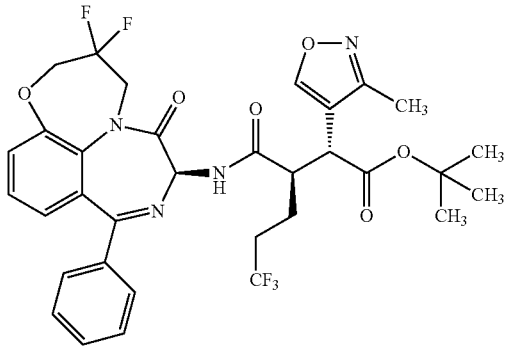

In a 100 mL round-bottomed flask, a solution of Intermediate A-1 (0.475 g, 1.25 mmol), Et₃N (0.44 mL, 3.13 mmol), Intermediate S-6 (0.527 g, 1.50 mmol) in DMF (10 mL) was treated with o-benzotriazol-1-yl-N,N,N',N'-tetramethyluronium tetrafluoroborate (0.602 g, 1.876 mmol). The reaction mixture was stirred at room temperature for 1 hour. The reaction mixture was diluted with water and saturated aqueous NaHCO₃. An off-white precipitate formed and was filtered and then washed with water. The resulting solid was dried on the filter under a stream of nitrogen. Then the solid was dissolved in CH₂Cl₂ (1.5 mL) and purified with ISCO 120 g column, 85 mL/min 0-50% EtOAc/hexane. The product was eluted with 40% EtOAc/hexane. After concentration, Preparation 1A (0.73 g, 1.08 mmol, 78%) was obtained as a white solid. MS(ES):m/z=677.3[M+H⁺]; HPLC: RT=3.773 min Purity=99%. (H₂O/MeOH with TFA, CHROMOLITH® ODS S5 4.6×50 mm, gradient=4 min, wavelength=220 nm). ¹H NMR (400 MHz, chloroform-d) δ 8.53 (s, 1H), 7.55-7.47 (m, 3H), 7.47-7.38 (m, 2H), 7.32-7.20 (m, 2H), 7.10 (dd, J=7.5, 1.8 Hz, 1H), 5.49 (d, J=7.9 Hz, 1H), 5.02 (dd, J=14.7, 11.4 Hz, 1H), 4.61-4.46 (m, 1H), 4.38-4.21 (m, 1H), 3.71-3.46 (m, 2H), 3.04 (td, J=10.2, 3.6 Hz, 1H), 2.37-2.26 (m, 5H), 2.07-1.97 (m, 1H), 1.91 (dd, J=6.5, 3.4 Hz, 1H), 1.47 (s, 9H).

Preparation 1B: (2R,3R)-3-(((S)-6,6-Difluoro-8-oxo-11-phenyl-6,7,8,9-tetrahydro-5H-4-oxa-7a,10-diazabenzo[ef]heptalen-9-yl)carbamoyl)-6,6,6-trifluoro-2-(3-methylisoxazol-4-yl)hexanoic acid

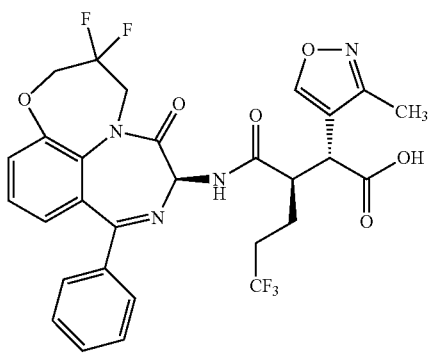

To a solution of Preparation 1A (0.730 g, 1.08 mmol) in CH₂Cl₂ (8 mL) at room temperature was added TFA (8 mL) slowly. The color of the solution turned to yellow. The reaction mixture was stirred at room temperature for 5 h. Solvent was removed using a Rotovap. The residue was then dissolved in CH₃CN and water. The mixture was freeze dried under vacuum for 16 h to afford Preparation 1B as an off-white solid. HPLC: RT=3.29 min (H₂O/MeOH with TFA, CHROMOLITH® ODS S5 4.6×50 mm, gradient=4 min, wavelength=220 nm). MS(ES): m/z=621.3 (M+H)'. ¹H NMR (400 MHz, chloroform-d) δ 8.55 (s, 1H), 8.05 (d, J=7.9 Hz, 1H), 7.57-7.37 (m, 5H), 7.34-7.17 (m, 2H), 7.06 (dd, J=7.6, 1.7 Hz, 1H), 5.54 (d, J=7.7 Hz, 1H), 5.02 (dd, J=14.5, 11.4 Hz, 1H), 4.61-4.43 (m, 1H), 4.32 (dd, J=10.3, 4.6 Hz, 1H), 3.97 (d, J=7.3 Hz, 1H), 3.72 (d, J=9.9 Hz, 2H), 3.24-3.08 (m, 1H), 2.41-2.26 (m, 5H), 2.10-1.91 (m, 2H).

Example 1

To the solution of Preparation 1B in THF (4 mL) was added 1-hydroxybenzotriazole hydrate (0.383 g, 2.50 mmol). The mixture was stirred for 20 min. A homogeneous solution was observed. Then EDC (480 mg, 2.501 mmol) was added. The mixture was stirred at room temperature for 15 min. A slurry was observed. The mixture was cooled to 8° C. with an ice water bath. Next, 2N NH₃ in IPA (3.75 mL, 7.50 mmol) was added and the reaction mixture was stirred at 0° C. for 20 min, and then stirred at room temperature. HPLC showed 90% conversion to the product. The mixture was stirred at room temperature for 16 h. Water was added slowly and the mixture became a homogeneous solution, followed by the formation of precipitate. The solid material was collected by filtration and rinsed with water for 3 times and dried under vacuum for 3 h. The solid was transferred into a 250 mL flask. IPA (~40 ml) was added and the resulting mixture was heated at 75° C. until all solids were dissolved to give a clear solution. Water was added slowly at 75° C. until the solution became slightly cloudy. The flask was allowed to cool to room temperature and sit at room temperature. Precipitate started to form. The mixture was stirred for 1 hr, and then filtered. The collected solid material was rinsed with IPA and dried under vacuum for 2 h. The solid material was transferred to 20 mL vials and put on freeze dry vacuum pump for 4 days to afford 410 mg of white solid material. The filtrate was concentrated and purified with ISCO 40 g column, 40 mL/min. 0-100% EtOAc/hexane. The desired product was eluted with 80% EtOAc/hexane to give 90 mg of white solid. The total combined yield from crystallization (410 mg) and ISCO purification (90 mg) was 500 mg of Example 1 (0.500 g, 0.799 mmol, 63.9% yield) as white solid. HPLC: RT=9.369 min (H₂O/CH₃CN with TFA, Sunfire C18 3.5 μm, 3.0×150 mm, gradient=15 min, wavelength=220 and 254 nm); MS(ES):m/z=620.4 [M+H⁺]; ¹H NMR (400 MHz, methanol-d₄) δ 8.65 (s, 1H), 7.61-7.53 (m, 2H), 7.51 (t, J=7.4 Hz, 1H), 7.43 (t, J=7.4 Hz, 2H), 7.37-7.20 (m, 2H), 7.04 (dd, J=7.6, 1.7 Hz, 1H), 5.37 (s, 1H), 4.94 (dd, J=14.6, 11.6 Hz, 1H), 4.79-4.67 (m, 1H), 4.32 (ddd, J=13.4, 10.0, 6.2 Hz, 1H), 3.88-3.72 (m, 1H), 3.62 (d, J=11.2 Hz, 1H), 3.24 (dt, J=11.1, 7.1 Hz, 1H), 2.53 (d, J=10.6 Hz, 1H), 2.44-2.29 (m, 1H), 2.25 (s, 3H), 1.98-1.78 (m, 2H).

Example 2

(2R,3S)-3-(Cyclopropylmethyl)-N-((7S)-3,3-difluoro-6-oxo-9-phenyl-3,4,6,7-tetrahydro-2H-[1,4]diazepino[1,7,6-ef][1,5]benzoxazepin-7-yl)-2-(3,3,3-trifluoropropyl)succinamide (2)

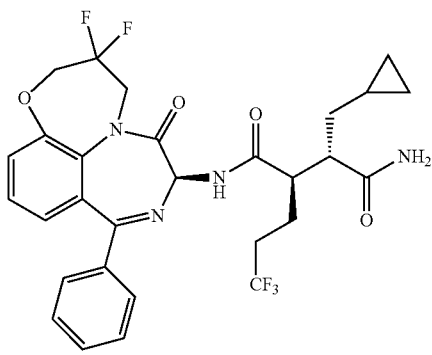

Example 2 was prepared from Intermediate A-1 and Intermediate S-2 according to the general procedure shown for Example 1. The solid was purified by preparative SFC chromatography (Berger SFC MGII, CHIRALPAK® IC 25×3 cm ID, 5 μm, 90/10 CO$_2$/MeOH, 85 mL/min) to afford Example 2. HPLC: RT=9.788 min (H$_2$O/CH$_3$CN with TFA, Sunfire C18 3.5 μm, 3.0×150 mm, gradient=15 min, wavelength=220 and 254 nm); MS(ES):m/z=593.4 [M+H$^+$]; $^1$H NMR (400 MHz, methanol-d$_4$) δ 7.67-7.61 (m, 2H), 7.56-7.50 (m, 1H), 7.47-7.41 (m, 2H), 7.41-7.26 (m, 2H), 7.09 (dd, J=7.5, 1.8 Hz, 1H), 5.57 (s, 1H), 5.05-4.87 (m, 1H), 4.79-4.71 (m, 1H), 4.35 (ddd, J=13.2, 10.3, 5.5 Hz, 1H), 3.91-3.76 (m, 1H), 2.73 (td, J=10.4, 3.9 Hz, 1H), 2.63 (td, J=10.7, 3.4 Hz, 1H), 2.53-2.37 (m, 1H), 2.31-2.15 (m, 1H), 1.88-1.65 (m, 3H), 1.25 (ddd, J=13.6, 7.5, 3.5 Hz, 1H), 0.69 (d, J=6.6 Hz, 1H), 0.50-0.39 (m, 2H), 0.17-0.09 (m, 1H), 0.07-0.02 (m, 1H).

Example 3

(2R,3S)—N-((7S)-3,3-Difluoro-6-oxo-9-phenyl-3,4,6,7-tetrahydro-2H-[1,4]diazepino[1,7,6-ef][1,5]benzoxazepin-7-yl)-3-propyl-2-(3,3,3-trifluoropropyl)succinamide (3)

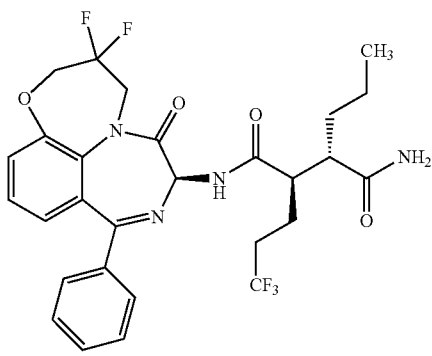

Example 3 was prepared from Intermediate A-1 and Intermediate S-3 according to the general procedure shown for Example 1. The solid was purified by preparative SFC chromatography (Berger SFC MGII, Chiral OD-H 25×3 cm ID, 5 μm, 90/10 CO$_2$/MeOH, 85 mL/min) to afford Example 3. HPLC: RT=9.729 min (H$_2$O/CH$_3$CN with TFA, Sunfire C18 3.5 μm, 3.0×150 mm, gradient=15 min, wavelength=220 and 254 nm); MS(ES):m/z=581.4 [M+H$^+$]; $^1$H NMR (400 MHz, methanol-d$_4$) δ 7.71-7.62 (m, 2H), 7.58-7.50 (m, 1H), 7.48-7.40 (m, 2H), 7.39-7.27 (m, 2H), 7.10 (dd, J=7.5, 1.8 Hz, 1H), 5.60 (s, 1H), 5.10-4.70 (m, 1H), 4.42-4.24 (m, 1H), 3.91-3.74 (m, 1H), 2.74 (td, J=10.5, 4.1 Hz, 1H), 2.57-2.42 (m, 2H), 2.32-2.14 (m, 1H), 1.88-1.72 (m, 2H), 1.69-1.57 (m, 1H), 1.52-1.36 (m, 2H), 1.34-1.21 (m, 2H), 0.98-0.86 (m, 3H).

Example 4

(2R,3R)-3-(3-Methyl-4-isoxazolyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl)succinamide (4)

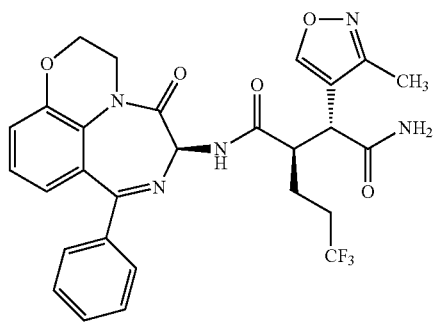

Example 4 was prepared from Intermediate A-1 and Intermediate S-6 according to the general procedure shown for Example 1. HPLC: RT=8.884 min (H$_2$O/CH$_3$CN with TFA, Sunfire C18 3.5 μm, 3.0×150 mm, gradient=15 min, wavelength=220 and 254 nm); MS(ES):m/z=570.2 [M+H$^+$]; $^1$H NMR (400 MHz, DMSO-d$_6$) δ 9.40 (d, J=7.9 Hz, 1H), 8.71 (s, 1H), 7.81 (s, 1H), 7.56-7.47 (m, 1H), 7.47-7.37 (m, 4H), 7.26-7.12 (m, 3H), 6.84 (dd, J=6.2, 3.1 Hz, 1H), 5.30 (d, J=7.7 Hz, 1H), 4.70 (d, J=13.2 Hz, 1H), 4.49 (d, J=10.6 Hz, 1H), 4.20 (td, J=11.1, 2.9 Hz, 1H), 3.55 (d, J=11.4 Hz, 1H), 3.28-3.12 (m, 2H), 2.56-2.40 (m, 1H), 2.39-2.23 (m, 1H), 2.18 (s, 3H), 1.81-1.63 (m, 2H).

Example 5

(2R,3R)—N-((6S)-5-Oxo-8-phenyl-2,3,5,6-tetrahydro[1,4]oxazino[2,3,4-jk][1,4]benzodiazepin-6-yl)-3-phenyl-2-(3,3,3-trifluoropropyl)succinamide (5)

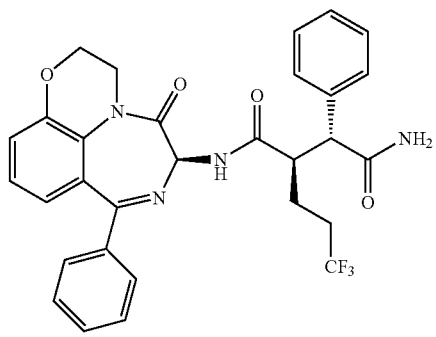

Example 5 was prepared from Intermediate A-1 and Intermediate S-5 according to the general procedure shown for Example 1. HPLC: RT=9.439 min (H₂O/CH₃CN with TFA, Sunfire C18 3.5 μm, 3.0×150 mm, gradient=15 min, wavelength=220 and 254 nm); MS(ES):m/z=565.5 [M+H$^+$]; $^1$H NMR (400 MHz, DMSO-d$_6$) δ 9.25 (d, J=7.8 Hz, 1H), 7.68 (br. s., 1H), 7.53-7.47 (m, 1H), 7.47-7.37 (m, 4H), 7.35-7.22 (m, 5H), 7.20-7.11 (m, 2H), 6.91 (br. s., 1H), 6.77 (dd, J=6.8, 2.3 Hz, 1H), 5.13 (d, J=7.8 Hz, 1H), 4.68 (d, J=13.6 Hz, 1H), 4.49 (d, J=10.5 Hz, 1H), 4.16 (td, J=11.0, 2.8 Hz, 1H), 3.69 (d, J=11.3 Hz, 1H), 3.46 (td, J=10.7, 3.4 Hz, 1H), 3.21-3.09 (m, 1H), 2.65-2.52 (m, 1H), 2.39-2.28 (m, 1H), 1.86-1.59 (m, 2H).

Example 6

(2R,3S)-3-(Cyclopropylmethyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl)succinamide (6)

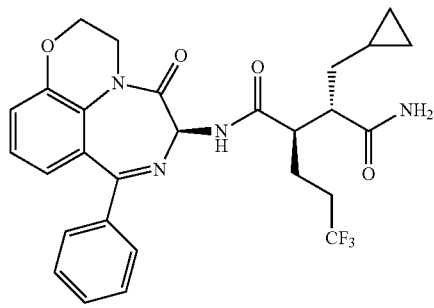

Example 6 was prepared from Intermediate A-1 and Intermediate S-2 according to the general procedure shown for Example 1. HPLC: RT=9.578 min (H₂O/CH₃CN with TFA, Sunfire C18 3.5 μm, 3.0×150 mm, gradient=15 min, wavelength=220 and 254 nm); MS(ES):m/z=543.3 [M+H$^+$]; $^1$H NMR (400 MHz, chloroform-d) δ 7.59-7.54 (m, 2H), 7.53-7.47 (m, 2H), 7.44-7.38 (m, 2H), 7.21-7.10 (m, 2H), 7.03-6.85 (m, 1H), 5.93 (br. s., 1H), 5.67 (d, J=7.9 Hz, 1H), 5.61 (br. s., 1H), 5.03-4.89 (m, 1H), 4.63-4.46 (m, 1H), 4.30 (td, J=11.2, 3.0 Hz, 1H), 3.20 (ddd, J=13.6, 11.1, 3.1 Hz, 1H), 2.79-2.54 (m, 2H), 2.42-2.12 (m, 2H), 2.02-1.77 (m, 3H), 1.48 (ddd, J=13.7, 7.9, 3.7 Hz, 1H), 0.85-0.74 (m, 1H), 0.60-0.43 (m, 2H), 0.32-0.21 (m, 1H), 0.18-0.08 (m, 1H).

Example 7

(2R,3S)—N-((6S)-5-Oxo-8-phenyl-2,3,5,6-tetrahydro[1,4]oxazino[2,3,4-jk][1,4]benzodiazepin-6-yl)-3-propyl-2-(3,3,3-trifluoropropyl)succinamide (7)

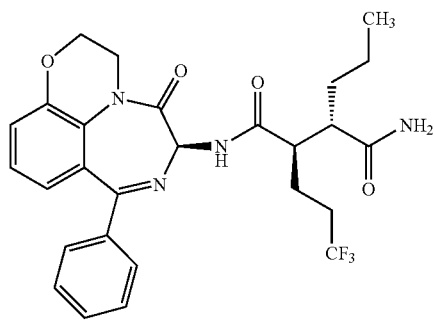

Example 7 was prepared from Intermediate A-1 and Intermediate S-3 according to the general procedure shown for Example 1. HPLC: RT=9.388 min (H₂O/CH₃CN with TFA, Sunfire C18 3.5 μm, 3.0×150 mm, gradient=15 min, wavelength=220 and 254 nm); MS(ES):m/z=531.2 [M+H$^+$]; $^1$H NMR (400 MHz, chloroform-d) δ 7.65-7.54 (m, 2H), 7.54-7.36 (m, 5H), 7.21-7.12 (m, 2H), 6.99 (dd, J=5.3, 3.7 Hz, 1H), 5.84 (br. s., 1H), 5.71 (d, J=7.7 Hz, 1H), 5.52 (br. s., 1H), 5.04-4.81 (m, 1H), 4.64-4.49 (m, 1H), 4.39-4.18 (m, 1H), 3.21 (ddd, J=13.6, 11.0, 3.1 Hz, 1H), 2.65 (dd, J=10.3, 3.5 Hz, 1H), 2.55 (dd, J=10.0, 3.2 Hz, 1H), 2.41-2.14 (m, 2H), 2.04-1.76 (m, 3H), 1.74-1.63 (m, 1H), 1.55-1.45 (m, 1H), 1.36 (dd, J=11.6, 6.5 Hz, 1H), 1.01 (t, J=7.3 Hz, 3H).

Example 8

(2R,3S)-3-(3-Fluoropropyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl)succinamide (8)

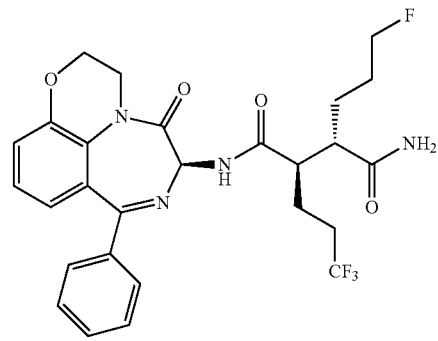

Example 8 was prepared from Intermediate A-1 and Intermediate S-4 according to the general procedure shown for Example 1. The solid was purified by preparative SFC chromatography (Berger SFC MGII, Chiral Lux Cellulose-2 25×3 cm ID, 5 μm, 83/17 CO₂/MeOH, 85 mL/min) to afford Example 8. HPLC: RT=9.019 min (H₂O/CH₃CN with TFA, Sunfire C18 3.5 μm, 3.0×150 mm, gradient=15 min, wavelength=220 and 254 nm); MS(ES):m/z=549.3 [M+H$^+$]; $^1$H NMR (400 MHz, methanol-d$_4$) δ 7.62-7.55 (m, 2H), 7.54-7.46 (m, 1H), 7.46-7.35 (m, 2H), 7.23-7.15 (m, 2H), 6.98-6.85 (m, 1H), 5.54 (s, 1H), 4.94-4.86 (m, 1H), 4.57-4.45 (m, 2H), 4.40-4.23 (m, 2H), 3.22 (ddd, J=13.6, 11.1, 3.1 Hz, 1H), 2.77 (td, J=10.5, 4.1 Hz, 1H), 2.63-2.50 (m, 2H), 2.31-2.11 (m, 1H), 1.88-1.59 (m, 6H).

Example 9

(2R,3R)-3-(4-Methyl-3-isoxazolyl)-N-((6S)-5-oxo-8-phenyl-2,3,5,6-tetrahydro[1,4]oxazino[2,3,4-jk][1,4]benzo diazepin-6-yl)-2-(3,3,3-trifluoropropyl)succinamide

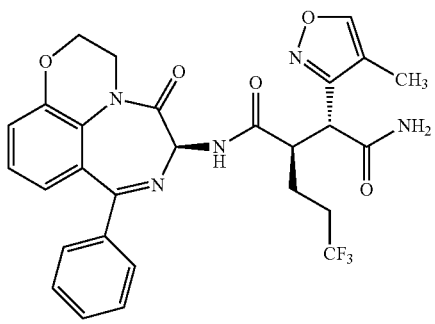

(9)

Example 9 was prepared from Intermediate A-1 and Intermediate S-7 according to the general procedure shown for Example 1. The solid was purified by preparative SFC chromatography (Berger SFC MGII, Chiral OD-H 25×3 cm ID, 5 μm, 80/20 CO₂/MeOH, 85 mL/min) to afford Example 9. HPLC: RT=3.106 min (H₂O/MeOH with 0.2% H₃PO₄, YMC S5 ODS 5 μm, 4.6×50 mm, gradient=4 min, wavelength=220 nm); MS(ES):m/z=570.1 [M+H$^+$]; $^1$H NMR (400 MHz, chloroform-d) δ 7.53-7.44 (m, 3H), 7.43-7.35 (m, 3H), 7.15-7.08 (m, 2H), 6.94-6.84 (m, 1H), 6.52 (br. s., 1H), 5.47 (d, J=7.5 Hz, 2H), 4.94-4.81 (m, 1H), 4.56-4.44 (m, 1H), 4.26 (td, J=11.2, 2.9 Hz, 1H), 4.03 (d, J=9.9 Hz, 1H), 3.40 (td, J=9.2, 5.3 Hz, 1H), 3.14 (ddd, J=13.6, 11.0, 3.1 Hz, 1H), 2.58-2.29 (m, 2H), 2.19-2.10 (m, 2H), 2.09-1.99 (m, 3H).

Example 10

(2R,3S)—N-((6S)-5-Oxo-8-phenyl-2,3,5,6-tetrahydro[1,4]oxazino[2,3,4-jk][1,4]benzodiazepin-6-yl)-2,3-bis(3,3,3-trifluoropropyl)succinamide

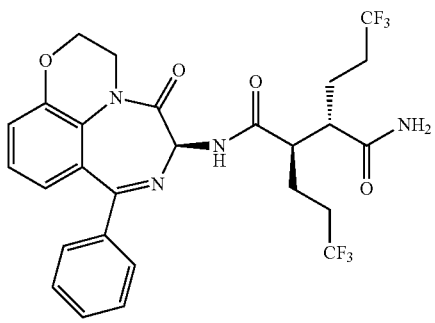

(10)

Example 10 was prepared from Intermediate B-1 and Intermediate S-1 according to the general procedure shown for Example 1. HPLC: RT=9.814 min (H₂O/CH₃CN with TFA, Sunfire C18 3.5 μm, 3.0×150 mm, gradient=15 min, wavelength=220 and 254 nm); MS(ES):m/z=585.2 [M+H$^+$]; $^1$H NMR (400 MHz, chloroform-d) δ 7.58-7.44 (m, 5H), 7.42-7.36 (m, 2H), 7.20-7.09 (m, 2H), 7.02-6.85 (m, 1H), 6.02 (br. s., 1H), 5.67 (d, J=7.7 Hz, 1H), 5.58 (br. s., 1H), 4.98-4.85 (m, 1H), 4.59-4.47 (m, 1H), 4.28 (td, J=11.2, 2.9 Hz, 1H), 3.19 (ddd, J=13.7, 11.1, 3.2 Hz, 1H), 2.71-2.58 (m, 2H), 2.33-2.03 (m, 6H), 2.00-1.83 (m, 2H).

Example 11

(2R,3S)—N-((6S)-8-(3-Methylphenyl)-5-oxo-2,3,5,6-tetrahydro[1,4]oxazino[2,3,4-jk][1,4]benzodiazepin-6-yl)-2,3-bis(3,3,3-trifluoropropyl)succinamide

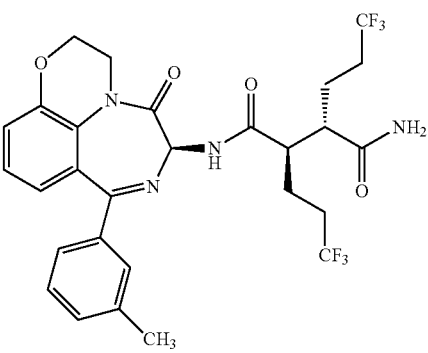

(11)

Example 11 was prepared from Intermediate C-1 and Intermediate S-1 according to the general procedure shown for Example 1. The solid was purified by preparative SFC chromatography (Berger SFC MGII, Chiral Whelk-O 25×3 cm ID, 5 μm, 85/15 CO₂/IPA, 85 mL/min) to afford Example 11. HPLC: RT=9.696 min (H₂O/CH₃CN with TFA, Sunfire C18 3.5 μm, 3.0×150 mm, gradient=15 min, wavelength=220 and 254 nm); MS(ES):m/z=599.3 [M+H$^+$]; $^1$H NMR (400 MHz, methanol-d₄) δ 9.58 (d, J=7.3 Hz, 1H), 7.45 (s, 1H), 7.37-7.27 (m, 3H), 7.24-7.15 (m, 2H), 6.97-6.91 (m, 1H), 5.57 (t, J=3.5 Hz, 1H), 4.94-4.87 (m, 1H), 4.62-4.49 (m, 1H), 4.33 (td, J=11.1, 3.1 Hz, 1H), 3.23 (ddd, J=13.7, 11.1, 3.0 Hz, 1H), 2.83 (td, J=10.3, 4.0 Hz, 1H), 2.68-2.46 (m, 2H), 2.37 (s, 3H), 2.31-2.06 (m, 3H), 1.98-1.72 (m, 4H).

Example 12

(2R,3S)—N-((6S)-8-(3-Methylphenyl)-5-oxo-2,3,5,6-tetrahydro[1,4]oxazino[2,3,4-jk][1,4]benzodiazepin-6-yl)-3-propyl-2-(3,3,3-trifluoropropyl)succinamide

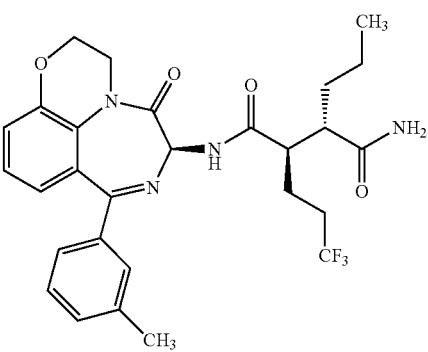

(12)

Example 12 was prepared from Intermediate C-1 and Intermediate S-3 according to the general procedure shown for Example 1. The solid was purified by preparative SFC chromatography (Berger SFC MGII, CHIRALPAK® IC 25×3 cm ID, 5 μm, 87/13 CO$_2$/MeOH, 85 mL/min) to afford Example 12. HPLC: RT=9.388 min (H$_2$O/CH$_3$CN with TFA, Sunfire C18 3.5 μm, 3.0×150 mm, gradient=15 min, wavelength=220 and 254 nm); MS(ES):m/z=545.1 [M+H$^+$]; $^1$H NMR (400 MHz, methanol-d$_4$) δ 7.46 (s, 1H), 7.37-7.30 (m, 3H), 7.22-7.14 (m, 2H), 6.98-6.82 (m, 1H), 5.54 (s, 1H), 4.96-4.88 (m, 1H), 4.61-4.51 (m, 1H), 4.34 (td, J=11.1, 3.1 Hz, 1H), 3.23 (ddd, J=13.7, 10.9, 3.1 Hz, 1H), 2.75 (td, J=10.5, 4.0 Hz, 1H), 2.55 (td, J=10.7, 3.4 Hz, 2H), 2.38 (s, 3H), 2.24 (dd, J=15.5, 4.7 Hz, 1H), 1.88-1.72 (m, 2H), 1.72-1.61 (m, 1H), 1.52-1.36 (m, 2H), 1.00-0.92 (m, 3H).

Example 13

(2R,3R)—N-((6S)-8-(3-Methylphenyl)-5-oxo-2,3,5,6-tetrahydro[1,4]oxazino[2,3,4-jk][1,4]benzodiazepin-6-yl)-3-phenyl-2-(3,3,3-trifluoropropyl)succinamide (13)

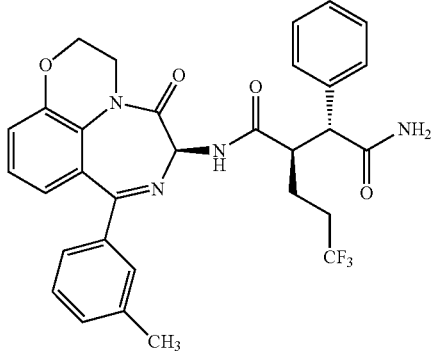

Example 13 was prepared from Intermediate C-1 and Intermediate S-5 according to the general procedure shown for Example 1. The solid was purified by preparative SFC chromatography (Berger SFC MGII, Whelk-O RR 25×3 cm ID, 5 μm, 80/20 CO$_2$/EtOH, 85 mL/min) to afford Example 13. HPLC: RT=9.551 min (H$_2$O/CH$_3$CN with TFA, Sunfire C18 3.5 μm, 3.0×150 mm, gradient=15 min, wavelength=220 and 254 nm); MS(ES):m/z=579.5 [M+H$^+$]; $^1$H NMR (400 MHz, methanol-d$_4$) δ 7.52-7.40 (m, 2H), 7.36-7.23 (m, 7H), 7.22-7.07 (m, 3H), 6.82 (dd, J=5.8, 3.4 Hz, 1H), 5.08 (s, 1H), 4.95-4.89 (m, 1H), 4.61-4.47 (m, 1H), 4.29 (td, J=11.1, 3.0 Hz, 1H), 3.73 (d, J=11.2 Hz, 1H), 3.47-3.36 (m, 1H), 3.23-3.09 (m, 1H), 2.71-2.53 (m, 1H), 2.43-2.37 (m, 4H), 2.37-2.25 (m, 1H), 2.01-1.78 (m, 2H).

Example 14

(2R,3S)—N-((6S)-8-(3-Chlorophenyl)-5-oxo-2,3,5,6-tetrahydro[1,4]oxazino[2,3,4-jk][1,4]benzodiazepin-6-yl)-2,3-bis(3,3,3-trifluoropropyl)succinamide (14)

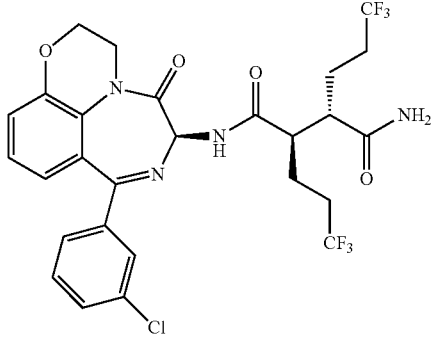

Example 14 was prepared from Intermediate D-1 and Intermediate S-1 according to the general procedure shown for Example 1. The solid was purified by preparative SFC chromatography (Berger SFC MGII, Chiral AD-H 25×3 cm ID, 5 μm, 90/10 CO$_2$/MeOH, 180 mL/min) to afford Example 14. HPLC: RT=9.886 min (H$_2$O/CH$_3$CN with TFA, Sunfire C18 3.5 μm, 3.0×150 mm, gradient=15 min, wavelength=220 and 254 nm); MS(ES):m/z=619.0 [M+H$^+$]; $^1$H NMR (400 MHz, DMSO-d$_6$) δ ppm 9.53 (1H, d, J=7.5 Hz), 7.64 (1H, s), 7.56-7.62 (2H, m), 7.42-7.50 (1H, m), 7.37-7.42 (1H, m), 7.20-7.30 (2H, m), 7.13 (1H, s), 6.93 (1H, tdd, J=4.5, 4.5, 4.4, 4.2 Hz), 5.52 (1H, d, J=7.7 Hz), 4.72 (1H, d, J=13.0 Hz), 4.49-4.56 (1H, m), 4.24 (1H, td, J=11.1, 3.0 Hz), 3.17-3.26 (1H, m), 2.83 (1H, td, J=10.1, 4.5 Hz), 2.47 (1H, d, J=3.7 Hz), 2.34-2.44 (1H, m), 2.05-2.29 (3H, m), 1.69-1.82 (1H, m), 1.53-1.68 (3H, m).

Example 15

(2R,3S)—N-((6S)-8-(3-Chlorophenyl)-5-oxo-2,3,5,6-tetrahydro[1,4]oxazino[2,3,4-jk][1,4]benzodiazepin-6-yl)-3-propyl-2-(3,3,3-trifluoropropyl)succinamide (15)

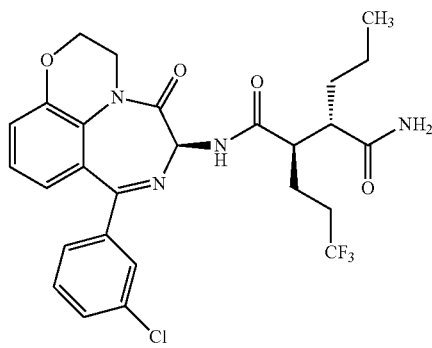

Example 15 was prepared from Intermediate D-1 and Intermediate S-3 according to the general procedure shown for Example 1. The solid was purified by preparative SFC chromatography (Berger SFC MGII, Chiral IC 25×3 cm ID, 5 μm, 90/10 CO$_2$/MeOH, 85 mL/min) to afford Example 15. HPLC: RT=9.556 min (H$_2$O/CH$_3$CN with TFA, Sunfire C18 3.5 μm, 3.0×150 mm, gradient=15 min, wavelength=220 and 254 nm); MS(ES):m/z=565.2 [M+H$^+$]; $^1$H NMR (400 MHz, MeOD) δ ppm 7.68 (1H, t, J=1.9 Hz), 7.49-7.53 (1H, m), 7.42-7.47 (1H, m), 7.36-7.42 (1H, m), 7.18-7.28 (2H, m), 6.90-6.98 (1H, m), 5.54 (1H, s), 4.86-4.92 (1H, m), 4.51-4.58 (1H, m), 4.32 (1H, td, J=11.2, 3.0 Hz), 3.21 (1H, ddd, J=13.6, 11.0, 3.1 Hz), 2.73 (1H, td, J=10.5, 4.1 Hz), 2.42-2.61 (2H, m), 2.12-2.32 (1H, m), 1.70-1.87 (2H, m), 1.58-1.69 (1H, m), 1.33-1.54 (2H, m), 1.22-1.33 (1H, m), 0.93 (3H, t, J=7.3 Hz).

Example 16

(2R,3R)—N-((6S)-8-(3-Chlorophenyl)-5-oxo-2,3,5,6-tetrahydro[1,4]oxazino[2,3,4-jk][1,4]benzodiazepin-6-yl)-3-(3-methyl-4-isoxazolyl)-2-(3,3,3-trifluoropropyl)succinamide

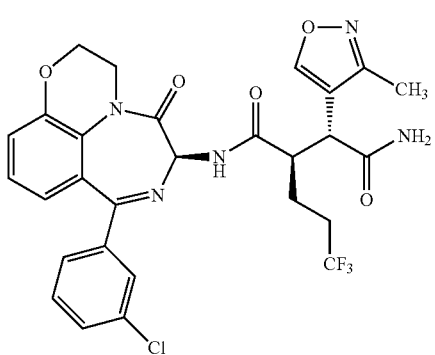

(16)

Example 1 was prepared from Intermediate D-1 and Intermediate S-6 according to the general procedure shown for Example 1. HPLC: RT=9.624 min (H$_2$O/CH$_3$CN with TFA, Sunfire C18 3.5 μm, 3.0×150 mm, gradient=15 min, wavelength=220 and 254 nm); MS(ES):m/z=604.4 [M+H$^+$]; $^1$H NMR (400 MHz, methanol-d$_4$) δ 8.66 (s, 1H), 7.56 (d, J=1.1 Hz, 1H), 7.50 (td, J=4.5, 2.2 Hz, 1H), 7.45-7.37 (m, 2H), 7.23-7.08 (m, 2H), 6.91-6.77 (m, 1H), 5.30 (s, 1H), 4.91-4.86 (m, 1H), 4.59-4.48 (m, 1H), 4.30 (td, J=11.1, 2.9 Hz, 1H), 3.63 (d, J=11.2 Hz, 1H), 3.26-3.12 (m, 2H), 2.61 (dt, J=10.8, 5.5 Hz, 1H), 2.40-2.29 (m, 1H), 2.25 (s, 3H), 1.96-1.81 (m, 2H).

Example 17

(2R,3S)—N-((6S)-5-Oxo-8-phenyl-2,3,5,6-tetrahydro[1,4]oxazino[2,3,4-jk][1,4]benzodiazepin-6-yl)-2-propyl-3-(3,3,3-trifluoropropyl)succinamide

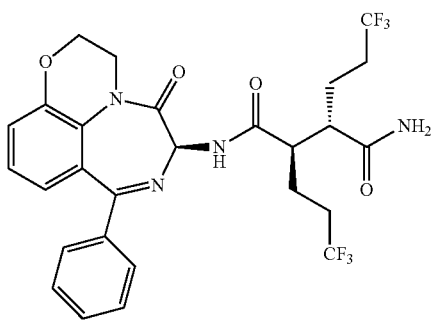

(17)

Example 17 was prepared from Intermediate B-1 and Intermediate S-9 according to the general procedure shown for Example 1. HPLC: RT=9.24 min (H$_2$O/CH$_3$CN with TFA, Sunfire C18 3.5 μm, 3.0×150 mm, gradient=15 min, wavelength=220 and 254 nm); MS(ES):m/z=531.3 [M+H$^+$]; $^1$H NMR (400 MHz, DMSO-d$_6$) δ 9.36 (d, J=8.4 Hz, 1H), 7.58-7.47 (m, 4H), 7.46-7.34 (m, 2H), 7.27-7.14 (m, 2H), 7.00 (br. s., 1H), 6.92-6.77 (m, 1H), 5.54 (d, J=8.1 Hz, 1H), 4.73 (d, J=13.2 Hz, 1H), 4.51 (d, J=10.3 Hz, 1H), 4.24 (td, J=11.1, 2.9 Hz, 1H), 3.25-3.11 (m, 1H), 2.74 (t, J=10.8 Hz, 1H), 2.41 (td, J=10.2, 3.3 Hz, 1H), 2.25-2.08 (m, 2H), 1.82-1.71 (m, 1H), 1.64 (d, J=11.0 Hz, 1H), 1.47-1.17 (m, 4H), 0.82 (t, J=6.9 Hz, 3H).

Example 18

(2R,3S)-2,3-Bis(cyclopropylmethyl)-N-((6S)-5-oxo-8-phenyl-2,3,5,6-tetrahydro[1,4]oxazino[2,3,4-jk][1,4]benzodiazepin-6-yl)succinamide

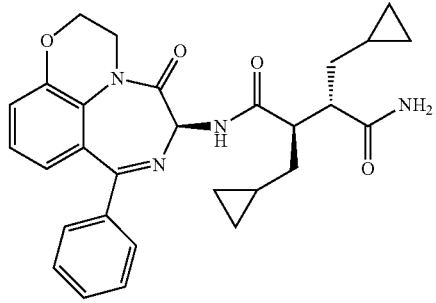

(18)

Example 18 was prepared from Intermediate B-1 and Intermediate S-8 according to the general procedure shown for Example 1. HPLC: RT=8.88 min (H$_2$O/CH$_3$CN with TFA, Sunfire C18 3.5 μm, 3.0×150 mm, gradient=15 min, wavelength=220 and 254 nm); MS(ES):m/z=501.2 [M+H$^+$]; $^1$H NMR (400 MHz, chloroform-d) δ 7.61-7.53 (m, 2H), 7.47 (ddd, J=7.5, 5.1, 1.9 Hz, 2H), 7.43-7.33 (m, 2H), 7.14 (d, J=4.6 Hz, 2H), 6.97 (t, J=4.6 Hz, 1H), 6.00 (br. s., 1H), 5.69 (d, J=7.9 Hz, 1H), 5.47 (br. s., 1H), 5.00-4.83 (m, 1H), 4.62-4.46 (m, 1H), 4.24 (td, J=11.2, 2.9 Hz, 1H), 3.27-3.13 (m, 1H), 2.67 (ddd, J=13.0, 9.8, 3.5 Hz, 2H), 1.91-1.70 (m, 2H), 1.43 (ddd, J=13.7, 7.8, 3.6 Hz, 1H), 1.28-1.10 (m, 1H), 0.95-0.82 (m, 1H), 0.82-0.69 (m, 1H), 0.58-0.40 (m, 4H), 0.21 (dd, J=8.6, 4.2 Hz, 1H), 0.17-0.04 (m, 3H).

Example 19

(2R,3S)—N-((7S)-6-Oxo-9-phenyl-3,4,6,7-tetrahydro-2H-[1,4]diazepino[1,7,6-ef][1,5]benzoxazepin-7-yl)-2,3-bis(3,3,3-trifluoropropyl)succinamide

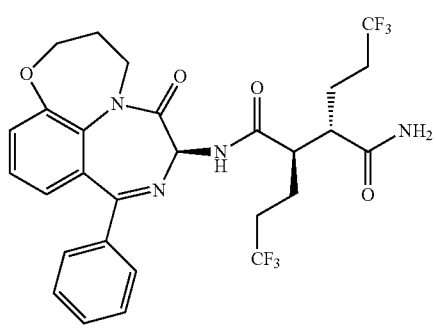

(19)

Example 19 was prepared from Intermediate F-1 and Intermediate S-1 according to the general procedure shown for Example 1. The solid was purified by preparative SFC chromatography (Berger SFC MGII, CHIRALPAK® IC 25×3 cm ID, 5 µm, 90/10 CO₂/MeOH, 50 mL/min) to afford Example 19. HPLC: RT=9.989 min (H₂O/CH₃CN with TFA, Sunfire C18 3.5 µm, 3.0×150 mm, gradient=15 min, wavelength=220 and 254 nm); MS(ES):m/z=599.0 [M+H⁺]; ¹H NMR (400 MHz, methanol-d₄) δ 7.69-7.61 (m, 2H), 7.54-7.47 (m, 1H), 7.47-7.37 (m, 2H), 7.30-7.22 (m, 2H), 7.01 (dd, J=5.5, 3.7 Hz, 1H), 5.52 (s, 1H), 4.53-4.37 (m, 2H), 4.29 (ddd, J=9.2, 5.9, 2.8 Hz, 1H), 3.46 (ddd, J=13.5, 11.4, 5.0 Hz, 1H), 2.80 (td, J=10.4, 4.1 Hz, 1H), 2.66-2.49 (m, 2H), 2.33-2.10 (m, 5H), 1.96-1.72 (m, 4H).

Example 20

(2R,3R)-3-(3-Methyl-4-isoxazolyl)-N-((7S)-6-oxo-9-phenyl-3,4,6,7-tetrahydro-2H-[1,4]diazepino[1,7,6-ef][1,5]benzoxazepin-7-yl)-2-(3,3,3-trifluoropropyl)succinamide (20)

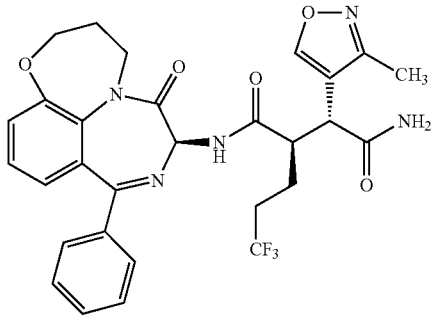

Example 20 was prepared from Intermediate F-1 and Intermediate S-6 according to the general procedure shown for Example 1. HPLC: RT=9.028 min (H₂O/CH₃CN with TFA, Sunfire C18 3.5 µm, 3.0×150 mm, gradient=15 min, wavelength=220 and 254 nm); MS(ES):m/z=584.3 [M+H⁺]; ¹H NMR (400 MHz, chloroform-d) δ 8.75 (s, 1H), 7.75 (bs, 1H), 7.54 (d, J=7.0 Hz, 2H), 7.50-7.36 (m, 3H), 7.22-7.10 (m, 2H), 6.99 (dd, J=6.8, 2.4 Hz, 1H), 5.85 (br. s., 1H), 5.76 (br. s., 1H), 5.46 (d, J=7.5 Hz, 1H), 4.48 (dd, J=13.9, 4.0 Hz, 1H), 4.37-4.19 (m, 2H), 3.59 (d, J=8.1 Hz, 1H), 3.46-3.34 (m, 1H), 3.25 (t, J=7.4 Hz, 1H), 2.47-2.21 (m, 6H), 2.17 (d, J=13.9 Hz, 1H), 2.01-1.92 (m, 1H), 1.92-1.80 (m, 1H).

Example 21

(2R,3R)—N-((7S)-6-Oxo-9-phenyl-3,4,6,7-tetrahydro-2H-[1,4]diazepino[1,7,6-ef][1,5]benzoxazepin-7-yl)-3-phenyl-2-(3,3,3-trifluoropropyl)succinamide (21)

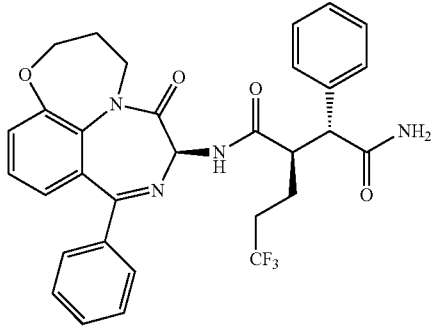

Example 21 was prepared from Intermediate F-1 and Intermediate S-5 according to the general procedure shown for Example 1. The solid was purified by preparative SFC chromatography (Berger SFC MGII, Lux Cellulose-2 25×3 cm ID, 5 µm, 80/20 CO₂/MeOH, 85 mL/min) to afford Example 21. HPLC: RT=9.661 min (H₂O/CH₃CN with TFA, Sunfire C18 3.5 µm, 3.0×150 mm, gradient=15 min, wavelength=220 and 254 nm); MS(ES):m/z=579.2 [M+H⁺]; ¹H NMR (400 MHz, chloroform-d) δ 7.53-7.31 (m, 11H), 7.20-7.06 (m, 2H), 6.93 (dd, J=7.2, 2.1 Hz, 1H), 5.61 (br. s., 1H), 5.50 (br. s., 1H), 5.37 (d, J=7.7 Hz, 1H), 4.50-4.40 (m, 1H), 4.36-4.20 (m, 2H), 3.70 (d, J=9.2 Hz, 1H), 3.42-3.19 (m, 2H), 2.39-2.20 (m, 3H), 2.18-2.08 (m, 1H), 2.05-1.90 (m, 2H).

Example 22

(2R,3S)—N-((7S)-6-Oxo-9-phenyl-3,4,6,7-tetrahydro-2H-[1,4]diazepino[1,7,6-ef][1,5]benzoxazepin-7-yl)-3-propyl-2-(3,3,3-trifluoropropyl)succinamide (22)

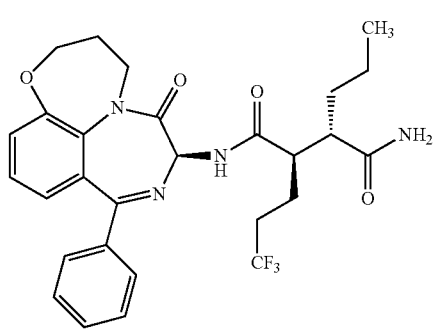

Example 22 was prepared from Intermediate F-1 and Intermediate S-3 according to the general procedure shown for Example 1. The solid was purified by preparative SFC chromatography (Berger SFC MGII, CHIRALPAK® IC 25×2.1 cm ID, 5 µm, 85/15 CO₂/MeOH, 40 mL/min) to afford Example 22. HPLC: RT=9.566 min (H₂O/CH₃CN with TFA, Sunfire C18 3.5 µm, 3.0×150 mm, gradient=15 min, wavelength=220 and 254 nm); MS(ES):m/z=545.3 [M+H⁺]; ¹H NMR (400 MHz, chloroform-d) δ 7.68-7.58 (m, 2H), 7.57-7.45 (m, 2H), 7.43-7.34 (m, 2H), 7.22-7.11 (m, 2H), 7.02 (dd, J=7.0, 2.2 Hz, 1H), 5.89 (br. s., 1H), 5.62 (d, J=7.7 Hz, 1H), 5.50 (br. s., 1H), 4.58-4.48 (m, 1H), 4.43-4.22 (m, 2H), 3.47-3.32 (m, 1H), 2.64 (td, J=9.8, 3.7 Hz, 1H), 2.52 (td, J=9.9, 3.7 Hz, 1H), 2.39-2.10 (m, 4H), 2.01-1.73 (m, 3H), 1.73-1.62 (m, 1H), 1.52-1.41 (m, 1H), 1.40-1.23 (m, 1H), 0.98 (t, J=7.3 Hz, 3H).

Example 23

(2R,3S)-3-(Cyclopropylmethyl)-N-((7S)-6-oxo-9-phenyl-3,4,6,7-tetrahydro-2H-[1,4]diazepino[1,7,6-ef][1,5]benzoxazepin-7-yl)-2-(3,3,3-trifluoropropyl)succinamide (23)

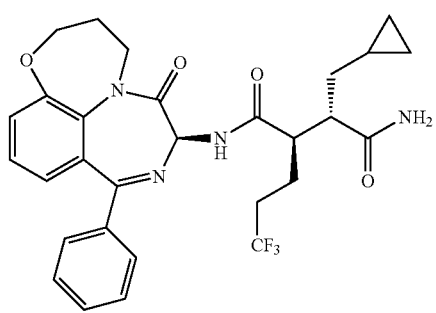

Example 23 was prepared from Intermediate F-1 and Intermediate S-2 according to the general procedure shown for Example 1. The solid was purified by preparative SFC chromatography (Berger SFC MGII, CHIRALPAK® IC 25×3.0 cm ID, 5 μm, 85/15 CO$_2$/MeOH, 85 mL/min) to afford Example 23. HPLC: RT=9.589 min (H$_2$O/CH$_3$CN with TFA, Sunfire C18 3.5 μm, 3.0×150 mm, gradient=15 min, wavelength=220 and 254 nm); MS(ES):m/z=557.1 [M+H$^+$]; $^1$H NMR (400 MHz, chloroform-d) δ 7.67-7.56 (m, 2H), 7.54-7.45 (m, 2H), 7.45-7.34 (m, 2H), 7.23-7.10 (m, 2H), 7.01 (dd, J=7.0, 2.2 Hz, 1H), 5.90 (br. s., 1H), 5.69-5.51 (m, 2H), 4.58-4.45 (m, 1H), 4.40-4.22 (m, 2H), 3.41 (ddd, J=13.5, 11.6, 4.8 Hz, 1H), 2.75-2.54 (m, 1H), 2.40-2.11 (m, 4H), 2.00-1.78 (m, 3H), 1.48 (ddd, J=13.8, 7.7, 3.6 Hz, 1H), 0.82-0.68 (m, 1H), 0.50 (ddt, J=16.4, 8.1, 4.2 Hz, 2H), 0.28-0.18 (m, 1H), 0.16-0.04 (m, 1H).

Example 24

(2R,3R)-3-(3-Methyl-4-isoxazolyl)-N-((6S)-5-oxo-8-phenyl-2,3,5,6-tetrahydro-1H-[1,4]diazepino[1,7,6-de]quinoxalin-6-yl)-2-(3,3,3-trifluoropropyl)succinamide (24)

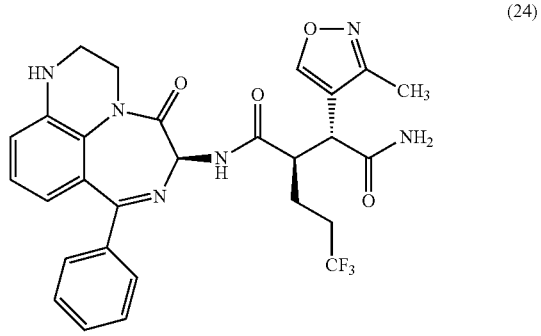

Example 24 was prepared from Intermediate G-1 and Intermediate S-6 according to the general procedure shown for Example 1. HPLC: RT=8.133 min (H$_2$O/CH$_3$CN with TFA, Sunfire C18 3.5 μm, 3.0×150 mm, gradient=15 min, wavelength=220 and 254 nm); MS(ES):m/z=569.0 [M+H$^+$]; $^1$H NMR (400 MHz, methanol-d$_4$) δ 8.69 (s, 1H), 7.60-7.53 (m, 2H), 7.53-7.46 (m, 1H), 7.46-7.36 (m, 2H), 7.01 (t, J=7.9 Hz, 1H), 6.87 (dd, J=8.1, 1.3 Hz, 1H), 6.49 (dd, J=7.6, 1.2 Hz, 1H), 5.33 (s, 1H), 4.85-4.76 (m, 1H), 3.65 (d, J=11.2 Hz, 1H), 3.61-3.53 (m, 1H), 3.48-3.37 (m, 1H), 3.25 (dt, J=11.0, 7.2 Hz, 1H), 2.97-2.85 (m, 1H), 2.70-2.51 (m, 1H), 2.43-2.32 (m, 1H), 2.31-2.20 (m, 3H), 1.99-1.77 (m, 2H).

Example 25

(2R,3S)—N-((6S)-5-Oxo-8-phenyl-2,3,5,6-tetrahydro-1H-[1,4]diazepino[1,7,6-de]quinoxalin-6-yl)-3-propyl-2-(3,3,3-trifluoropropyl)succinamide (25)

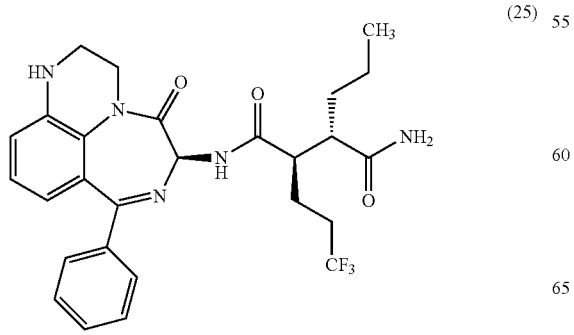

Example 25 was prepared from Intermediate G-1 and Intermediate S-3 according to the general procedure shown for Example 1. The solid was purified by preparative SFC chromatography (Berger SFC MGII, Chiral IC 25×3.0 cm ID, 5 μm, 85/15 CO$_2$/MeOH, 85 mL/min) to afford Example 25. HPLC: RT=8.356 min (H$_2$O/CH$_3$CN with TFA, Sunfire C18 3.5 μm, 3.0×150 mm, gradient=15 min, wavelength=220 and 254 nm); MS(ES):m/z=530.09 [M+H$^+$]; $^1$H NMR (400 MHz, DMSO-d$_6$) δ ppm 9.33 (1H, d, J=7.3 Hz), 7.55-7.59 (2H, m), 7.47-7.54 (2H, m), 7.40-7.46 (2H, m), 6.99-7.06 (1H, m), 6.94 (1H, br. s.), 6.87 (1H, dd, J=8.0, 1.2 Hz), 6.74 (1H, d, J=4.4 Hz), 6.44 (1H, dd, J=7.7, 1.1 Hz), 5.40 (1H, d, J=7.3 Hz), 4.68 (1H, d, J=9.7 Hz), 3.53 (1H, d, J=11.7 Hz), 3.15-3.25 (1H, m), 2.83 (1H, td, J=11.9, 3.2 Hz), 2.64-2.76 (1H, m), 2.52-2.59 (1H, m), 2.35-2.43 (1H, m), 2.17-2.31 (1H, m), 1.54-1.64 (2H, m), 1.42-1.53 (1H, m), 1.06-1.32 (3H, m), 0.83 (3H, t, J=6.9 Hz).

Example 26

(2R,3S)-3-(Cyclopropylmethyl)-N-((6S)-5-oxo-8-phenyl-2,3,5,6-tetrahydro-1H-[1,4]diazepino[1,7,6-de]quinoxalin-6-yl)-2-(3,3,3-trifluoropropyl)succinamide (26)

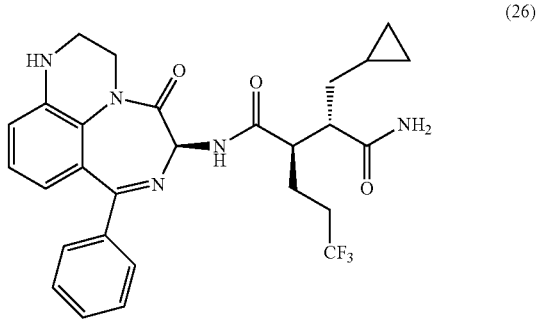 [SMILES: NC(=O)[C@@H](CC1CC1)[C@@H](CCC(F)(F)F)C(=O)N[C@H]1N=C(c2ccccc2)c2cccc3c2N(CCO3)C1=O]

Example 26 was prepared from Intermediate G-1 and Intermediate S-2 according to the general procedure shown for Example 1. HPLC: RT=8.423 min (H$_2$O/CH$_3$CN with TFA, Sunfire C18 3.5 μm, 3.0×150 mm, gradient=15 min, wavelength=220 and 254 nm); MS(ES):m/z=542.5 [M+H$^+$]; NMR (400 MHz, DMSO-d$_6$) δ ppm 9.30 (1H, d, J=7.26 Hz), 7.28-7.73 (6H, m), 7.02 (1H, t, J=7.81 Hz), 6.96 (1H, br. s.), 6.87 (1H, d, J=7.92 Hz), 6.74 (1H, d, J=3.74 Hz), 6.43 (1H, d, J=7.48 Hz), 5.37 (1H, d, J=7.04 Hz), 4.68 (1H, d, J=11.44 Hz), 3.53 (1H, d, J=11.22 Hz), 3.20 (1H, td, J=11.50, 3.19 Hz), 2.83 (1H, t, J=11.55 Hz), 2.64-2.76 (1H, m), 2.14-2.36 (1H, m), 1.43-1.69 (3H, m), 1.08 (1H, dd, J=12.65, 7.37 Hz), 0.58 (1H, br. s.), 0.34 (2H, d, J=6.82 Hz), 0.03 (1H, d, J=8.36 Hz), −0.16-−0.03 (1H, m).

Example 27

(2R,3R)—N-((6S)-5-Oxo-8-phenyl-2,3,5,6-tetrahydro-1H-[1,4]diazepino[1,7,6-de]quinoxalin-6-yl)-3-phenyl-2-(3,3,3-trifluoropropyl)succinamide (27)

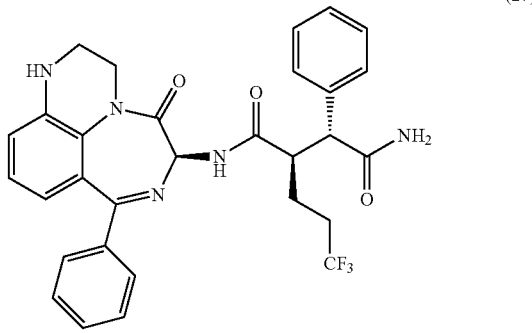

Example 27 was prepared from Intermediate G-1 and Intermediate S-5 according to the general procedure shown for Example 1. HPLC: RT=8.744 min (H$_2$O/CH$_3$CN with TFA, Sunfire C18 3.5 μm, 3.0×150 mm, gradient=15 min, wavelength=220 and 254 nm); MS(ES):m/z=564.4 [M+H$^+$]; $^1$H NMR (400 MHz, methanol-d$_4$) δ 7.51-7.34 (m, 7H), 7.34-7.17 (m, 3H), 6.96 (t, J=7.9 Hz, 1H), 6.82 (dd, J=8.1, 1.1 Hz, 1H), 6.41 (dd, J=7.7, 1.1 Hz, 1H), 5.08 (s, 1H), 4.78 (d, J=1.8 Hz, 1H), 3.70 (d, J=11.2 Hz, 1H), 3.53 (d, J=10.6 Hz, 1H), 3.45-3.36 (m, 2H), 2.85 (td, J=12.0, 3.3 Hz, 1H), 2.67-2.49 (m, 1H), 2.33 (td, J=10.3, 6.3 Hz, 1H), 1.98-1.69 (m, 2H).

Example 28

(2R,3S)—N-((6S)-5-Oxo-8-phenyl-2,3,5,6-tetrahydro-1H-[1,4]diazepino[1,7,6-de]quinoxalin-6-yl)-2,3-bis(3,3,3-trifluoropropyl)succinamide (28)

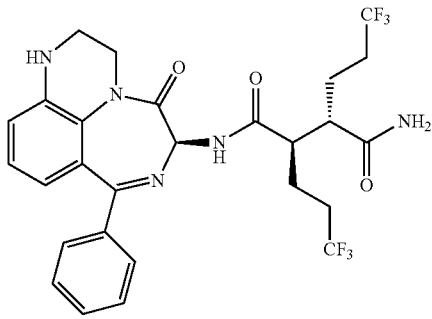

Example 28 was prepared from Intermediate G-1 and Intermediate S-1 according to the general procedure shown for Example 1. HPLC: RT=8.751 min (H$_2$O/CH$_3$CN with TFA, Sunfire C18 3.5 μm, 3.0×150 mm, gradient=15 min, wavelength=220 and 254 nm); MS(ES):m/z=584.2 [M+H$^+$]; $^1$H NMR (400 MHz, DMSO-d$_6$) δ ppm 9.47 (1H, d, J=7.7 Hz), 7.65 (1H, d, J=1.5 Hz), 7.46-7.58 (3H, m), 7.37-7.45 (2H, m), 7.13 (1H, s), 6.98-7.06 (1H, m), 6.87 (1H, dd, J=8.1, 1.3 Hz), 6.74 (1H, d, J=4.4 Hz), 6.44 (1H, dd, J=7.7, 1.3 Hz), 5.44 (1H, d, J=7.5 Hz), 4.69 (1H, d, J=9.5 Hz), 3.47-3.59 (1H, m), 3.22 (1H, td, J=11.7, 3.9 Hz), 2.75-2.91 (2H, m), 2.38-2.47 (1H, m), 2.05-2.33 (3H, m), 1.50-1.83 (4H, m).

Example 29

(2R,3S)—N-((6S)-8-(3-Chlorophenyl)-5-oxo-2,3,5,6-tetrahydro-1H-[1,4]diazepino[1,7,6-de]quinoxalin-6-yl)-2,3-bis(3,3,3-trifluoropropyl)succinamide (29)

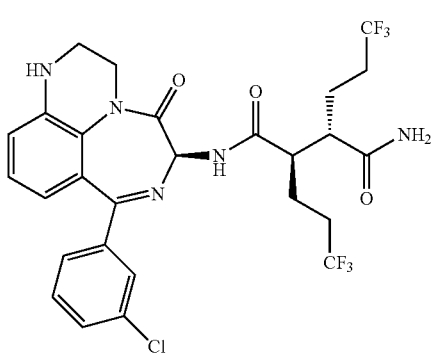

Example 29 was prepared from Intermediate E-1 and Intermediate S-1 according to the general procedure shown for Example 1. The solid was purified by preparative SFC chromatography (Berger SFC MGII, Chiral IA 25×2.1 cm ID, 5 μm, 88/12 CO$_2$/MeOH, 60 mL/min) to afford Example 29. HPLC: RT=9.409 min (H$_2$O/CH$_3$CN with TFA, Sunfire C18 3.5 μm, 3.0×150 mm, gradient=15 min, wavelength=220 and 254 nm); MS(ES):m/z=618.2 [M+H$^+$]; $^1$H NMR (400 MHz, DMSO-d$_6$) δ 9.49 (d, J=7.5 Hz, 1H), 7.70-7.56 (m, 3H), 7.51-7.41 (m, 2H), 7.13 (s, 1H), 7.05 (t, J=7.8 Hz, 1H), 6.89 (dd, J=8.0, 1.2 Hz, 1H), 6.78 (d, J=4.4 Hz, 1H), 6.47 (dd, J=7.6, 1.2 Hz, 1H), 5.45 (d, J=7.5 Hz, 1H), 4.68 (d, J=9.7 Hz, 1H), 3.53 (d, J=11.9 Hz, 1H), 3.27-3.12 (m, 1H), 2.94-2.77 (m, 2H), 2.47-2.38 (m, 2H), 2.32-2.08 (m, 3H), 1.80-1.51 (m, 4H).

Example 30

(2R,3S)—N-((6S)-8-(3-Methylphenyl)-5-oxo-2,3,5,6-tetrahydro-1H-[1,4]diazepino[1,7,6-de]quinoxalin-6-yl)-2,3-bis(3,3,3-trifluoropropyl)succinamide (30)

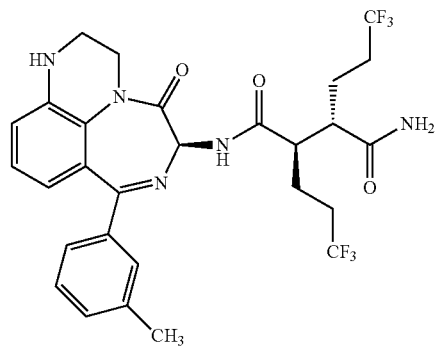

Example 30 was prepared from Intermediate F-1 and Intermediate S-1 according to the general procedure shown for Example 1. The solid was purified by preparative SFC chromatography (Berger SFC MGII, Chiral IA 25×2.1 cm ID, 5 μm, 88/12 CO$_2$/MeOH, 60 mL/min) to afford Example 30. HPLC: RT=9.126 min (H$_2$O/CH$_3$CN with TFA, Sunfire C18 3.5 μm, 3.0×150 mm, gradient=15 min, wavelength=220 and 254 nm); MS(ES):m/z=598.2 [M+H$^+$]; $^1$H NMR (400 MHz, DMSO-d$_6$) δ 9.47 (d, J=7.5 Hz, 1H), 7.65 (br. s., 1H), 7.41 (s, 1H), 7.36-7.23 (m, 3H), 7.13 (s, 1H), 7.03 (t, J=7.8 Hz, 1H), 6.87 (dd, J=8.1, 1.3 Hz, 1H), 6.74 (d, J=4.4 Hz, 1H), 6.44 (dd, J=7.6, 1.2 Hz, 1H), 5.44 (d, J=7.5 Hz, 1H), 4.69 (d, J=10.1 Hz, 1H), 3.53 (d, J=11.9 Hz, 1H), 3.27-3.09 (m, 2H), 2.92-2.75 (m, 2H), 2.47 (d, J=4.0 Hz, 2H), 2.32 (s, 3H), 2.27-2.07 (m, 3H), 1.80-1.51 (m, 4H).

Example 31

(2R,3S)—N-((6S)-1-(2-Methoxyethyl)-5-oxo-8-phenyl-2,3,5,6-tetrahydro-1H-[1,4]diazepino[1,7,6-de]quinoxalin-6-yl)-2,3-bis(3,3,3-trifluoropropyl)succinamide (31)

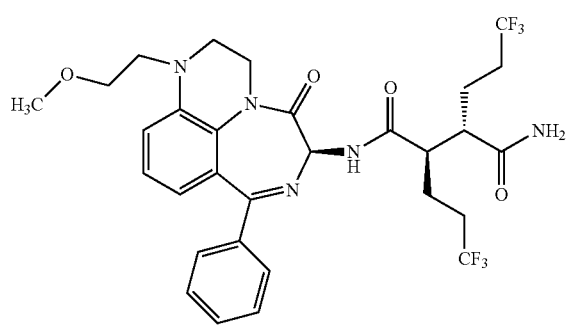

Preparation 31A: (3-((4-Methoxybenzyl)(2-methoxyethyl)amino)-2-nitrophenyl)(phenyl)methanone (31A)

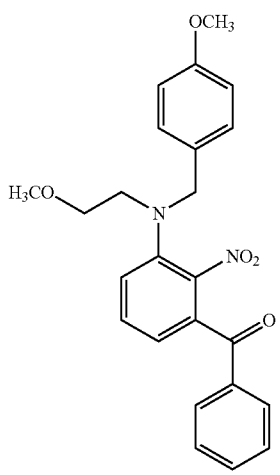

(3-Chloro-2-nitrophenyl)(phenyl)methanone (0.85 g, 3.25 mmol) and 2-methoxy-N-(4-methoxybenzyl)ethanamine (3.17 g, 16.24 mmol) were heated at 100° C. for 16 h. The reaction mixture was partitioned between water (50 mL) and DCM (50 mL), extracted 3×50 mL DCM, dried over Na₂SO₄, and purified using silica gel chromatography (30 to 50% ethylacetate/hexanes) to afford Preparation 31A (0.78 g, 1.855 mmol, 57.1% yield) as a brown oil. ¹H NMR (500 MHz, chloroform-d) δ 7.89-7.75 (m, 2H), 7.69-7.59 (m, 1H), 7.56-7.42 (m, 4H), 7.28-7.19 (m, 2H), 7.12 (dd, J=5.0, 3.9 Hz, 1H), 6.90-6.77 (m, 2H), 4.30 (s, 2H), 3.86-3.76 (m, 4H), 3.49-3.40 (m, 2H), 3.29-3.18 (m, 4H).

Preparation 31B: (2-Amino-3-((4-methoxybenzyl)(2-methoxyethyl)amino)phenyl)(phenyl)methanone (31B)

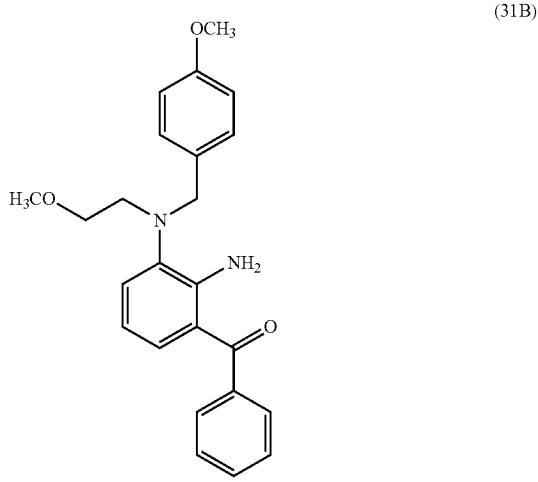 [SMILES: COCCN(Cc1ccc(OC)cc1)c1cccc(C(=O)c2ccccc2)c1N]

(3-((4-Methoxybenzyl)(2-methoxyethyl)amino)-2-nitrophenyl)(phenyl)methanone (0.70 g, 1.665 mmol), zinc (1.09 g, 16.65 mmol), and ammonium chloride (0.89 g, 16.65 mmol) in EtOH (40 mL) and water (20 mL) was heated to 90° C. for 5 minutes. The reaction mixture was filtered through CELITE®, partitioned between water and DCM, extracted 3×10 mL DCM, dried over Na₂SO₄, and concentrated to afford Preparation 31B (0.58 g, 1.485 mmol, 89% yield). LC/MS (PHENOMENEX® Luna 5 micron C18 4.6×30 mm, 30 to 100 B in 4 min with 1 min hold time, Flow rate=5 ml/min, detection at 254 nm, Solvent A: 10% methanol/90% water/0.1% TFA; Solvent B: 10% water/90% methanol/0.1% TFA) Rt=2.47. MS(ES):m/z=391.16 [M+H⁺].

Preparation 31C: Benzyl 9-((4-methoxybenzyl)(2-methoxyethyl)amino)-2-oxo-5-phenyl-2,3-dihydro-1H-benzo[e][1,4]diazepin-3-ylcarbamate (31C)

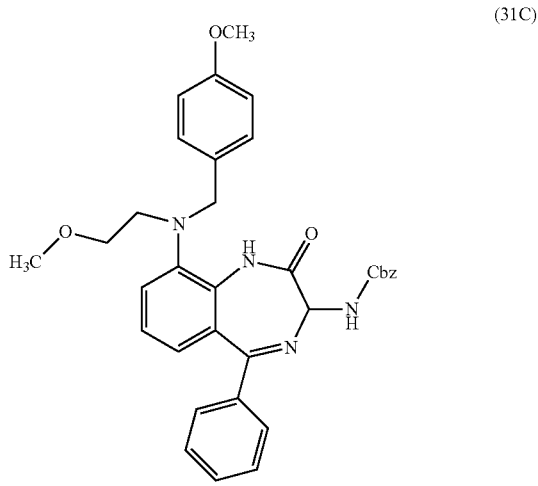 [SMILES: COCCN(Cc1ccc(OC)cc1)c1cccc2c1NC(=O)C(NC(=O)OCc1ccccc1)N=C2c1ccccc1]

Oxalyl chloride (0.288 mL, 3.33 mmol) was added to a solution of 2-(1H-benzo[d][1,2,3]triazol-1-yl)-2-(benzyloxycarbonylamino)acetic acid (0.109 g, 3.33 mmol) in THF (30 mL) cooled at 0° C., followed by DMF (0.1 mL, 1.665 mmol). After 2 h, (2-amino-3-((4-methoxybenzyl)(2-methoxyethyl)amino)phenyl)(phenyl)methanone 31B (0.65 g, 1.665 mmol) and N-methylmorpholine (0.549 mL, 4.99 mmol) dissolved in THF (10 mL) was added to the acid chloride solution at 0° C. The reaction mixture was removed from ice-bath and stirred at room temperature. After 2 h, the reaction mixture was filtered through CELITE®, washed with 5 mL THF and treated with $NH_3$ in methanol (30 mL, 210 mmol, 7N).

After 16 h, the reaction mixture was concentrated and taken up in ethyl acetate and 1N NaOH (100 mL) and extracted 3×100 mL ethyl acetate, dried and concentrated. The reaction crude was dissolved in acetic acid (25 mL) with ammonium acetate (0.642 g, 8.32 mmol) and stirred at room temperature for 4 h. Then the reaction mixture was concentrated and taken up in 200 mL saturated $NaHCO_3$. The pH was adjusted to 10 with 1N NaOH and extracted 3×100 mL DCM, dried over $Na_2SO_4$, concentrated and triturated with diethyl ether to afford Preparation 31C (0.372 g, 0.643 mmol, 38.6% yield) as a tan solid. $^1$H NMR (500 MHz, chloroform-d) δ 9.28 (s, 1H), 7.54-7.32 (m, 12H), 7.19-7.09 (m, 2H), 7.08-7.02 (m, 2H), 6.82-6.72 (m, J=8.6 Hz, 2H), 6.67 (d, J=7.8 Hz, 1H), 5.20 (s, 2H), 4.73 (d, J=7.8 Hz, 1H), 4.18 (d, J=12.5 Hz, 1H), 4.06 (d, J=12.8 Hz, 1H), 3.70 (s, 3H), 3.48-3.36 (m, 2H), 3.36-3.27 (m, 5H), 3.18-3.08 (m, 1H).

Preparation 31D: (2S,3R)-tert-Butyl 6,6,6-trifluoro-3-(9-(2-methoxyethylamino)-2-oxo-5-phenyl-2,3-dihydro-1H-benzo[e][1,4]diazepin-3-ylcarbamoyl)-2-(3,3,3-trifluoropropyl)hexanoate

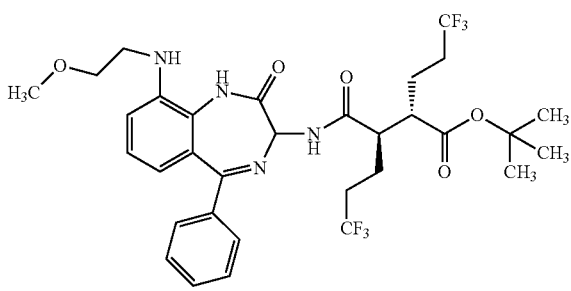

(31D)

Benzyl-9-((4-methoxybenzyl)(2-methoxyethyl)amino)-2-oxo-5-phenyl-2,3-dihydro-1H-benzo[e][1,4]diazepin-3-yl-carbamate 31C (0.25 g, 0.432 mmol) was treated with 33% HBr in acetic acid (4 mL) and stirred at room temperature for 30 minutes. Next, 20 mL of diethyl was added and the resulting solid material was collected via Buchner filtration, re-dissolved in methanol, and azeotroped once with toluene (5 mL). The mixture was dissolved in DMF (4 mL) and treated with TBTU (0.166 g, 0.518 mmol), and TEA (0.599 mL, 4.32 mmol), and stirred at room temperature for 2 h. The reaction mixture was added to water (50 mL) and the resulting solid material was collected via Buchner filtration to afford Preparation 31D (0.260 g, 0.387 mmol, 89% yield) as a tan solid.

Preparation 31E: (2R,3S)—N1-((S)-9-(2-Methoxyethylamino)-2-oxo-5-phenyl-2,3-dihydro-1H-benzo[e][1,4]diazepin-3-yl)-2,3-bis(3,3,3-trifluoropropyl)succinamide

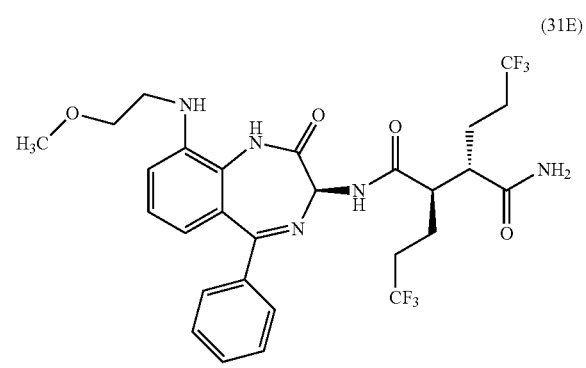 [SMILES: COCCNc1cccc2c1NC(=O)[C@@H](NC(=O)[C@H](CCC(F)(F)F)[C@H](CCC(F)(F)F)C(N)=O)N=C2c1ccccc1]

(31E)

To a solution of Preparation 31D (0.260 g, 0.387 mmol) in DCM (6 mL) at room temperature was added TFA (6 mL). The reaction mixture was stirred at room temperature for 2 h. The reaction mixture was concentrated and azeotroped with toluene. The reaction mixture was dissolved in DMF (6.00 mL) and TEA (0.804 mL, 5.80 mmol), HOBT hydrate (0.178 g, 1.160 mmol) and EDAC (0.222 g, 1.160 mmol) were added. The mixture was stirred at room temperature for 16 h. Next, 20 mL of water was added and the resulting solid material was collected via Buchner filtration to afford 164 mg of a tan solid that was purified by preparative SFC chromatography (Berger SFC MGII, CHIRALPAK® IB 25×2 cm ID, 5 μm, 90/10 $CO_2$/MeOH, 50 mL/min) to afford Preparation 31E. $^1$H NMR (500 MHz, methanol-$d_4$) δ 7.67-7.59 (m, 2H), 7.53-7.46 (m, 1H), 7.44-7.34 (m, 2H), 7.16 (t, J=7.9 Hz, 1H), 6.99 (dd, J=8.2, 1.0 Hz, 1H), 6.66 (dd, J=7.8, 1.1 Hz, 1H), 5.44 (s, 1H), 3.79-3.65 (m, 2H), 3.49-3.40 (m, 5H), 2.82 (td, J=10.5, 3.9 Hz, 1H), 2.60 (td, J=10.5, 3.7 Hz, 1H), 2.52-2.40 (m, 1H), 2.32-2.12 (m, 3H), 1.97-1.74 (m, 4H).

Example 31

To a solution of Preparation 31E (0.020 g, 0.032 mmol) in DMF (0.5 mL) at room temperature was added cesium carbonate (0.032 g, 0.097 mmol), followed by the addition of 1,2-dibromoethane (0.014 mL, 0.162 mmol). The reaction mixture was stirred at room temperature for 3 h and then filtered to remove the solid material. The filtrate was diluted with EtOAc and water. The organic layer was separated and washed with water (2×), brine, dried over $MgSO_4$, filtered and concentrated to give a crude material. This crude material was purified with ISCO 12 g column, 30 mL/min. 0-100% EtOAc/hexane in 15 min and hold at 100% EtOAc for 5 min. The product was eluted with 80% EtOAc/hexane to afford Example 31 (0.013 g, 0.020 mmol, 61.1% yield) as an off-white solid. HPLC: RT=10.028 min ($H_2O$/$CH_3CN$ with TFA, Sunfire C18 3.5 μm, 3.0×150 mm, gradient=15 min, wavelength=220 and 254 nm); MS(ES):m/z=642.3 [M+H$^+$]; $^1$H NMR (400 MHz, chloroform-d) δ 7.67-7.54 (m, 3H), 7.49-7.40 (m, 1H), 7.39-7.32 (m, 2H), 7.07 (t, J=8.0 Hz, 1H), 6.89 (dd, J=8.5, 1.0 Hz, 1H), 6.64 (dd, J=7.7, 1.1 Hz, 1H), 6.24 (br. s., 1H), 5.69-5.53 (m, 2H), 4.95-4.77 (m, 1H), 3.75-3.50 (m, 6H), 3.45-3.32 (m, 3H), 3.02 (ddd, J=12.8, 10.5, 4.7 Hz, 1H), 2.77-2.56 (m, 2H), 2.33-2.06 (m, 5H), 2.01-1.72 (m, 3H).

BIOLOGICAL ASSAYS

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pCDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1× glutamine/penicillin/streptomycin and 10% Fetal Bovine serum, were transiently transfected in a T175 Flask ($4.5 \times 10^6$ cells/flask) using the Monster Transfection Kit (Minis #MIR2906) according to manufacturers specifications. Table 1 denotes respective DNA quantity for the transfections.

TABLE 1

|  | DNA (µg) | CBF1 (µg) | Vector (µg) | Total DNA (µg) |
|---|---|---|---|---|
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of $5 \times 10^3$ cells/well in 95 µL assay media (DMEM (high glucose with HEPES), 1× glutamine/penicillin/streptomycin, 0.0125% BSA, 1× non-essential amino acids). Assay media (5 µL) containing test compounds in final concentrations ranging from 5 µM to $8.4 \times 10^{-5}$ µM (3 fold serial dilutions) were added to the cells and the cell plates were then incubated for 18 hours at 37° C. and 5% $CO_2$. Control wells contained DMSO vehicle (total counts) or 0.5 µM of an in-house small molecule inhibitor (background counts). Duplicates were used for each sample. Luciferase activity was measured after a 20-minute incubation with 50 µl STEADY-GLO® luciferase reagents according to manufacturer's specifications (Promega, Cat. #E2550) and analyzed by Envision plate reader (PerkinElmer, Boston, Mass.).

The antagonist effect of compounds was expressed as 100× [1−(average sample−average background)/(average total−average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 2 below lists the Notch 1 and Notch 3 $IC_{50}$ values for Examples 1-31 of this invention measured in the Notch-CBF1 Transactivation Assay hereinabove. In some instances, the value is an average of multiple experiments where N is the number of experiments conducted. The compounds of the present invention, as exemplified by the Examples 1-31 showed Notch 1 values of 21.9 nM or less and Notch 3 $IC_{50}$ values of 28.3 nM or less.

TABLE 2

| Example | Notch 1 $IC_{50}$ (nM) | N | Notch 3 $IC_{50}$ (nM) | N |
|---|---|---|---|---|
| 1 | 4.0 | 2 | 3.6 | 2 |
| 2 | 6.3 | 1 | 9.6 | 1 |
| 3 | 8.9 | 2 | 11.0 | 2 |
| 4 | 4.7 | 5 | 4.7 | 5 |
| 5 | 5.1 | 2 | 5.9 | 2 |
| 6 | 5.2 | 1 | 14.8 | 1 |
| 7 | 10.5 | 3 | 14.8 | 3 |
| 8 | 14.8 | 1 | 28.1 | 1 |
| 9 | 5.0 | 1 | 10.5 | 1 |
| 10 | 5.4 | 2 | 5.9 | 2 |
| 11 | 6.8 | 2 | 14.7 | 2 |
| 12 | 6.0 | 1 | 10.9 | 1 |
| 13 | 14.8 | 1 | 12.9 | 1 |
| 14 | 8.3 | 1 | 10.5 | 1 |
| 15 | 16.9 | 1 | 28.3 | 1 |
| 16 | 7.0 | 1 | 8.0 | 1 |
| 17 | 13.9 | 1 | 20.1 | 1 |
| 18 | 21.9 | 1 | 16.4 | 1 |
| 19 | 3.6 | 1 | 6.3 | 1 |
| 20 | 2.2 | 1 | 2.5 | 1 |
| 21 | 3.9 | 1 | 3.7 | 1 |
| 22 | 4.2 | 1 | 5.1 | 1 |
| 23 | 6.5 | 1 | 14.2 | 1 |
| 24 | 16.9 | 1 | 28.3 | 1 |
| 25 | 14.5 | 2 | 16.9 | 2 |
| 26 | 7.1 | 1 | 13.2 | 1 |
| 27 | 15.1 | 1 | 7.1 | 1 |
| 28 | 4.1 | 1 | 7.4 | 1 |
| 29 | 2.6 | 1 | 3.9 | 1 |
| 30 | 5.2 | 1 | 8.5 | 1 |
| 31 | 3.1 | 1 | 4.5 | 1 |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining) In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 3.

TABLE 3

Metabolic Stability - Result Interpretation Guidelines

| CYP-Mediated Clearance | Percent Remaining after 10 minutes | | | | |
|---|---|---|---|---|---|
| | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Methods and Materials
Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 µl of liver microsome suspension, protein concentration of 1.1 mg/ml in 100 mM $NaP_i$, pH 7.4, 5 mM $MgCl_2$ buffer, was pre-warmed at 37° C.

2. 1.7 µl of 50 µM compound (98.6% ACN, 1.4% DMSO) was added to the same tube and pre-incubated at 37° C. for 5 minutes.

3. The reaction was initiated by the addition of 17 µl of pre-warmed 10 mM NADPH solution in 100 mM $NaP_i$, pH 7.4.

The reaction components were mixed well, and 75 µl of the reaction mixture was immediately transferred into 150 µl quench/stop solution (zero-time point, $T_0$). Reactions were incubated at 37° C. for 10 minutes and then an additional 75 µl aliquot was transferred into 150 µl quench solution. Acetonitrile containing 100 µM DMN (a UV standard for injection quality control), was used as the quench solution to terminate metabolic reactions.

Quenched mixtures were centrifuged at 1500 rpm (~500×g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for UV-LC/MS-MS analysis to determine the percent of parent compound that remained in the mixture.

TABLE 4

Metabolic Stability Assay - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0 minutes and 10 minutes |
| Quench/Stop Solution (ACN + 100 µM DMN) | 150 µl |
| Sample of Reaction | 75 µl |
| Sedimentation of Denatured Microsomes | 15 minutes |
| UV-LC/MS analysis of supernatant | 0.17 µM |

Sample Analysis—Instrumentation

HPLC: Pump—Thermo Surveyor; Autosampler—CTC/LEAP HTS; UV detector—Thermo Surveyor PDA plus; Column—VARIAN® C18, 3 µm, 2×20 mm with a 0.5 µm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer: Thermo TSQ QUANTUM® Ultra triple-quadrupole mass spectrometer.

Sample Analysis—Structural Integrity Pre-Analysis

The Metabolic Stability structural integrity pre-analysis was used to assess the purity of compounds being assayed. Compounds were received in 96-well plates as 57 µl of a 3.5 mM DMSO solution. The 3.5 mM compound DMSO stock solutions were diluted 18-fold with a solution containing equal volumes of acetonitrile, isopropanol, and MilliQ-$H_2O$. The resulting solutions (200 µM) were analyzed for structural integrity by LC-UV/MS on a Thermo LCQ Deca XP Plus ion trap mass spectrometer, using a Waters XBridge C18, 5 µm, 2×50 mm column with a Waters Sentry 2.1 mm guard column, and the LC conditions described in the table below, with a 5 µl injection and a flow rate of 1 ml/min. The acquired data reflected purity by UV absorbance at 220 nm. Only results for those compounds with purity greater than 50% were reported.

TABLE 5

Metabolic Stability - Structural Integrity Gradient

| Gradient Time (min) | A % | B % |
|---|---|---|
| 0.00 | 100 | 0 |
| 4.00 | 0 | 100 |
| 5.00 | 0 | 100 |
| 5.10 | 100 | 0 |
| 6.00 | 100 | 0 |

Sample Analysis—Incubated Samples

MS/MS condition optimization was conducted on a Thermo TSQ QUANTUM® triple-quadrupole mass spectrometer equipped with a heated-electrospray (H-ESI) source by automated infusion to obtain the SRM transitions and their corresponding collision energy values. Compound solutions at a concentration of 20 µM in 1:1 methanol:water were infused at a flow rate of 90 µL/min, then combined with the mobile phase at a flow rate of 50 µL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a MICROSOFT ACCESS® database.

The mass spectrometric conditions obtained from automated infusion were used to analyze incubation samples from the Metabolic Stability assay. The injection volume was 5 µl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 6

Metabolic Stability - Sample Analysis Gradient

| Gradient Time (min) | A % (or C %) | B % (or D %) |
|---|---|---|
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the $T_{10minute}$ samples to those from the $T_{0minute}$ samples for each compound.

Quality Control

A set of three compounds was tested along with the test compound in each assay plate. Data was accepted and uploaded only if the results for these control compounds fall into the expected ranges shown below.

TABLE 7

Metabolic Stability Assay - Control Compound Values by Microsome Species

| | Average Percent Remaining ± SD | | | | |
|---|---|---|---|---|---|
| Compound | Human | Rat | Mouse | Dog | Monkey |
| Nefazodone | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carbamezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance (CLh,b) of a compound. These parameters were useful for predicting in vivo human clearance, which defines the level of drug exposure in vivo (Obach et al., 1997, 1999).

The metabolic stability half-life assay panel evaluates the time-course and the rate of CYP-mediated (NADPH-dependent) metabolism in vitro in human, rat, mouse, dog and monkey microsomes. The time course spans a 45 minute incubation, and includes 0, 5, 10, 15, 30, and 45 minute time-points, at each of which the amount of test compound remaining in the mixture was measured.

Result Interpretation Guideline

The results of the metabolic stability half-life assay are expressed as a half-life ($T_{1/2}$, min). In general, these results should be used to evaluate only the extent of CYP-mediated, or NADPH-dependent, metabolism of the test compound. When the compound was significantly metabolized ($T_{1/2}$<14 minutes), this indicated high clearance in vivo due to CYP-mediated metabolism. However, if the compound demonstrated moderate (14-70 minutes) or low (>70 minutes) metabolism in these in vitro assays, high clearance was still possible in vivo via other metabolism and elimination pathways.

The results of these assays were predictive of compound clearance in vivo, assuming that CYP-mediated metabolism was a predominant elimination pathway. In human microsomes, the ranges of results were approximately as shown in the following table.

TABLE 8

Metabolic Stability Half-Life-Result Interpretation Guidelines

| CYP-Mediated Clearance | $T_{1/2}$, minutes Human |
|---|---|
| Low | >70 |
| Medium | 14-70 |
| High | <14 |

Methods and Materials

Liver microsomes were purchased from BD-Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 µl of liver microsome suspension, protein concentration of 1.1 mg/ml in 100 mM $NaP_i$, pH 7.4, 5 mM $MgCl_2$ buffer, was pre-warmed at 37° C.

2. 5 µl of 50 µM compound (98.6% ACN, 1.4% DMSO) was added to the same tube and pre-incubated at 37° C. for 5 minutes.

3. The reaction was initiated by the addition of 50 µl of pre-warmed 10 mM NADPH solution in 100 mM $NaP_i$, pH 7.4.

Reaction components were mixed well, and 65 µl were immediately transferred into 130 µl quench/stop solution (zero-time point, $T_0$). Reactions were incubated at 37° C. for 5, 10, 15, 30 and 45 minutes and at each time-point a 65 µl aliquot was transferred into 130 µl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for LC/MS-MS analysis to determine the percent of parent compound that was remaining in the mixture.

TABLE 9

Metabolic Stability Half-Life Assays - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0, 5, 10, 15, 30, and 45 minutes |
| Quench/Stop Solution (ACN + 100 µM DMN) | 130 µl |
| Sample of Reaction | 65 µl |
| Sedimentation of Denatured Microsomes | 15 minutes |

Sample Analysis—Instrumentation

HPLC: Pump—Shimadzu LC-20 AD series binary pumps; Autosampler—CTC/LEAP HTS.

Human Tumor Xenograft Models in Mice

All rodents were obtained from Harlan Sprague Dawley Co. (Indianapolis, Ind.), and maintained in an ammonia-free environment in a defined and pathogen—free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in immunocompromized balb/c nu/nu nude or NOD-SCID mice (Harlan Sprague Dawley). Tumors were propagated as subcutaneous transplants in the appropriate mouse strain (Table 10) using tumor fragments obtained from donor mice.

TABLE 10

Histological Types and Host Mouse Strain/Gender Requirement for the Propagation of Various Human Tumor Xenografts in Mice

| Tumor Type | Histology | Mouse Strain | Sex |
|---|---|---|---|
| TALL-1 | ALL | NOD-SCID | female |
| HPB-ALL | ALL | NOD-SCID | female |
| ALL-SIL | ALL | NOD-SCID | female |
| MDA-MB-157 | breast | NOD-SCID | female |
| MDA-MB-468 | breast | NOD-SCID | female |
| PAT-34 | ovarian | nude | female |
| PAT-50 | ovarian | nude | female |
| PAT-26 | pancreas | nude | female |
| PAT-27 | pancreas | nude | female |

Preclinical Chemotherapy Trials

The required numbers of animals needed to detect a meaningful response were pooled at the start of the experiment and each was given a subcutaneous implant of a tumor fragment (~20 mg) with a 13-gauge trocar. Tumors were allowed to grow to the pre-determined size window (tumors outside the range were excluded) and animals were evenly distributed to various treatment and control groups. There were typically 8 mice per treatment and control groups, with the exception of experiments conducted in the SAL-IGF (this is not included in Table 10) tumor model, in which there were typically 5 mice per treatment and control group. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

Tumor weight=(length×width$^2$)÷2

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e., TGI≥50%) or log cell kill of 0.5 or greater (LCK≥0.5) for a period equivalent to at least 1 tumor volume doubling time and drug treatment must be for a period equivalent to at least 2 tumor volume doubling time.

Tumor response was also expressed in terms of tumor growth delay (TGD value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e., more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Drug Administration

In in vitro studies, all agents were dissolved in 100% DMSO and serially diluted in media/10% fetal bovine serum. For administration of Notch inhibitors to rodents, the following excipients were used: ETOH/TPGS/PEG300 (10:10:80). Notch inhibitors were typically administered orally on a schedule of QD×15, 10 day-on-2 day-off, although other schedules had also been evaluated and shown to be efficacious. For example, dosing regimen consisting of QD×12, 4 day-on-3 day-off was shown to be equally efficacious as QD×15, 10 day-on-2 day-off.

In Vivo Antitumor Activity

The antitumor activity of Example 1 administered via the intravenous route (IV) was evaluated in human tumor xenografts implanted in mice. As shown in Figure 6, Example 1 exhibited antitumor activity.

Table 11 below lists the antitumor activity of examples of this invention measured in the Human Tumor Xenograft Models in mice. The compounds of the present invention, as exemplified by Examples 1 and 2, showed antitumor activity with oral administration (PO).

TABLE 11

Schedule: QDx10; Oral Administration

| Example | Dose (mg/kg) | Antitumor Activity TALL1 (LCK) |
|---|---|---|
| 7 | 60 | 0.7 |

QD—once daily
LCK—Log Cell Kill

What is claimed is:

1. A compound of Formula (I):

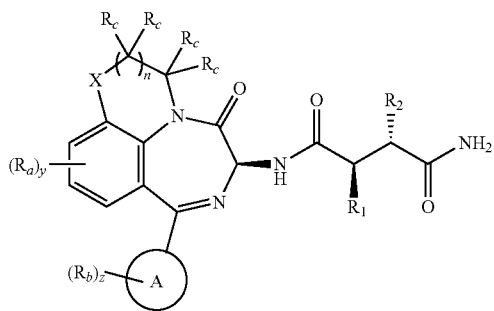

wherein:

X is O or —NR$_3$;

R$_1$ is —CH$_2$CH$_2$CH$_3$, —CH$_2$CF$_3$, —CH$_2$CH$_2$CF$_3$, —CH$_2$CF$_2$CH$_3$, —CH$_2$CH$_2$CH$_2$CF$_3$, —CH$_2$CH$_2$CF$_2$CH$_3$, —CH$_2$CH(CH$_3$)CF$_3$, —CH$_2$CH$_2$CH$_2$F, or —CH$_2$(cyclopropyl);

R$_2$ is —CH$_2$CH$_2$CH$_3$, —CH$_2$CF$_3$, —CH$_2$CH$_2$CF$_3$, —CH$_2$CF$_2$CH$_3$, —CH$_2$CH$_2$CH$_2$CF$_3$, —CH$_2$CH$_2$CH$_2$F, —CH$_2$CH(CH$_3$)CF$_3$, —CH$_2$CH$_2$CF$_2$CH$_3$, —CH$_2$(cyclopropyl), —CH(CH$_3$)(cyclopropyl), phenyl, fluorophenyl, chlorophenyl, trifluorophenyl, methylisoxazolyl, pyridinyl,

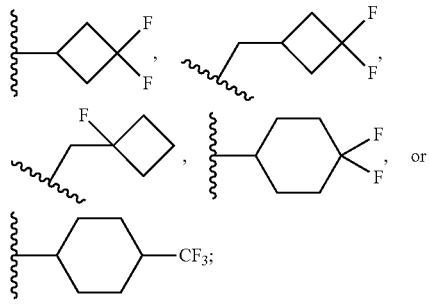

R$_3$ is H, C$_{1-3}$alkyl, —CH$_2$CH$_2$OH, or —CH$_2$CH$_2$OCH$_3$;

Ring A is phenyl or pyridinyl;

each R$_a$ is independently F, Cl, Br, C$_{1-3}$ alkyl, —CH$_2$OH, —CF$_3$, —CN, cyclopropyl, —OCH$_3$, —O(cyclopropyl), —OCH$_2$CH$_2$OCH$_3$, and/or

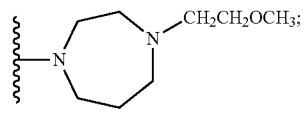

or two adjacent R$_a$ along with the carbon atoms to which they are attached form a dioxole ring;

each R$_b$ is independently F, Cl, —CH$_3$, —CH$_2$OH, —CH$_2$F, —CF$_3$, cyclopropyl, and/or —OCH$_3$;

each R$_c$ is independently H, F, Cl, and/or —CH$_3$;

n is 1 or 2;

y is zero, 1, or 2; and z is zero, 1, or 2.

2. The compound according to claim 1 wherein X is O.

3. The compound according to claim 1 wherein X is NR$_3$.

4. The compound according to claim 1 wherein:
R$_1$ is —CH$_2$CH$_2$CH$_3$, —CH$_2$CH$_2$CF$_3$, or —CH$_2$(cyclopropyl); and
R$_2$ is —CH$_2$CH$_2$CH$_3$, —CH$_2$CH$_2$CF$_3$, —CH$_2$CH$_2$CH$_2$F, —CH$_2$(cyclopropyl), phenyl, or methylisoxazolyl.

5. The compound according to claim 1 wherein Ring A is phenyl.

6. The compound according to claim 1 wherein:
R$_1$ is —CH$_2$CH$_2$CH$_3$, —CH$_2$CH$_2$CF$_3$, or —CH$_2$(cyclopropyl);
R$_2$ is —CH$_2$CH$_2$CH$_3$, —CH$_2$CH$_2$CF$_3$, —CH$_2$CH$_2$CH$_2$F, —CH$_2$(cyclopropyl), phenyl, or methylisoxazolyl;
R$_3$ is H or —CH$_2$CH$_2$OCH$_3$;
Ring A is phenyl;
R$_b$ is Cl or —CH$_3$;
each R$_c$ is independently H and/or F;
y is zero; and
z is zero or 1.

7. The compound according to claim 1 selected from: (2R,3R)—N-((7S)-3,3-difluoro-6-oxo-9-phenyl-3,4,6,7-tetrahydro-2H-[1,4]diazepino[1,7,6-ef][1,5]benzoxazepin-7-yl)-3-(3-methyl-4-isoxazolyl)-2-(3,3,3-trifluoropropyl)succinamide (1); (2R,3S)-3-(cyclopropylmethyl)-N-((7S)-3,3-difluoro-6-oxo-9-phenyl-3,4,6,7-tetrahydro-2H-[1,4]diazepino[1,7,6-ef][1,5]benzoxazepin-7-yl)-2-(3,3,3-trifluoropropyl)succinamide (2); (2R,3S)—N-((7S)-3,3-difluoro-6-oxo-9-phenyl-3,4,6,7-tetrahydro-2H-[1,4]diazepino[1,7,6-ef][1,5]benzoxazepin-7-yl)-3-propyl-2-(3,3,3-trifluoropropyl) succinamide (3); (2R,3R)-3-(3-methyl-4-isoxazolyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl)succinamide (4); (2R,3R)—N-((6S)-5-oxo-8-phenyl-2,3,5,6-tetrahydro[1,4]oxazino[2,3,4-jk][1,4]benzodiazepin-6-yl)-3-phenyl-2-(3,3,3-trifluoropropyl)succinamide (5); (2R,3S)-3-(cyclopropylmethyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl) succinamide (6); (2R,3S)—N-((6S)-5-oxo-8-phenyl-2,3,5,6-tetrahydro[1,4]oxazino[2,3,4-jk][1,4]benzodiazepin-6-yl)-3-propyl-2-(3,3,3-trifluoropropyl)succinamide (7); (2R,3S)-3-(3-fluoropropyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl)succinamide (8); (2R,3R)-3-(4-methyl-3-isoxazolyl)-N-((6S)-5-oxo-8-phenyl-2,3,5,6-tetrahydro[1,4]oxazino[2,3,4-jk][1,4]benzodiazepin-6-yl)-2-(3,3,3-trifluoropropyl) succinamide (9); (2R,3S)—N-((6S)-5-oxo-8-phenyl-2,3,5,6-tetrahydro[1,4]oxazino[2,3,4-jk][1,4]benzodiazepin-6-yl)-2,3-bis(3,3,3-trifluoropropyl)succinamide (10); (2R,3S)—N-((6S)-8-(3-methylphenyl)-5-oxo-2,3,5,6-tetrahydro[1,4]oxazino[2,3,4-jk][1,4]

benzodiazepin-6-yl)-2,3-bis(3,3,3-trifluoropropyl) succinamide (11); (2R,3S)—N-((6S)-8-(3-methylphenyl)-5-oxo-2,3,5,6-tetrahydro[1,4]oxazino[2,3,4-jk][1,4]benzodiazepin-6-yl)-3-propyl-2-(3,3,3-trifluoropropyl)succinamide (12); (2R,3R)—N-((6S)-8-(3-methylphenyl)-5-oxo-2,3,5,6-tetrahydro[1,4]oxazino[2,3,4-jk][1,4]benzodiazepin-6-yl)-3-phenyl-2-(3,3,3-trifluoropropyl)succinamide (13); (2R,3S)—N-((6S)-8-(3-chlorophenyl)-5-oxo-2,3,5,6-tetrahydro[1,4]oxazino[2,3,4-jk][1,4]benzodiazepin-6-yl)-2,3-bis(3,3,3-trifluoropropyl)succinamide (14); (2R,3S)—N-((6S)-8-(3-chlorophenyl)-5-oxo-2,3,5,6-tetrahydro[1,4]oxazino[2,3,4-jk][1,4]benzodiazepin-6-yl)-3-propyl-2-(3,3,3-trifluoropropyl) succinamide (15); (2R,3R)—N-((6S)-8-(3-chlorophenyl)-5-oxo-2,3,5,6-tetrahydro[1,4]oxazino[2,3,4-jk][1,4]benzodiazepin-6-yl)-3-(3-methyl-4-isoxazolyl)-2-(3,3,3-trifluoropropyl)succinamide (16); (2R,3S)—N-((6S)-5-oxo-8-phenyl-2,3,5,6-tetrahydro[1,4]oxazino[2,3,4-jk][1,4]benzodiazepin-6-yl)-2-propyl-3-(3,3,3-trifluoropropyl)succinamide (17); (2R,3S)-2,3-bis(cyclopropylmethyl)-N-((6S)-5-oxo-8-phenyl-2,3,5,6-tetrahydro[1,4]oxazino[2,3,4-jk][1,4]benzodiazepin-6-yl)succinamide (18); (2R,3S)—N-((7S)-6-oxo-9-phenyl-3,4,6,7-tetrahydro-2H-[1,4]diazepino[1,7,6-ef][1,5]benzoxazepin-7-yl)-2,3-bis(3,3,3-trifluoropropyl)succinamide (19); (2R,3R)-3-(3-methyl-4-isoxazolyl)-N-((7S)-6-oxo-9-phenyl-3,4,6,7-tetrahydro-2H-[1,4]diazepino[1,7,6-ef][1,5]benzoxazepin-7-yl)-2-(3,3,3-trifluoropropyl)succinamide (20); (2R,3R)—N-((7S)-6-oxo-9-phenyl-3,4,6,7-tetrahydro-2H-[1,4]diazepino[1,7,6-ef][1,5]benzoxazepin-7-yl)-3-phenyl-2-(3,3,3-trifluoropropyl)succinamide (21); (2R,3S)—N-((7S)-6-oxo-9-phenyl-3,4,6,7-tetrahydro-2H-[1,4]diazepino[1,7,6-ef][1,5]benzoxazepin-7-yl)-3-propyl-2-(3,3,3-trifluoropropyl)succinamide (22); (2R,3S)-3-(cyclopropylmethyl)-N-((7S)-6-oxo-9-phenyl-3,4,6,7-tetrahydro-2H-[1,4]diazepino[1,7,6-ef][1,5]benzoxazepin-7-yl)-2-(3,3,3-trifluoropropyl)succinamide (23); (2R,3R)-3-(3-methyl-4-isoxazolyl)-N-((6S)-5-oxo-8-phenyl-2,3,5,6-tetrahydro-1H-[1,4]diazepino[1,7,6-de]quinoxalin-6-yl)-2-(3,3,3-trifluoropropyl)succinamide (24); (2R,3S)—N-((6S)-5-oxo-8-phenyl-2,3,5,6-tetrahydro-1H-[1,4]diazepino[1,7,6-de]quinoxalin-6-yl)-3-propyl-2-(3,3,3-trifluoropropyl)succinamide (25); (2R,3S)-3-(cyclopropylmethyl)-N-((6S)-5-oxo-8-phenyl-2,3,5,6-tetrahydro-1H-[1,4]diazepino[1,7,6-de]quinoxalin-6-yl)-2-(3,3,3-trifluoropropyl)succinamide (26); (2R,3R)—N-((6S)-5-oxo-8-phenyl-2,3,5,6-tetrahydro-1H-[1,4]diazepino[1,7,6-de]quinoxalin-6-yl)-3-phenyl-2-(3,3,3-trifluoropropyl)succinamide (27); (2R,3S)—N-((6S)-5-oxo-8-phenyl-2,3,5,6-tetrahydro-1H-[1,4]diazepino[1,7,6-de]quinoxalin-6-yl)-2,3-bis(3,3,3-trifluoropropyl)succinamide (28); (2R,3S)—N-((6S)-8-(3-chlorophenyl)-5-oxo-2,3,5,6-tetrahydro-1H-[1,4]diazepino[1,7,6-de]quinoxalin-6-yl)-2,3-bis(3,3,3-trifluoropropyl)succinamide (29); (2R,3S)—N-((6S)-8-(3-methylphenyl)-5-oxo-2,3,5,6-tetrahydro-1H-[1,4]diazepino[1,7,6-de]quinoxalin-6-yl)-2,3-bis(3,3,3-trifluoropropyl)succinamide (30); and (2R,3S)—N-((6S)-1-(2-methoxyethyl)-5-oxo-8-phenyl-2,3,5,6-tetrahydro-1H-[1,4]diazepino[1,7,6-de]quinoxalin-6-yl)-2,3-bis(3,3,3-trifluoropropyl)succinamide (31).

8. A pharmaceutical composition comprising a compound according to claim 1; and a pharmaceutically acceptable carrier.

* * * * *